(12) United States Patent
Meyers

(10) Patent No.: US 6,664,089 B2
(45) Date of Patent: Dec. 16, 2003

(54) 38692 AND 21117, NOVEL DUAL SPECIFICITY PHOSPHATASE MOLECULES AND USES THEREFOR

(75) Inventor: Rachel A. Meyers, Newton, MA (US)

(73) Assignee: Millennium Pharmaceuticals, Inc., Cambridge, MA (US)

( * ) Notice: Subject to any disclaimer, the term of this patent is extended or adjusted under 35 U.S.C. 154(b) by 0 days.

(21) Appl. No.: 09/816,494

(22) Filed: Mar. 23, 2001

(65) Prior Publication Data

US 2002/0034807 A1 Mar. 21, 2002

Related U.S. Application Data

(60) Provisional application No. 60/191,858, filed on Mar. 24, 2000.

(51) Int. Cl.[7] .............................. C12N 9/16; C12N 1/20; C12N 15/00; C12P 21/04; C07H 21/04
(52) U.S. Cl. .................. 435/196; 435/252.3; 435/320.1; 435/71.1; 536/23.2
(58) Field of Search .............................. 435/196, 252.3, 435/320.1, 71.1; 536/23.2

(56) References Cited

FOREIGN PATENT DOCUMENTS

| EP | 1 033 401 A2 | 6/2000 |
|---|---|---|
| EP | 1 033 401 A2 | 9/2000 |
| WO | WO 99 02704 A | 1/1999 |
| WO | WO 01 46394 A | 6/2000 |
| WO | WO 01 20004 A | 3/2001 |

OTHER PUBLICATIONS

GenBank Accession AAB47561, Feb. 18, 1997.
GenBank Accession AI492892, Apr. 13, 1999.
GenBank Accession AI206123, Feb. 3, 1999.
GenBank Accession AA761314, Feb. 7, 1998.
GenBank Accession AA404320, May 16, 1997.
GenBank Accession U87169, Feb. 18, 1997.
GenBank Accession AAA87037, Feb. 8, 1996.
GenBank Accession AI637845, Apr. 27, 1999.
GenBank Accession AW014773, Sep. 10, 1999.
GenBank Accession AI807619, Dec. 19, 1999.
Altschul et al., *J. Mol. Biol.*, 1990, 215:403–410.
Altschul et al., *Nucleic Acids Res.*, 1997, 25(17):3389–3402.
International Human Genome Sequencing Consortium, *Initial sequencing and analysis of the human genome*, Nature 1, Vol 409, Feb. 15, 2001, www.nature.com.
Karlin et al., *Proc. Natl. Acad. Sci. USA*, 1990, 87(6):2264–2268.
Karlin et al., *Proc. Natl. Acad. Sci. USA*, 1993, 90(12):5873–5877.
*Molecular Cloning—A Laboratory Manual*, 2001, 3rd Edition, Sambrook et al. (eds.), Cold Spring Harbor Laboratory Press (Table of Contents only).

(List continued on next page.)

Primary Examiner—Ponnathapu Achutamurthy
Assistant Examiner—Yong Pak
(74) Attorney, Agent, or Firm—Millennium Pharmaceuticals, Inc.

(57) ABSTRACT

The invention provides isolated nucleic acids molecules, designated 38692 or 21117 nucleic acid molecules, which encode novel dual specificity phosphatase family members. The invention also provides antisense nucleic acid molecules, recombinant expression vectors containing 38692 or 21117 nucleic acid molecules, host cells into which the expression vectors have been introduced, and nonhuman transgenic animals in which a 38692 or 21117 gene has been introduced or disrupted. The invention still further provides isolated 38692 or 21117 proteins, fusion proteins, antigenic peptides and anti-38692 or 21117 antibodies. Diagnostic methods utilizing compositions of the invention are also provided.

6 Claims, 16 Drawing Sheets

OTHER PUBLICATIONS

Montserrat et al., "Dual specificity phosphatases: A gene family for Control of MAP kinase function", FASEB J., Feb. Of Amer. Soc. for Expir. Biol., Bethesda, MD, US, vol. 14, No. 1, Jan. 2000; 6–16.

Myers et al., *CABIOS*, 1988, 4:11–17.

Nagase et al., "Prediction of the coding sequences of unidentified human genes. XIX. The complete", DNA Research, vol. 7, No. 6, Dec. 2000; 347–55.

The Human Genome *The Sequence of the Human Genome*, Science, Vol 291, Feb. 16, 2001 www.sciencemag.org.

Sonnhammer et al., *Proteins*, 1997, 28(3):405–420.

Tanoue Takuji et al., "Molecular cloning and characterization of a novel dual specificity phosphatase, MKP–5", J.Biolog. Chem., American Soc. of Biolog. Chem., Baltimore, MD, US, vol. 274, No. 28, Jul. 1999; 19949–19956.

Weintraub et al., *Trends in Genetics*, Jan. 1985.
GenBank Accession No. AA404320, Apr. 1997.
GenBank Accession No. AA761314, Jan. 1998.
GenBank Accession No. AAA87037, Feb. 1996.
GenBank Accession No. AAB47561, Feb. 1997.
GenBank Accession No. AI206123, Oct. 1998.
GenBank Accession No. AI492892, Mar. 1999.
GenBank Accession No. AI637845, Apr. 1999.
GenBank Accession No. AI807619, Jul. 1999.
GenBank Accession No. AW014773, Sep. 1999.
GenBank Accession No. U87169, Feb. 1997.
GenBank Accession No. AC007619, May 1999.
GenBank Accession No. AI659120, May 1999.

START SEQ ID NO:1

TCCTATAGGGAGTCGCCCCGCGTCCGAAAAGATTATAAGTAAATACTCTGCTCTTTCAAGTGAACCAAACCTATCAAAC

CTGTTTAGAAAATAAACCAGGCAGAATAAAATGATGCGAAATGTTCATTTTAAAAAACTTCAGGATGGGCACAAACACA

CAGAAGTGGGAAATGAATAAAAGAGTATTGATAAATTTTTGAAAATTGTTGAAGCTGAGTAATGGGCTTTCAGTCCAGT

GTAAAGCTGTTGGAGCGCGGGAGCAAAGGTAAAGAATGATGTAATGCGCTGGCTGCTCCAAAGCATCTTTTGTTGTGGA

ATGGTTATTCCAGTCATCTCTTTATGAATCAAATGTGAGGGGCTGCTTTGTGGACGGAGTCCTTTGCAAGAGCACATCA

ACGGGAAAGAGAAAGAGACATTCACTTGGAGGGCTCTTGCTGAAAATGGGTTTAACTCTCCTTTTGCCAGTCACCACCA

GCCTGACCTCATACACTTTTAGTACAATGGAGTGGCTGAGCCTTTGAGCACACCACCATTACATCATCGTGGCAAATTA

| | | START SEQ ID NO:2 | M | A | H | E | M | I | G | T | Q | I | V | 11 |
|---|---|---|---|---|---|---|---|---|---|---|---|---|---|---|
| AAGAAGGAGGTGGGAAAAGAGGACTTATTGTTGTC | ATG | GCC | CAT | GAG | ATG | ATT | GGA | ACT | CAA | ATT | GTT | 33 |
| | | START SEQ ID NO:3 | | | | | | | | | | | | |

| T | E | R | L | V | A | L | L | E | S | G | T | E | K | V | L | L | I | D | S | 31 |
|---|---|---|---|---|---|---|---|---|---|---|---|---|---|---|---|---|---|---|---|---|
| ACT | GAG | AGG | TTG | GTG | GCT | CTG | CTG | GAA | AGT | GGA | ACG | GAA | AAA | GTG | CTG | CTA | ATT | GAT | AGC | 93 |

| R | P | F | V | E | Y | N | T | S | H | I | L | E | A | I | N | I | N | C | S | 51 |
|---|---|---|---|---|---|---|---|---|---|---|---|---|---|---|---|---|---|---|---|---|
| CGG | CCA | TTT | GTG | GAA | TAC | AAT | ACA | TCC | CAC | ATT | TTG | GAA | GCC | ATT | AAT | ATC | AAC | TGC | TCC | 153 |

| K | L | M | K | R | R | L | Q | Q | D | K | V | L | I | T | E | L | I | Q | H | 71 |
|---|---|---|---|---|---|---|---|---|---|---|---|---|---|---|---|---|---|---|---|---|
| AAG | CTT | ATG | AAG | CGA | AGG | TTG | CAA | CAG | GAC | AAA | GTG | TTA | ATT | ACA | GAG | CTC | ATC | CAG | CAT | 213 |

| S | A | K | H | K | V | D | I | D | C | S | Q | K | V | V | V | Y | D | Q | S | 91 |
|---|---|---|---|---|---|---|---|---|---|---|---|---|---|---|---|---|---|---|---|---|
| TCA | GCG | AAA | CAT | AAG | GTT | GAC | ATT | GAT | TGC | AGT | CAG | AAG | GTT | GTA | GTT | TAC | GAT | CAA | AGC | 273 |

| S | Q | D | V | A | S | L | S | S | D | C | F | L | T | V | L | L | G | K | L | 111 |
|---|---|---|---|---|---|---|---|---|---|---|---|---|---|---|---|---|---|---|---|---|
| TCC | CAA | GAT | GTT | GCC | TCT | CTC | TCT | TCA | GAC | TGT | TTT | CTC | ACT | GTA | CTT | CTG | GGT | AAA | CTG | 333 |

| E | K | S | F | N | S | V | H | L | L | A | G | G | F | A | E | F | S | R | C | 131 |
|---|---|---|---|---|---|---|---|---|---|---|---|---|---|---|---|---|---|---|---|---|
| GAG | AAG | AGC | TTC | AAC | TCT | GTT | CAC | CTG | CTT | GCA | GGT | GGG | TTT | GCT | GAG | TTC | TCT | CGT | TGT | 393 |

| F | P | G | L | C | E | G | K | S | T | L | V | P | T | C | I | S | Q | P | C | 151 |
|---|---|---|---|---|---|---|---|---|---|---|---|---|---|---|---|---|---|---|---|---|
| TTC | CCT | GGC | CTC | TGT | GAA | GGA | AAA | TCC | ACT | CTA | GTC | CCT | ACC | TGC | ATT | TCT | CAG | CCT | TGC | 453 |

Fig. 1A

```
L   P   V   A   N   I   G   P   T   R   I   L   P   N   L   Y   L   G   C   Q   171
TTA CCT GTT GCC AAC ATT GGG CCA ACC CGA ATT CTT CCC AAT CTT TAT CTT GGC TGC CAG 513

R   D   V   L   N   K   E   L   M   Q   Q   N   G   I   G   Y   V   L   N   A   191
CGA GAT GTC CTC AAC AAG GAG CTG ATG CAG CAG AAT GGG ATT GGT TAT GTG TTA AAT GCC 573

S   N   T   C   P   K   P   D   F   I   P   E   S   H   F   L   R   V   P   V   211
AGC AAT ACC TGT CCA AAG CCT GAC TTT ATC CCC GAG TCT CAT TTC CTG CGT GTG CCT GTG 633

N   D   S   F   C   E   K   I   L   P   W   L   D   K   S   V   D   F   I   E   231
AAT GAC AGC TTT TGT GAG AAA ATT TTG CCG TGG TTG GAC AAA TCA GTA GAT TTC ATT GAG 693

K   A   K   A   S   N   G   C   V   L   V   H   C   L   A   G   I   S   R   S   251
AAA GCA AAA GCC TCC AAT GGA TGT GTT CTA GTG CAC TGT TTA GCT GGG ATC TCC CGC TCC 753

A   T   I   A   I   A   Y   I   M   K   R   M   D   M   S   L   D   E   A   Y   271
GCC ACC ATC GCT ATC GCC TAC ATC ATG AAG AGG ATG GAC ATG TCT TTA GAT GAA GCT TAC 813

R   F   V   K   E   K   R   P   T   I   S   P   N   F   N   F   L   G   Q   L   291
AGA TTT GTG AAA GAA AAA AGA CCT ACT ATA TCT CCA AAC TTC AAT TTT CTG GGC CAA CTC 873

L   D   Y   E   K   K   I   K   N   Q   T   G   A   S   G   P   K   S   K   L   311
CTG GAC TAT GAG AAG AAG ATT AAG AAC CAG ACT GGA GCA TCA GGG CCA AAG AGC AAA CTC 933

K   L   L   H   L   E   K   P   N   E   P   V   P   A   V   S   E   G   G   Q   331
AAG CTG CTG CAC CTG GAG AAG CCA AAT GAA CCT GTC CCT GCT GTC TCA GAG GGT GGA CAG 993

K   S   E   T   P   L   S   P   P   C   A   D   S   A   T   S   E   A   A   G   351
AAA AGC GAG ACG CCC CTC AGT CCA CCC TGT GCC GAC TCT GCT ACC TCA GAG GCA GCA GGA 1053

Q   R   P   V   H   P   A   S   V   P   S   V   P   S   V   Q   P   S   L   L   371
CAA AGG CCC GTG CAT CCC GCC AGC GTG CCC AGC GTG CCC AGC GTG CAG CCG TCG CTG TTA 1113
```

Fig. 1B

```
  E   D   S   P   L   V   Q   A   L   S   G   L   H   L   S   A   D   R   L   E  391
 GAG GAC AGC CCG CTG GTA CAG GCG CTC AGT GGG CTG CAC CTG TCC GCA GAC AGG CTG GAA 1173

D   S   N   K   L   K   R   S   F   S   L   D   I   K   S   V   S   Y   S   A  411
 GAC AGC AAT AAG CTC AAG CGT TCC TTC TCT CTG GAT ATC AAA TCA GTT TCA TAT TCA GCC 1233

S   M   A   A   S   L   H   G   F   S   S   S   E   D   A   L   E   Y   Y   K  431
 AGC ATG GCA GCA TCC TTA CAT GGC TTC TCC TCA TCA GAA GAT GCT TTG GAA TAC TAC AAA 1293

P   S   T   T   L   D   G   T   N   K   L   C   Q   F   S   P   V   Q   E   L  451
 CCT TCC ACT ACT CTG GAT GGG ACC AAC AAG CTA TGC CAG TTC TCC CCT GTT CAG GAA CTA 1353

S   E   Q   T   P   E   T   S   P   D   K   E   E   A   S   I   P   K   K   L  471
 TCG GAG CAG ACT CCC GAA ACC AGT CCT GAT AAG GAG GAA GCC AGC ATC CCC AAG AAG CTG 1413

Q   T   A   R   P   S   D   S   Q   S   K   R   L   H   S   V   R   T   S   S  491
 CAG ACC GCC AGG CCT TCA GAC AGC CAG AGC AAG CGA TTG CAT TCG GTC AGA ACC AGC AGC 1473

S   G   T   A   Q   R   S   L   L   S   P   L   H   R   S   G   S   V   E   D  511
 AGT GGC ACC GCC CAG AGG TCC CTT TTA TCT CCA CTG CAT CGA AGT GGG AGC GTG GAG GAC 1533

N   Y   H   T   S   F   L   F   G   L   S   T   S   Q   Q   H   L   T   K   S  531
 AAT TAC CAC ACC AGC TTC CTT TTC GGC CTT TCC ACC AGC CAG CAG CAC CTC ACG AAG TCT 1593

A   G   L   G   L   K   G   W   H   S   D   I   L   A   P   Q   T   S   T   P  551
 GCT GGC CTG GGC CTT AAG GGC TGG CAC TCG GAT ATC TTG GCC CCC CAG ACC TCT ACC CCT 1653

S   L   T   S   S   W   Y   F   A   T   E   S   S   H   F   Y   S   A   S   A  571
 TCC CTG ACC AGC AGC TGG TAT TTT GCC ACA GAG TCC TCA CAC TTC TAC TCT GCC TCA GCC 1713

I   Y   G   G   S   A   S   Y   S   A   Y   S   C   S   Q   L   P   T   C   G  591
 ATC TAC GGA GGC AGT GCC AGT TAC TCT GCC TAC AGC TGC AGC CAG CTG CCC ACT TGC GGA 1773

D   Q   V   Y   S   V   R   R   R   Q   K   P   S   D   R   A   D   S   R   R  611
 GAC CAA GTC TAT TCT GTG CGC AGG CGG CAG AAG CCA AGT GAC AGA GCT GAC TCG CGG CGG 1833
```

Fig. 1C

```
S   W   H   E   E   S   P   F   E   K   Q   F   K   R   R   S   C   Q   M   E   631
AGC TGG CAT GAA GAG AGC CCC TTT GAA AAG CAG TTT AAA CGC AGA AGC TGC CAA ATG GAA 1893

F   G   E   S   I   M   S   E   N   R   S   R   E   E   L   G   K   V   G   S   651
TTT GGA GAG AGC ATC ATG TCA GAG AAC AGG TCA CGG GAA GAG CTG GGG AAA GTG GGC AGT 1953
                                                              ┌─STOP SEQ ID NO:2
Q   S   S   F   S   G   S   M   E   I   I   E   V   S   *   666
CAG TCT AGC TTT TCG GGC AGC ATG GAA ATC ATT GAG GTC TCC TGA 1998
                                                      └─STOP SEQ ID NO:3
```

GAAGAAAGACACTTGTGACTTCTATAGACAATTTTTTTTTCTTGTTCACAAAAAAATTCCCTGTAAATCTGAAATATAT

ATATGTACATACATATATATTTTTGGAAAATGGAGCTATGGTGTAAAAGCAACAGGTGGATCAACCCAGTTGTTACTCT

CTTAACATCTGCATTTGAGAGATCAGCTAATACTTCTCTCAACAAAAATGGAAGGGCAGATGCTAGAATCCCCCCTAGA

CGGAGGAAAACCATTTTATTCAGTGAATTACACATCCTCTTGTTCTTAAAAAAGCAAGTGTCTTTGGTGTTGGAGGACA

AAATCCCCTACCATTTTCACGTTGTGCTACTAAGAGATCTCAAATATTAGTCTTTGTCCGGACCCTTCCATAGTACACC

TTAGCGCTGAGACTGAGCCAGCTTGGGGGTCAGGTAGGTAGACCCTGTTAGGGACAGAGCCTAGTGGTAAATCCAAGAG

AAATGATCCTATCCAAAGCTGATTCACAAACCCACGCTCACCTGACAGCCGAGGGACACGAGCATCACTCTGCTGGACG

GACCATTAGGGGCCTTGCCAAGGTCTACCTTAGAGCAAACCCAGTACCTCAGACAGGAAAGTCGGGGCTTTGACCACTA

CCATATCTGGTAGCCCATTTTCTAGGCATTGTGAATAGGTAGGTAGCTAGTCACACTTTTCAGACCAATTCAAACTGTC

TATGCACAAAATTCCCGTGGGCCTAGATGGAGATAATTTTTTTTTTCTTCTCAGCTTTATGAAGAGAAGGGAAACTGTCT

AGGATTCAGCTGAACCACCAGGAACCTGGCAACATCACGATTTAAGCTAAGGTTGGGAGGCTAACGAGTCTACCTCCCT

CTTTGTAAATCAAAGAATTGTTTAAAATGGGATTGTCAATCCTTTAAATAAAGATGAACTTGGTTTCAAAAAAAAAAAA
           ┌─STOP SEQ ID NO:1
AAAAAAAAGG

Fig. 1D

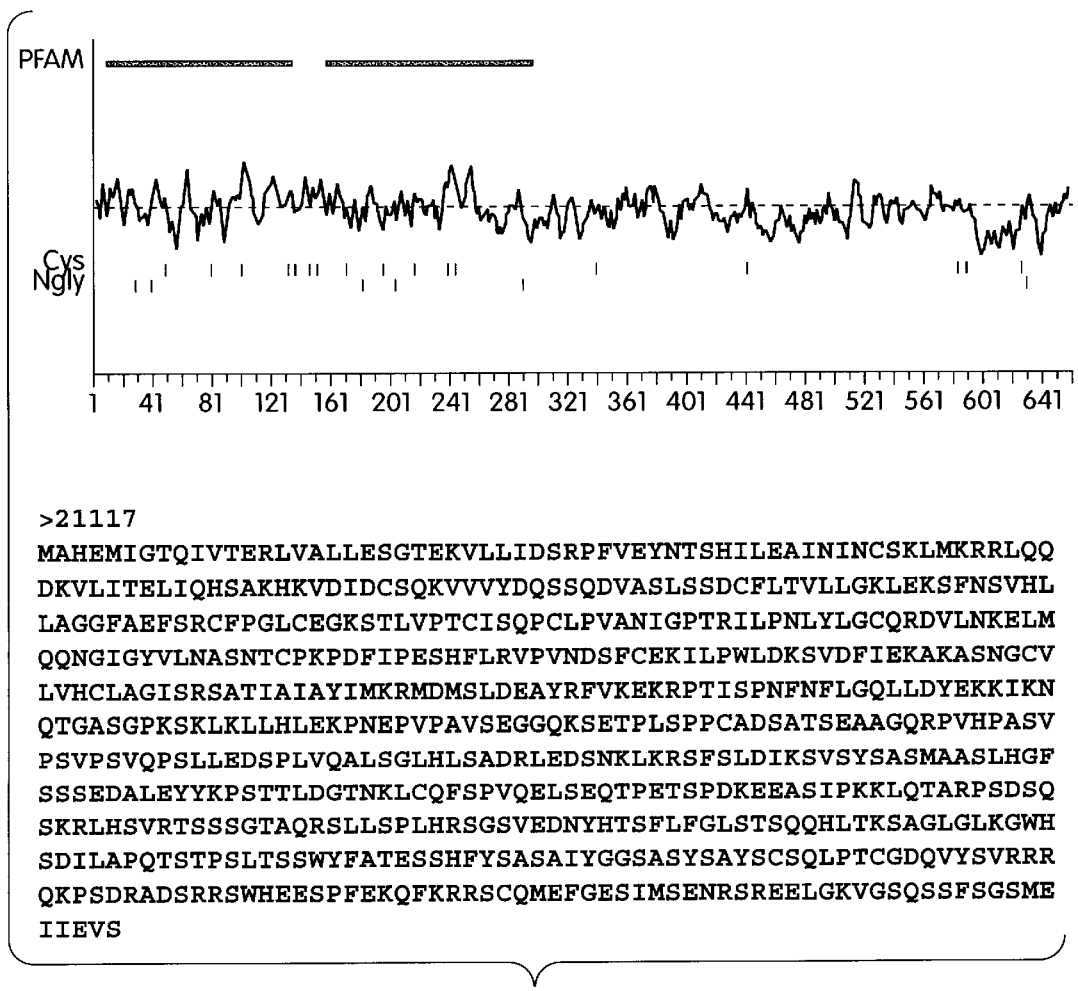

>21117
MAHEMIGTQIVTERLVALLESGTEKVLLIDSRPFVEYNTSHILEAININCSKLMKRRLQQ
DKVLITELIQHSAKHKVDIDCSQKVVVYDQSSQDVASLSSDCFLTVLLGKLEKSFNSVHL
LAGGFAEFSRCFPGLCEGKSTLVPTCISQPCLPVANIGPTRILPNLYLGCQRDVLNKELM
QQNGIGYVLNASNTCPKPDFIPESHFLRVPVNDSFCEKILPWLDKSVDFIEKAKASNGCV
LVHCLAGISRSATIAIAYIMKRMDMSLDEAYRFVKEKRPTISPNFNFLGQLLDYEKKIKN
QTGASGPKSKLKLLHLEKPNEPVPAVSEGGQKSETPLSPPCADSATSEAAGQRPVHPASV
PSVPSVQPSLLEDSPLVQALSGLHLSADRLEDSNKLKRSFSLDIKSVSYSASMAASLHGF
SSSEDALEYYKPSTTLDGTNKLCQFSPVQELSEQTPETSPDKEEASIPKKLQTARPSDSQ
SKRLHSVRTSSSGTAQRSLLSPLHRSGSVEDNYHTSFLFGLSTSQQHLTKSAGLGLKGWH
SDILAPQTSTPSLTSSWYFATESSHFYSASAIYGGSASYSAYSCSQLPTCGDQVYSVRRR
QKPSDRADSRRSWHEESPFEKQFKRRSCQMEFGESIMSENRSREELGKVGSQSSFSGSME
IIEVS

Fig. 2

```
DSPc: domain 1 of 1, from 158 to 297: score 244.5, E = 1.4e-69
   START SEQ ID NO:7   *->gpseIlphlYLGsystaseanlallkklgIthviNvteevpnpfeld
                           gp++Ilp+lYLG++++    n++l++++gI +v+N+++ +p+p++++
        21117    158    GPTRILPNLYLGCQRDVL--NKELMQQNGIGYVLNASNTCPKPDFIP 202 kkndrhytnayisknsgftylqiPnvdDhIYyhiawnhetkiskyfdeav
                           + ++l++P v+D          + ++ki++++d++v
        21117    203    ---------------ESHFLRVP-VND--------SFCEKILPWLDKSV 227 dFIddarqkggkVLVHCqAGiSRSAtliiAYLMktrnlslneAydfvyvY
                       dFI++a++++g VLVHC+AGiSRSAt++iAY+Mk++ +sl+eAy+fv
        21117    228    DFIEKAKASNGCVLVHCLAGISRSATIAIAYIMKRMDMSLDEAYRFV--- 274 hikerRcpiisPNfgFlrQLieyerk<-*  STOP SEQ ID NO:7
                          ke+R p isPNf+Fl+QL++ye+k
        21117    275    --KEKR-PTISPNFNFLGQLLDYEKK    297
```

Fig. 3A

```
dsp_5: domain 1 of 1, from 158 to 297: score 241.8, E = 9.7e-69
   START SEQ ID NO:8   *->gpseilphlYLGsysdaseanlallkklgIthviNvteevpnnfelk
                           gp++ilp+lYLG+++d +   n++l++++gI +v+N+++ +p+++++
        21117    158    GPTRILPNLYLGCQRDVL--NKELMQQNGIGYVLNASNTCPKPDFI- 201 kkndryytneyiskgsgftylqiPnvdDIyyhiawntetkiskyleeave
                          ++ ++l++P v+D          ++++ki+++l+++v+
        21117    202    ---------------PESHFLRVP-VND-------SFCEKILPWLDKSVD 228 fIedaekkggkVLVHCqAGvSRSAtlviAYLMktrnlslrdAydfvyvYh
                       fIe+a++++g VLVHC+AG+SRSAt++iAY+Mk++ +sl++Ay+fv
        21117    229    FIEKAKASNGCVLVHCLAGISRSATIAIAYIMKRMDMSLDEAYRFV---- 274 ikerRcpiisPNfgFlrQLieyerk<-*  STOP SEQ ID NO:8
                          ke+R p isPNf+Fl+QL++ye+k
        21117    275    -KEKR-PTISPNFNFLGQLLDYEKK    297
```

Fig. 3B

```
Alignments of top-scoring domains:
Rhodanese: domain 1 of 1, from 11 to 131: score 53.4, E = 4.9e-12
    START SEQ ID NO:9  *->tagelkalles.apkliliDvRspefGeeyeyegGHIpgAvNvp.ee
                         + + 1 alles+ +k++liD R++      ey+ +HI  A+N++
       21117     11     VTERLVALLESgTEKVLLIDSRPF-----VEYNTSHILEAININcSK  52 eiealldrsgilpdieklhllkdpeelaklfgelgsskd..krvivycrs
                         + + 1 ++  1             el++     ++++ d + +v+vy++s
       21117     53     LMKRRLQQDKVL-----------ITELIQHSAKHKVDIDcSQKVVVYDQS  91 grgl.lrnrrsalaalllkklG.ypeVyiLkGGykeWlak<-*STOP SEQ ID NO:9
                       ++++    + ++ 1 +11 k+    +++ V++L GG+ e++++
       21117     92     SQDVaSLSSDCFLTVLLGKLEKsFNSVHLLAGGFAEFSRC       131
```

Fig. 4A

```
Alignments of top-scoring domains:
rhod_4: domain 1 of 1, from 12 to 134: score 64.8, E = 1.8e-15
    START SEQ ID NO:10 *->v.leelkllln.edvvllDvRspeEyeggHIpGAvniplselldr..
                         ++ + ++l++++e+v+l+D R++ Ey+ +HI  A+ni++s l +r+
       21117     12     TeRLVALLESGtEKVLLIDSRPFVEYNTSHILEAININCSKLMKRrl  58

................lgldkdkpvivyCrsGvrs.....aakaawlL
                       ++++    ++  +++ +++ ++d  ++v+vy++s+ +   + ++++ ++ 1L
       21117     59     qqdkvliteliqhsakhkVDIDCSQKVVVYDQSSQDVaslssDCFLTVLL  108 relGfk..nVylLdGGykeWsaagpp<-*  STOP SEQ ID NO:10
                       +l   +  + V 1L GG++e+s+++p
       21117     109    GKLEKSfnSVHLLAGGFAEFSRCFPG        134
```

Fig. 4B

```
┌START SEQ ID NO:4
▼
CTATAGGGAGTCGCCCACGCGTCCGGGGCGGTGGCGCGCTGACACCTGGCGGCGGCGGAGGGCGGGCAGAAGCCCGCGG
          ┌START SEQ ID NO:5
          M ◄ E   D   V   K   L   E   F   P   S   L   P   Q   C   K   E   D    17
GCCAGCACC ATG GAG GAC GTG AAG CTG GAG TTC CCT TCC CTT CCA CAG TGC AAG GAA GAC    51
         └START SEQ ID NO:6

A   E   E   W   T   Y   P   M   R   R   E   M   Q   E   I   L   P   G   L   F   37
 GCC GAG GAG TGG ACC TAC CCT ATG AGA CGA GAG ATG CAG GAA ATT TTA CCT GGA TTG TTC  111

L   G   P   Y   S   S   A   M   K   S   K   L   P   V   L   Q   K   H   G   I   57
 TTA GGC CCA TAT TCA TCT GCT ATG AAA AGC AAG CTA CCT GTA CTA CAG AAA CAT GGA ATA  171

T   H   I   I   C   I   R   Q   N   I   E   A   N   F   I   K   P   N   F   Q   77
 ACC CAT ATA ATA TGC ATA CGA CAA AAT ATT GAA GCA AAC TTT ATT AAA CCA AAC TTT CAG  231

Q   L   F   R   Y   L   V   L   D   I   A   D   N   P   V   E   N   I   I   R   97
 CAG TTA TTT AGA TAT TTA GTC CTG GAT ATT GCA GAT AAT CCA GTT GAA AAT ATA ATA CGT  291

F   F   P   M   T   K   E   F   I   D   G   S   L   Q   M   G   G   K   V   L  117
 TTT TTC CCT ATG ACT AAG GAA TTT ATT GAT GGG AGC TTA CAA ATG GGA GGA AAA GTT CTT  351

V   H   G   N   A   G   I   S   R   S   A   A   F   V   I   A   Y   I   M   E  137
 GTG CAT GGA AAT GCA GGG ATC TCC AGA AGT GCA GCC TTT GTT ATT GCA TAC ATT ATG GAA  411

T   F   G   M   K   Y   R   D   A   F   A   Y   V   Q   E   R   R   F   C   I  157
 ACA TTT GGA ATG AAG TAC AGA GAT GCT TTT GCT TAT GTT CAA GAA AGA AGA TTT TGT ATT  471

N   P   N   A   G   F   V   H   Q   L   Q   E   Y   E   A   I   Y   L   A   K  177
 AAT CCT AAT GCT GGA TTT GTC CAT CAA CTT CAG GAA TAT GAA GCC ATC TAC CTA GCA AAA  531

L   T   I   Q   M   M   S   P   L   Q   I   E   R   S   L   S   V   H   S   G  197
 TTA ACA ATA CAG ATG ATG TCA CCA CTC CAG ATA GAA AGG TCA TTA TCT GTT CAT TCT GGT  591
```

ACC ACA GGC AGT TTG AAG AGA ACA CAT GAA GAA GAG GAT GAT TTT GGA ACC ATG CAA GTG   651
                                            ┌─STOP SEQ ID NO:5
         A   T   A   Q   N   G   *   224                ▼

GCG ACT GCA CAG AAT GGC TGA   672
                                ▲
                                └─STOP SEQ ID NO:6

CTTGAAGAGCAACATCATAGAGTGTGAATTTCTATTTGGGAAGGAGAAAATACAAGAGAAAATTATAATGTAAAATGGT

AAAAACATAAGTAGTTTTTTTTTTCAATTACATGTTGCTTCCAGACATACTTCTCTGCAACTTGTTGAGCAACATTTTAA

GATGTTGGACTTCTGCAATAGATGACACTGATGGTTTTACTCCTTTTTTTTAAAAACACATGCGCGCGCACACACACATG

CTTTACAAGTTTTATTATAAACCAAGAATTTTGGACTTGCAAAGAGGTATTATTGCAATAATGCACTTTTCATACTTGA

AATTTATTTGTATGATATAAAGTTATTACTTTAAACAA    STOP SEQ ID NO:4
```

Fig. 6B

>38692
MEDVKLEFPSLPQCKEDAEEWTYPMRREMQEILPGLFLGPYSSAMKSKLPVLQKHGITHI
ICIRQNIEANFIKPNFQQLFRYLVLDIADNPVENIIRFFPMTKEFIDGSLQMGGKVLVHG
NAGISRSAAFVIAYIMETFGMKYRDAFAYVQERRFCINPNAGFVHQLQEYEAIYLAKLTI
QMMSPLQIERSLSVHSGTTGSLKRTHEEEDDFGTMQVATAQNG

```
Alignments of top-scoring domains:
DSPc: domain 1 of 1, from 28 to 173: score 223.4, E = 3.3e-63
   START SEQ ID NO:7  *->gpseIlphlYLGsystaseanlallkklgIthviNvteevpnpfeld
                         +++eIlp+l+LG ys+a++++l+ l+k+gIth+i+  ++++++f+++
       38692      28    EMQEILPGLFLGPYSSAMKSKLPVLQKHGITHIICIRQNIEANFIKP   74 kkndrhytnayisknsgftylqiPnvdDhIYyhiawnhetkiskyfdeav
                         ++++ f+yl +  + D         n++++i  +f++++
       38692      75    ------------NFQQLFRYLVLD-IAD--------NPVENIIRFFPMTK  103 dFIddarqkggkVLVHCqAGiSRSAtliiAYLMktrnlslneAydfvyvY
                         +FId + q ggkVLVH  AGiSRSA+++iAY+M t+++++++A+ +v
       38692     104    EFIDGSLQMGGKVLVHGNAGISRSAAFVIAYIMETFGMKYRDAFAYV---  150 hikerRcpiisPNfgFlrQLieyerk<-*STOP SEQ ID NO:7
                         +erR ++i+PN+gF++QL+eye +
       38692     151    --QERR-FCINPNAGFVHQLQEYEAI     173
```

Fig. 8A

```
Alignments of top-scoring domains:
dsp_5: domain 1 of 1, from 28 to 173: score 225.8, E = 6.5e-64
   START SEQ ID NO:8  *->gpseilphlYLGsysdaseanlallkklgIthviNvteevpnnfelk
                         +++eilp+l+LG ys+a++++l+ l+k+gIth+i+  +++++nf+++
       38692      28    EMQEILPGLFLGPYSSAMKSKLPVLQKHGITHIICIRQNIEANFIKP   74 kkndryytneyiskgsgftylgiPnvdDIyyhiawntetkiskyleeave
                         ++++ f+yl +  + D         n++++i  ++++++e
       38692      75    ------------NFQQLFRYLVLD-IAD--------NPVENIIRFFPMTKE 104 fIedaekkggkVLVHCqAGvSRSAtlviAYLMktrnlslrdAydfvyvYh
                         fI+ + + ggkVLVH  AG+SRSA++viAY+M t+++++rdA+++v
       38692     105    FIDGSLQMGGKVLVHGNAGISRSAAFVIAYIMETFGMKYRDAFAYV----  150 ikerRcpiisPNfgFlrQLieyerk<-*STOP SEQ ID NO:8
                         +erR ++i+PN+gF++QL+eye +
       38692     151    -QERR-FCINPNAGFVHQLQEYEAI      173
```

Fig. 8B

38692 AND 21117, NOVEL DUAL SPECIFICITY PHOSPHATASE MOLECULES AND USES THEREFOR

CROSS-REFERENCE TO RELATED APPLICATIONS

This application claims priority to U.S. provisional application number 60/191,858, filed on Mar. 24, 2000, the contents of which are incorporated herein by reference.

BACKGROUND OF THE INVENTION

The intracellular phosphorylation of proteins is critical for a plethora of regulatory and signalling pathways in eukaryotic cells. Phosphorylation events can govern a wide range of cellular processes, including cell proliferation, differentiation, transcription, and morphology. An essential component of these signalling pathways is the ability of the cell to desensitize, recycle, and counteract phosphorylation signals. The cell primarily utilizes enzymes, termed phosphatases, which remove the phosphate on tyrosine, serine, and threonine side chains. The protein phosphatases are divided into three groups according to catalytic function: (1) protein phosphatases that dephosphorylate serine and threonine residues; (2) protein phosphatases which dephosphorylate tyrosine residues; and (3) dual specificity protein phosphatases which dephosphorylate serine, threonine and tyrosine residues.

Serine/threonine protein phosphatases are associated with the regulation of cholesterol biosynthesis, glycogen metabolism, muscle contractility, calcium ion channels, protein synthesis, regulation of the G2 to M transition of the cell cycle, regulation of glycolysis (6-phosphofructo-2-kinase and pyruvate kinase), glycogenolysis (phosphorylase kinase subunit), gluconeogenesis (fructose-2,6-bisphosphatase and pyruvate kinase), amino-acid degradation (phenylalanine hydroxylase), lipid metabolism (acetyl-CoA carboxylase), catecholamine synthesis (tyrosine hydroxylase) and protein synthesis (elongation factor 2).

Protein tyrosine phosphatases (PTPs) are a family of intracellular and integral membrane phosphatases that dephosphorylate tyrosine residues in proteins. PTPs have been identified in mammals, Drosophila and *Schiz. pombe* and are implicated in the control of normal and neoplastic growth and proliferation. They have also been found encoded by plasmids in bacteria of the genus Yersinia, where they are implicated in pathogenicity.

Dual specificity phosphatases hydrolyze phosphotyrosine, phosphothreonine, and phosphoserine residues (for a review, see, e.g., Fauman and Saper (1996) *Trends in Biochem.* 21:412). This class of proteins is exemplified by the VH1 or vaccinia virus late HI gene protein, whose catalytic activity is required for vaccinia virus replication. A human homolog of VH1, VHR, has also been identified. VH1-like dual specificity phosphatase can also include the phosphatases PAC-1 and CL100/MKP-1, hVH-2/MKP-2, hVH-3, MKP-3, MKP-X, MKP-4, hVH-5, and M3/6 proteins. The PAC-1 and CL100 proteins hydrolyze phosphothreonine and phosphotyrosine residues on phosphorylated MAP (mitogen activated protein) kinases. In order to modulate signalling events, the activity and expression of dual specificity phosphatases can be finely regulated. For example, the PAC-1 and CL100 phosphatase can be induced by growth factors (Keyse, S (1995) *Biochim. Biophys. Acta* 1265:152–160).

Thus, the function of dual specificity phosphatase proteins can be critical for the regulation of cellular processes such as proliferation and differentiation. Given the important biological roles and properties of phosphatases, there exists a need for the identification of novel genes encoding such proteins as well as for the discovery of modulators of such molecules for use in regulating a variety of normal and/or pathological cellular processes.

SUMMARY OF THE INVENTION

The present invention is based, in part, on the discovery of novel dual specificity phosphatases, referred to herein as "21117" or "38692" nucleic acid and protein molecules. The nucleotide sequence of cDNAs encoding 21117 and 38692 are shown in SEQ ID NOs:1 and 4, respectively and the amino acid sequences of 21117 and 38692 polypeptides are shown in SEQ ID NOs:2 and 5, respectively. In addition, the nucleotide sequence of the 21117 and 38692 coding regions are depicted in SEQ ID NOs:3 and 6, respectively.

Accordingly, in one aspect, the invention features a nucleic acid molecule that encodes a 21117 or 38692 protein or polypeptide, e.g., a biologically active portion of the 21117 or 38692 protein. In a preferred embodiment, the isolated nucleic acid molecule encodes a polypeptide having the amino acid sequence of SEQ ID NO:2 or SEQ ID NO:5. In other embodiments, the invention provides isolated 21117 or 38692 nucleic acid molecules having the nucleotide sequence shown in SEQ ID NO:1, SEQ ID NO:3, SEQ ID NO:4, or SEQ ID NO:6. In still other embodiments, the invention provides nucleic acid molecules that are substantially identical (e.g., naturally occurring allelic variants) to the nucleotide sequence shown in SEQ ID NO:1, SEQ ID NO:3, SEQ ID NO:4, or SEQ ID NO:6. In other embodiments, the invention provides a nucleic acid molecule that hybridizes under a stringent hybridization condition as described herein to a nucleic acid molecule comprising the nucleotide sequence of SEQ ID NO: 1, 3, 4, or 6, wherein the nucleic acid encodes a full length 21117 or 38692 protein or an active fragment thereof.

In a related aspect, the invention further provides nucleic acid constructs that include the 21117 or 38692 nucleic acid molecules described herein. In certain embodiments, the nucleic acid molecules of the invention are operatively linked to native or heterologous regulatory sequences. Also included are vectors and host cells containing the 21117 or 38692 nucleic acid molecules of the invention, e.g., vectors and host cells suitable for producing 21117 or 38692 nucleic acid molecules and polypeptides.

In another related aspect, the invention provides nucleic acid fragments suitable as primers or hybridization probes for the detection of 21117 or 38692-encoding nucleic acids.

In a preferred embodiment, a nucleic acid fragment includes at least one, two and preferably more, nucleotides from the sequence of nucleotide 1 to 2985 of SEQ ID NO:1.

In a preferred embodiment, a nucleic acid fragment includes at least one, preferably more, nucleotides from the sequence of nucleotides 1 to 432 of SEQ ID NO:4, or nucleotides 850 to 1114 of SEQ ID NO:4.

In still another related aspect, isolated nucleic acid molecules that are antisense to a 21117 or 38692 encoding nucleic acid molecule are provided.

In another aspect, the invention features 21117 or 38692 polypeptides and biologically active or antigenic fragments thereof that are useful, e.g., as reagents or targets in assays applicable to treatment and diagnosis of 21117 or 38692 mediated or related disorders, e.g., liver or hematopoietic cell associated disorders. In another embodiment, the invention provides 21117 or 38692 polypeptides having a 21117 or 38692 activity. Preferred polypeptides are 21117 or 38692 proteins including at least one dual specificity phosphatase catalytic domain, and, preferably, having a 21117 or 38692 activity, e.g., a 21117 or 38692 activity as described herein.

In other embodiments, the invention provides 21117 or 38692 polypeptides, e.g., a 21117 or 38692 polypeptide having the amino acid sequence shown in SEQ ID NO:2 or SEQ ID NO:5; an amino acid sequence that is substantially identical to the amino acid sequence shown in SEQ ID NOs:2 or 5; or an amino acid sequence encoded by a nucleic acid molecule having a nucleotide sequence that hybridizes under a stringent hybridization condition as described herein to a nucleic acid molecule comprising the nucleotide sequence of SEQ ID NOs:1, 3, 4, 6, wherein the nucleic acid encodes a full length 21117 or 38692 protein or an active fragment thereof.

In a related aspect, the invention provides 21117 or 38692 polypeptides or fragments operatively linked to non-21117 or 38692 polypeptides to form fusion proteins.

In another aspect, the invention features antibodies and antigen-binding fragments thereof, that react with, or more preferably, specifically bind 21117 or 38692 polypeptides.

In another aspect, the invention provides methods of screening for compounds that modulate the expression or activity of the 21117 or 38692 polypeptides or nucleic acids.

In still another aspect, the invention provides a process for modulating 21117 or 38692 polypeptide or nucleic acid expression or activity, e.g. using the screened compounds. In certain embodiments, the methods involve treatment of conditions related to aberrant (e.g., decreased) activity or expression of the 21117 or 38692 polypeptides or nucleic acids, such as conditions involving aberrant cellular proliferation of a 21117- or 38692-expressing cell, e.g., a breast, colon, lung, or adipose cell, a liver cell, bone, endothelial cell, or a hematopoeitic cell (e.g., a myeloid (neutrophil) cell, a monocyte, an erythroid cell, a bone marrow cell, a CD34-expressing cell, a megakaryocyte). The condition may involve increased hematopoeitic cell activity or proliferation as in the case of leukemia, e.g., an erythroleukemia; or decreased hematopoietic cell differentiation as in the case of, e.g., an anemia.

In still another aspect, the invention features a method of modulating (e.g., enhancing or inhibiting) the proliferation, survival, migration, and/or differentiation of a cell, e.g., a 21117 or 38692-expressing cell, e.g., a breast, colon, lung, or adipose cell, a bone cell, an endothelial cell, a liver cell, or a hematopoietic cell (e.g., a myeloid (neutrophil) cell, a monocyte, an erythroid cell, a bone marrow cell, a CD34-expressing cell, a megakaryocyte). The method includes contacting the cell with an agent that modulates the activity or expression of a 21117 or 38692 polypeptide or nucleic acid, in an amount effective to modulate the proliferation, survival, migration, and/or differentiation of the cell.

In a preferred embodiment, the 21117 or 38692 polypeptide has an amino acid sequence identical to, or substantially identical to, SEQ ID NO:2 or SEQ ID NO:5. In other embodiments, the 21117 or 38692 polypeptide is a fragment of at least 15, 20, 50, 100, 150, 180, 200, or more contiguous amino acids of SEQ ID NO:2 or SEQ ID NO:5.

In a preferred embodiment, the 21117 or 38692 nucleic acid has a nucleotide sequence identical to, or substantially identical to, SEQ ID NO:1, 3, 4, or 6. In other embodiments, the 21117 or 38692 nucleic acid is a fragment of at least 50, 100, 150, 200, 250, 300, 350, 400, 450, 500, 550, 600, or more contiguous nucleotides of SEQ ID NO:1, 3, 4, or 6.

In a preferred embodiment, the agent modulates (e.g., increases or decreases) protein phosphatase activity. In other embodiments, the agent modulates (e.g., increases or decreases) expression of the 21117 or 38692 nucleic acid by, e.g., modulating transcription, mRNA stability, etc.

In preferred embodiments, the agent is a peptide, a phosphopeptide, a small molecule, e.g., a member of a combinatorial library, or an antibody, or any combination thereof. The antibody can be conjugated to a therapeutic moiety selected from the group consisting of a cytotoxin, a cytotoxic agent and a radioactive metal ion.

In additional preferred embodiments, the agent is an antisense, a ribozyme, or a triple helix molecule, or a 21117 or 38692 nucleic acid, or any combination thereof.

In a preferred embodiment, the agent is administered in combination with a cytotoxic agent.

In a preferred embodiment, the cell, e.g., the 21117 or 38692-expressing cell, is a breast, colon, bone, endothelial, liver, lung, or an adipose cell.

In a preferred embodiment, the cell, e.g., the 21117 or 38692-expressing cell, is a hematopoietic cell, e.g., a myeloid, lymphoid or erythroid cell, or a precursor cell thereof. In other preferred embodiments, the cell, e.g., the 21117 or 38692-expressing cell, is a bone marrow erythroid cell, e.g., an erythroid progenitor (e.g., a GPA(low)CD71+ cell) or a differentiated cell, e.g., an erythrocyte or a megakaryocyte.

In a preferred embodiment, the cell, e.g., the 21117 or 38692-expressing cell, is further contacted with a protein, e.g., a cytokine. Preferably, the protein is selected from the group consisting of G-CSF, GM-CSF, stem cell factor, and erythropoietin. The protein contacting step can occur before, at the same time, or after the agent is contacted. The protein contacting step can be effected in vitro or ex vivo. For example, the cell, e.g., the 21117 or 38692-expressing cell is obtained from a subject, e.g., a patient, and contacted with the protein ex vivo. The treated cell can be re-introduced into the subject. Alternatively, the protein contacting step can occur in vivo.

In a preferred embodiment, the agent and the 21117 or 38692-polypeptide or nucleic acid are contacted in vitro or ex vivo.

In a preferred embodiment, the contacting step is effected in vivo in a subject, e.g., as part of a therapeutic or prophylactic protocol. Preferably, the subject is a human, e.g., a patient with a hematopoietic disorder or an erythroid-associated disorder. In other embodiments, the subject is a non-human animal, e.g., an experimental animal.

The contacting step(s) can be repeated.

In a preferred embodiment, the agent decreases the proliferation and/or enhances the differentiation of the cell, e.g., the 21117 or 38692-expressing cell (e.g., the hematopoietic cell, e.g., the myeloid (neutrophil) cell, the monocyte, the erythroid cell, the bone marrow cell, the CD34-expressing cell, or the megakaryocyte cell). Such agents can be used to treat or prevent cancers, e.g., leukemic cancers.

In a preferred embodiment, the agent increases the number of hematopoietic cells (e.g., myeloid (neutrophil) cells, monocytes, erythroid cells, bone marrow cells, CD34-expressing cells, megakaryocytes), by e.g., increasing the proliferation, survival, and/or stimulating the differentiation, of progenitor cells. Such agents can be used to treat or prevent hematopoietic or erythroid cell-associated disorders.

In another aspect, the invention features a method of modulating hematopoiesis, e.g., erythropoiesis, comprising contacting a 21117 or 38692-expressing cell hematopoietic cell (e.g., a myeloid (neutrophil) cell, a monocyte, an erythroid cell, a bone marrow cell, a CD34-expressing cell, a megakaryocyte), with an agent that increases or decreases the activity or expression of a 21117 or 38692 polypeptide, e.g., a polypeptide as described herein, or nucleic acid, e.g., a nucleic acid as described herein, thereby modulating the differentiation of the hematopoietic cell.

In a preferred embodiment, the agent modulates (e.g., increases or decreases) protein phosphatase activity.

In preferred embodiments, the agent is a peptide, a phosphopeptide, a small molecule, e.g., a member of a combinatorial library, or an antibody, or any combination thereof. The antibody can be conjugated to a therapeutic moiety selected from the group consisting of a cytotoxin, a cytotoxic agent and a radioactive metal ion.

In additional preferred embodiments, the agent is an antisense, a ribozyme, or a triple helix molecule, or a 21117 or 38692 nucleic acid, or any combination thereof. In another embodiment, the agent is administered in combination with a cytotoxic agent.

In a preferred embodiment, the hematopoeitic cell is a bone marrow cell, e.g., a CD34-expressing cell, an erythroid cell, e.g., an erythroid progenitor or differentiated cell, e.g., an erythrocyte or a megakaryocyte; or a liver cell.

In a preferred embodiment, the agent and the 21117 or 38692-polypeptide or nucleic acid are contacted in vitro or ex vivo.

In a preferred embodiment, the contacting step is effected in vivo in a subject, e.g., as part of a therapeutic or prophylactic protocol. In one embodiment, the subject is a patient at risk, or having a disording involving aberrant activity of a cell or tissue where a 21117- or 38692 molecule is expressed. For example, the subject is a human, e.g., a patient with a hematopoietic disorder or an erythroid-associated disorder. Alternatively, the subject can be a cancer patient, e.g., a patient with leukemic cancer. In other embodiments, the subject is a non-human animal, e.g., an experimental animal.

In a preferred embodiment, the method further includes contacting of the erythroid cell with a protein, e.g., a cytokine. Preferably, the protein is selected from the group consisting of G-CSF, GM-CSF, stem cell factor, and erythropoietin. The protein contacting step can occur before, at the same time, or after the agent is contacted. The protein contacting step can be effected in vitro or ex vivo. For example, the cell, e.g., the erythroid cell can be obtained from a subject, e.g., a patient, and contacted with the protein ex vivo. The treated cell can be re-introduced into the subject. Alternatively, the protein contacting step can occur in vivo.

The contacting step(s) can be repeated.

In a preferred embodiment, the agent increases the number of hematopoietic cells, e.g., erythroid cells, by e.g., increasing the proliferation, survival, and/or stimulating the differentiation, of hematopoietic (e.g., eythroid) progenitor cells, in the subject.

In yet another aspect, the invention features a method of treating or preventing a disorder involving aberrant expression or activity of a 21117- or a 38692 nucleic acid or polypeptide, in a subject. The method includes administering to the subject an effective amount of an agent that modulates the activity or expression of a 21117 or 38692 polypeptide or nucleic acid such that the disorder is ameliorated or prevented.

In a preferred embodiment, the 21117 or 38692 polypeptide has an amino acid sequence identical to, or substantially identical to, SEQ ID NO:2 or SEQ ID NO:5. In other embodiments, the 21117 or 38692 polypeptide is a fragment of at least 15, 20, 50, 100, 150, 180, 200, or more contiguous amino acids of SEQ ID NO:2 or SEQ ID NO:5.

In a preferred embodiment, the 21117 or 38692 nucleic acid has a nucleotide sequence identical to, or substantially identical to, SEQ ID NO:1, 3, 4, or 6. In other embodiments, the 21117 or 38692 nucleic acid is a fragment of at least 50, 100, 150, 200, 250, 300, 350, 400, 450, 500, 550, 600, or more contiguous nucleotides of SEQ ID NO:1, 3, 4, or 6.

In a preferred embodiment, the agent modulates (e.g., increases or decreases) protein phosphatase activity.

In a preferred embodiment, the agent modulates (e.g., increases or decreases) expression of the 21117 or 38692 nucleic acid by, e.g., modulating transcription, mRNA stability, etc.

In preferred embodiments, the agent is a peptide, a phosphopeptide, a small molecule, e.g., a member of a combinatorial library, or an antibody, or any combination thereof. The antibody can be conjugated to a therapeutic moiety selected from the group consisting of a cytotoxin, a cytotoxic agent and a radioactive metal ion.

In additional preferred embodiments, the agent is an antisense, a ribozyme, or a triple helix molecule, or a 21117 or 38692 nucleic acid, or any combination thereof.

In a preferred embodiment, the agent is administered in combination with a cytotoxic agent.

In a preferred embodiment, the subject is a human, e.g., a patient with a immune or a cancer disorder. In other embodiments, the subject is a non-human animal, e.g., an experimental animal.

In a preferred embodiment, the disorder is a disorder associated with aberrant activity of a cell in which a 21117 or 38692 molecule is expressed, e.g., a disorder involving aberrant activity or expression of a cell e.g., a breast, colon, lung, or adipose cell, a liver cell, bone, endothelial cell, or a hematopoeitic cell (e.g., a myeloid (neutrophil) cell, a monocyte, an erythroid cell, a bone marrow cell, a CD34-expressing cell, a megakaryocyte).

In a preferred embodiment, the disorder is a hematopoietic disorder or an erythroid-associated disorder.

In a preferred embodiment, the disorder is a cancer, e.g., leukemic cancer, a carcinoma, sarcoma or a metastatic cancer.

In a preferred embodiment, the agent decreases the proliferation and/or enhances the differentiation of a cell, e.g., a 21117 or 38692-expressing cell, e.g., a hematopoeitic cell (e.g., a myeloid (neutrophil) cell, a monocyte, an erythroid cell, a bone marrow cell, a CD34-expressing cell, a megakaryocyte), in the subject. Such agents can be used to treat or prevent cancers, e.g., leukemic cancers such as erythroid leukemias, or carcinomas, sarcomas or metastatic cancers.

In a preferred embodiment, the agent increases the number of a 21117 or 38692-expressing cells, e.g., hematopoietic cells (e.g., erythroid, myeloid, monocyte, or megakaryocyte cells), by e.g., increasing the proliferation, and/or stimulating the differentiation, of progenitor cells, in the subject.

In a preferred embodiment, the method further includes administering an effective amount of a protein, e.g., a cytokine. Preferably, the protein is selected from the group consisting of G-CSF, GM-CSF, stem cell factor, and erythropoietin to the subject. Preferably, the protein is erythropoietin. The protein can be administered before, at the same time or after, administration of the agent.

The administration of the agent and/or protein can be repeated.

In still another aspect, the invention features a method for evaluating the efficacy of a treatment of a disorder, in a subject. The method includes treating a subject with a protocol under evaluation; assessing the expression of a 21117 or 38692 nucleic acid or 21117 or 38692 polypeptide, such that a change in the level of 21117 or 38692 nucleic acid or 21117 or 38692 polypeptide after treatment, relative to the level before treatment, is indicative of the efficacy of the treatment of the disorder.

In a preferred embodiment, the subject is a human. In other embodiments, the subject is an experimental animal, e.g., an animal model for a hematopoietic- (e.g., an erythroid-) associated disorder, a cancer disorder, or an endothelial cell disorder.

In a preferred embodiment, the method can further include treating the subject with a protein, e.g., a cytokine. Preferably, the protein is selected from the group consisting of G-CSF, GM-CSF, stem cell factor, and erythropoietin prior to assessing expression levels. Preferably, the protein is erythropoietin.

The invention also features a method of diagnosing, or staging, a disorder involving aberrant activity or expression of a 21117 or 38692 nucleic acid or a 21117 or 38692 polypeptide. The method includes evaluating the expression or activity of a 21117 or 38692 nucleic acid or a 21117 or 38692 polypeptide, such that, a difference in the level of 21117 or 38692 nucleic acid or 21117 or 38692 polypeptide relative to a normal subject or a cohort of normal subjects is indicative of the disorder.

In a preferred embodiment, the subject is a human.

In a preferred embodiment, the evaluating step occurs in vitro or ex vivo. For example, a sample, e.g., a blood sample, a biopsy, is obtained from the subject.

In a preferred embodiment, the evaluating step occurs in vivo. For example, by administering to the subject a detectably labeled agent that interacts with the 21117 or 38692 nucleic acid or polypeptide, such that a signal is generated relative to the level of activity or expression of the 21117 or 38692 nucleic acid or polypeptide.

In a preferred embodiment, the disorder is a cancer, or a hematopoietic disorder, e.g., a hematopoietic or an erythroid associated disorder, as described herein.

The invention also provides assays for determining the activity of or the presence or absence of 21117 or 38692 polypeptides or nucleic acid molecules in a biological sample, including for disease diagnosis.

In further aspect, the invention provides assays for determining the presence or absence of a genetic alteration in a 21117 or 38692 polypeptide or nucleic acid molecule, including for disease diagnosis.

In yet another aspect, the invention features a method for identifying an agent, e.g., a compound, which modulates the activity of a 21117 or 38692 polypeptide, e.g., a 21117 or 38692 polypeptide as described herein, or the expression of a 21117 or 38692 nucleic acid, e.g., a 21117 or 38692 nucleic acid as described herein, including contacting the 21117 or 38692 polypeptide or nucleic acid with a test agent (e.g., a test compound); and determining the effect of the test compound on the activity of the polypeptide or nucleic acid to thereby identify a compound which modulates the activity of the polypeptide or nucleic acid.

In a preferred embodiment, the activity of the 21117 or 38692 polypeptide is protein phosphatase activity.

In a preferred embodiment, the activity of the 21117 or 38692 polypeptide is proliferation, differentiation, migration, and/or survival of a cell, e.g., a 21117 or 38692-expressing cell, e.g., a breast, colon, lung, or adipose cell, a bone cell, an endothelial cell, a liver cell, or a hematopoietic cell (e.g., a myeloid (neutrophil) cell, a monocyte, an erythroid cell, a bone marrow cell, a CD34-expressing cell, a megakaryocyte).

In preferred embodiments, the agent is a peptide, a phosphopeptide, a small molecule, e.g., a member of a combinatorial library, or an antibody, or any combination thereof.

In additional preferred embodiments, the agent is an antisense, a ribozyme, or a triple helix molecule, or a 21117 or 38692 nucleic acid, or any combination thereof.

In another aspect, the invention features a two dimensional array having a plurality of addresses, each address of the plurality being positionally distinguishable from each other address of the plurality, and each address of the plurality having a unique capture probe, e.g., a nucleic acid or peptide sequence. At least one address of the plurality has a capture probe that recognizes a 21117 or 38692 molecule. In one embodiment, the capture probe is a nucleic acid, e.g., a probe complementary to a 21117 or 38692 nucleic acid sequence. In another embodiment, the capture probe is a polypeptide, e.g., an antibody specific for 21117 or 38692 polypeptides. Also featured is a method of analyzing a sample by contacting the sample to the aforementioned array and detecting binding of the sample to the array.

Other features and advantages of the invention will be apparent from the following detailed description, and from the claims.

BRIEF DESCRIPTION OF THE DRAWINGS

FIGS. 1A–1D depicts a cDNA sequence (SEQ ID NO:1) and predicted amino acid sequence (SEQ ID NO:2) of human 21117. The methionine-initiated open reading frame of human 21117 (without the 5' and 3' untranslated regions) starts at nucleotide 589 and ends at nucleotide 2586 of SEQ ID NO:1 (shown also as coding sequence (SEQ ID NO:3)).

FIG. 2 depicts a hydropathy plot of human 21117. Relative hydrophobic residues are shown above the dashed horizontal line, and relative hydrophilic residues are below the dashed horizontal line. The cysteine residues (cys) are indicated by short vertical lines just below the hydropathy trace. The numbers corresponding to the amino acid sequence of human 21117 are indicated. Polypeptides of the invention include 21117 fragments that include: all or part of a hydrophobic sequence (a sequence above the dashed line, e.g., all or part of the sequence from about residue 91 to about residue 106); and/or all or part of a hydrophilic fragment (e.g., a fragment below the dashed line such as from about residue 592 to about residue 633). Other fragments include a cysteine residue or a glycosylation site.

FIG. 3A depicts alignment of a dual specificity phosphatase catalytic domain (DSPc) with human 21117 amino acid sequence, with a consensus amino acid sequence derived from a hidden Markov model. The upper sequence is the consensus amino acid sequence (SEQ ID NO:7), while the lower amino acid sequence corresponds to amino acids 158–297 of SEQ ID NO:2. FIG. 3B depicts alignment of a dual specificity phosphatase catalytic domain (dsp_5) (SEQ ID NO:8) with amino acids 158 to 297 of 21117 (SEQ ID NO:2).

FIG. 4A depicts alignment of a rhodanese domain with human 21117 amino acid sequence, with a consensus amino acid sequence derived from a hidden Markov model. The upper sequence is the consensus amino acid sequence (SEQ ID NO:9), while the lower amino acid sequence corresponds to amino acids 11 to 131 of SEQ ID NO:2. FIG. 4B depicts alignment of a rhodanese domain (SEQ ID NO:10) with amino acids 12 to 134 of 21117 (SEQ ID NO:2).

FIGS. 6A–B depicts a cDNA sequence (SEQ ID NO:4) and predicted amino acid sequence (SEQ ID NO:5) of human 38692. The methionine-initiated open reading frame of human 38692 (without the 5' and 3' untranslated regions) starts at nucleotide 89 and ends at nucleotide 760 of SEQ ID NO:4 (shown also as coding sequence (SEQ ID NO:6)).

FIG. 8A depicts alignment of a DSPc domain with human 38692 amino acid sequence, with a consensus amino acid sequence derived from a hidden Markov model. The upper sequence is the consensus amino acid sequence (SEQ ID NO:7), while the lower amino acid sequence corresponds to amino acids 28 to 173 of SEQ ID NO:5. FIG. 8B depicts alignment of a dsp_5 domain (SEQ ID NO:8) with amino acids 28 to 173 of 38692 (SEQ ID NO:5).

Figure 5:
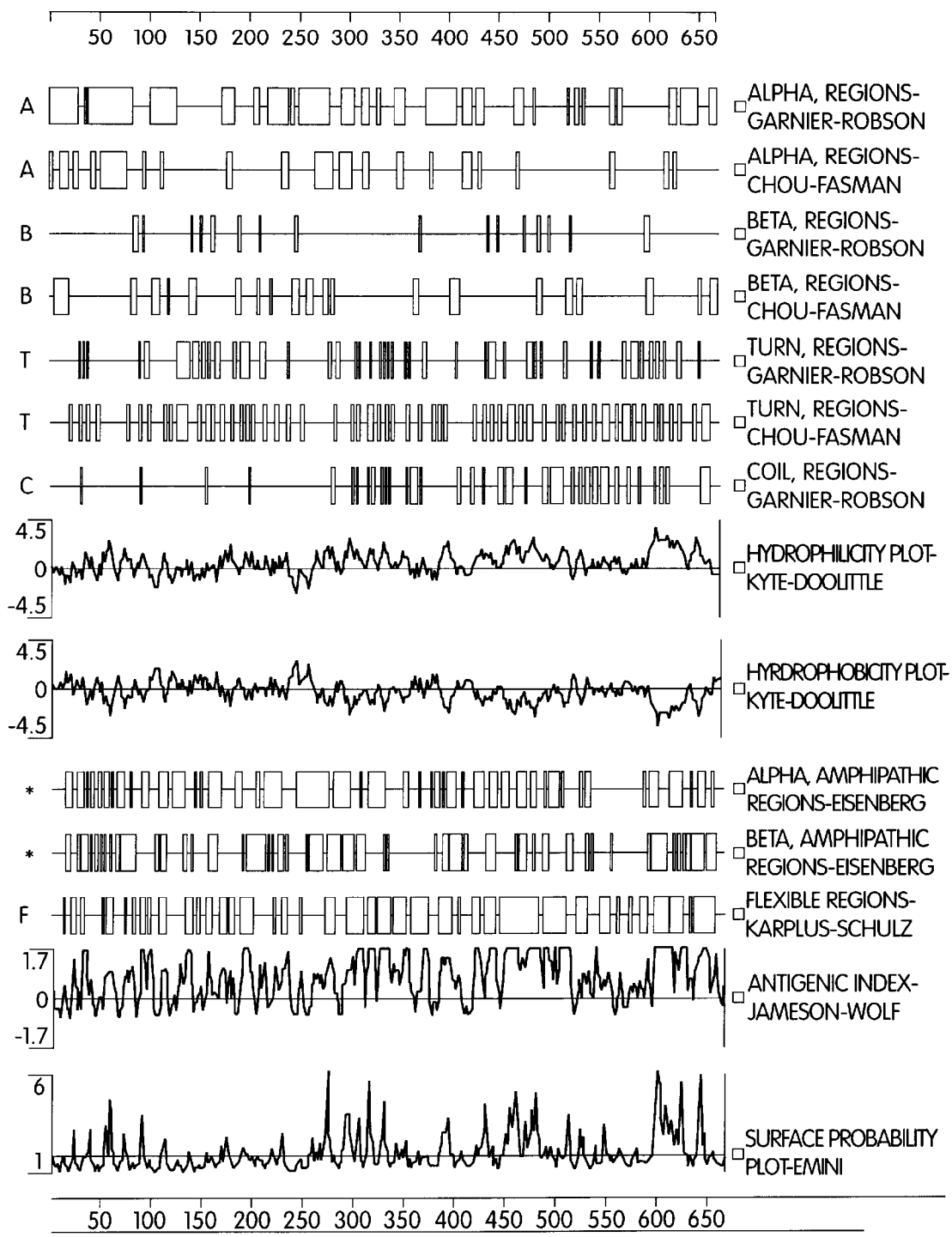
FIG. 5 depicts a series of plots summarizing an analysis of the primary and secondary protein structure of human 21117. The particular algorithm used for each plot is indicated at the right hand side of each plot. The following plots are depicted: Garnier-Robson plots providing the predicted location of alpha-, beta-, turn and coil regions (Garnier et al. (1978) *J. Mol. Biol.* 120:97); Chou-Fasman plots providing the predicted location of alpha-, beta-, turn and coil regions (Chou and Fasman (1978) *Adv. In Enzymol. Mol.* 47:45–148); Kyte-Doolittle hydrophilicity/hydrophobicity plots (Kyte and Doolittle (1982) *J. Mol. Biol.* 157:105–132); Eisenberg plots providing the predicted location of alpha- and beta-amphipathic regions (Eisenberg et al. (1982) *Nature* 299:371–374); a Karplus-Schultz plot providing the predicted location of flexible regions (Karplus and Schulz (1985) *Naturwissens-Chafen* 72:212–213); a plot of the antigenic index (Jameson-Wolf) (Jameson and Wolf (1988) *CABIOS* 4:121–136); and a surface probability plot (Emini algorithm) (Emini et al. (1985) *J. Virol.* 55:836–839). The numbers corresponding to the amino acid sequence of human 21117 are indicated. Polypeptide fragments of the invention include polypeptides which have all or part of any of the regions described in this figure. Also included are variants having a mutation in a selected region shown in this figure.
Figure 7:
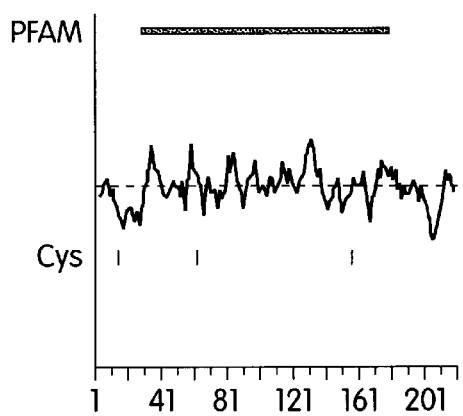
FIG. 7 depicts a hydropathy plot of human 38692. The numbers corresponding to the amino acid sequence of human 38692 are indicated. Polypeptides of the invention include 38692 fragments that include: all or part of a hydrophobic sequence (a sequence above the dashed line, e.g., all or part of the sequence from about residue 31 to about residue 41); and/or all or part of a hydrophilic fragment (e.g., a fragment below the dashed line such as from about residue 200 to about residue 212). Other fragments include cysteine residues.
Figure 9:
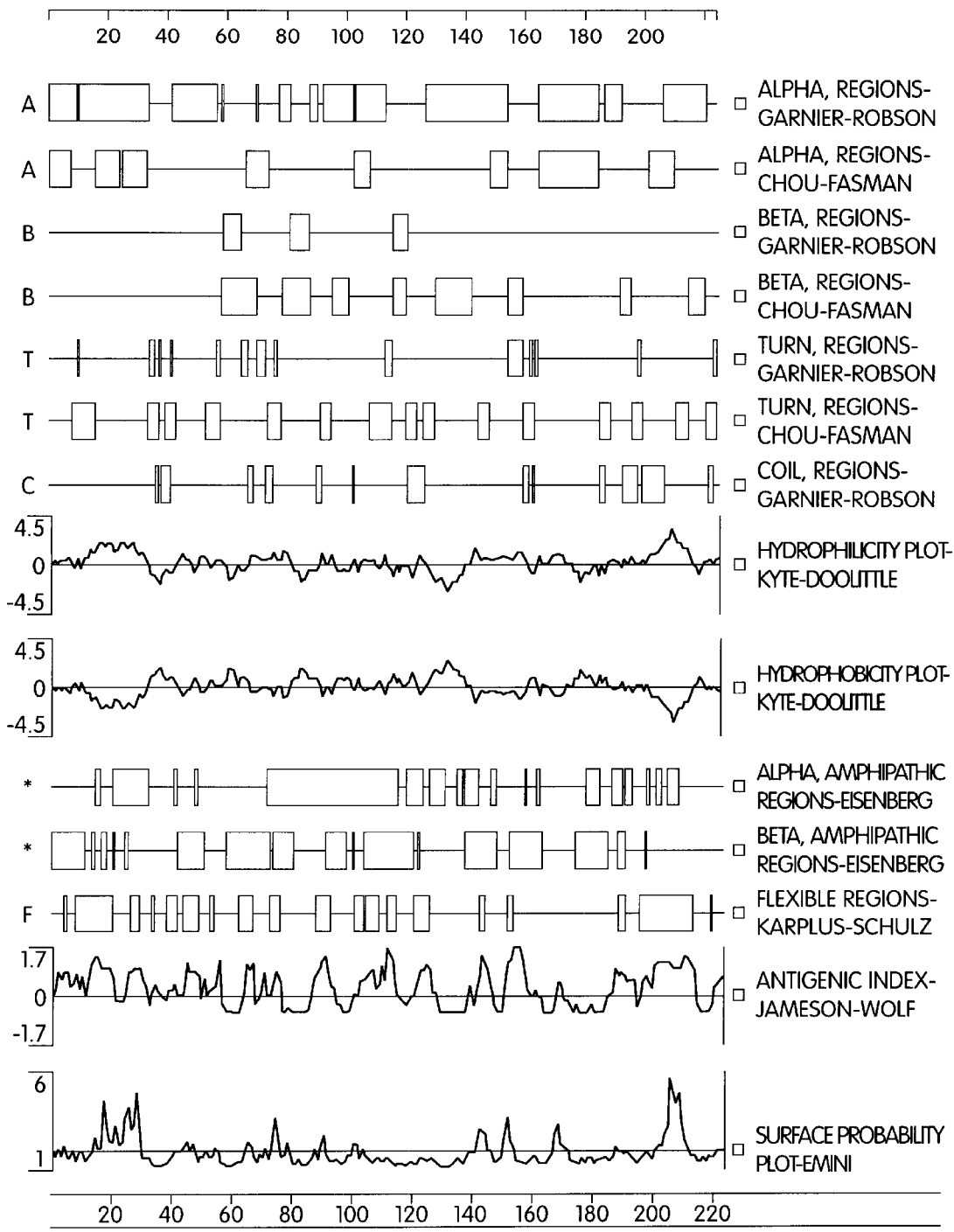
FIG. 9 depicts a series of plots summarizing an analysis of the primary and secondary protein structure of human 38692. The particular algorithm used for each plot is indicated at the right hand side of each plot. See legend of FIG. 5 for a description of the plots. The numbers corresponding to the amino acid sequence of human 38692 are indicated.

mBM CD15+/CD11b+LP15-2; (28) BM CD15+/CD11b-LF80-4; (29) BM CD15+/CD11b-LP23-2;(30)BM CD15+/CD34-LP27-2; (31) BM CD15+/CD34-LP41-1; (32) Erythrocyte (Ery) d6 LP25-1; (33) Ery d6 LP31-1; (34) Ery d10 LP24-4; (35) Ery d12 LF24-8; (36) Ery d12 LF24-9; (37) Ery d14 GPA+LP31-4; (38) Ery d14 CD36+LP31-7; (39) Megakaryocyte (Meg) 24hr LF23-2; (40) Meg 44hr LF6-2; (41) Meg d7 LP31-2; (42) Meg d12 LF26; (43) Meg d14 LP31-5; (44) Neutrophil d4 LF30; (45) Neutrophil d6 LF26; (46) Neutrophil d6 LP27; (47) Neutrophil d7 LP31-3; (48) Neutrophil d12 LP27; (49) Neutrophil d12 LP26B; (50) Neutroph d14 LP31-6. High relative levels of expression were found in fetal liver cells, fetal liver CD34+ cells, Bone Marrow Glycophorin A (BM GPA) low CD71+LF38; and BM GPA low CD71+LP85-2.

DETAILED DESCRIPTION

Human 21117

The human 21117 sequence (FIG. 1; SEQ ID NO:1), which is approximately 3544 nucleotides long including untranslated regions, contains a predicted methionine-initiated coding sequence of about 1998 nucleotides (nucleotides 589 to 2586 of SEQ ID NO:1; SEQ ID NO:3). The coding sequence encodes a 666 amino acid protein (SEQ ID NO:2).

Human 21117 contains the following regions or other structural features: a dual specificity phosphatase, catalytic domain (PF00782) located from about amino acid residue 158 to 297 of SEQ ID NO:2; a rhodanese-like domain (PF00581) located from about amino acid residue 11 to 131 of SEQ ID NO:2; and one tyrosine specific protein phosphatase active site (PS00383) at amino acids 242 to 254 of SEQ ID NO:2.

The 21117 protein additionally includes: six predicted N-glycosylation sites (PS00001) at amino acids 38 to 41, 49 to 52, 190 to 193, 212 to 215, 300 to 303, and 640 to 643 of SEQ ID NO:2; two predicted cAMP and cGMP-dependent protein kinase phosphorylation sites (PS00004) at amino acids 277 to 280 and 624 to 627 of SEQ ID NO:2; 12 predicted Protein Kinase C sites (PS00005) at about amino acids 12 to 14, 23 to 25, 72 to 74, 82 to 84, 393 to 395, 439 to 441, 473 to 475, 481 to 483, 486 to 488, 596 to 598, 604 to 606, and 609 to 611 of SEQ ID NO:2; 13 casein kinase II phosphorylation sites (PS00006) at amino acids 21 to 24, 91 to 94, 214 to 217, 266 to 269, 369 to 372, 421 to 424, 434 to 437, 458 to 461, 508 to 511, 589 to 592, 612 to 615, 617 to 620, and 642 to 645 of SEQ ID NO:2; and seven predicted N-myristoylation sites (PS00008) from about amino acid 134 to 139, 247 to 252, 329 to 334, 382 to 387, 520 to 525, 574 to 579, and 650 to 655 of SEQ ID NO:2.

Human 38692

The human 38692 sequence (FIG. 6; SEQ ID NO:4), which is approximately 1114 nucleotides long including untranslated regions, contains a predicted methionine-initiated coding sequence of about 672 nucleotides (nucleotides 89 to 760 of SEQ ID NO:4; SEQ ID NO:6). The coding sequence encodes a 223 amino acid protein (SEQ ID NO:5).

Human 38692 contains the following regions or other structural features: a dual specificity phosphatase, catalytic domain (PF00782) located from about amino acid residue 28 to 173 of SEQ ID NO:5; one predicted Protein Kinase C phosphorylation site (PS00005) at about amino acids 201 to 203 of SEQ ID NO:5; one predicted casein kinase II phosphorylation site (PS0006) at amino acids 205 to 208 of SEQ ID NO:5; two predicted N-myristoylation sites (PS00008) from about amino acid 123 to 128 and 197 to 202 of SEQ ID NO:5; and two tyrosine kinase phosphorylation sites (PS00007) at amino acids 15 to 23 and 142 to 149 of SEQ ID NO:5.

For general information regarding PFAM identitiers, PS prefix and PF prefix domain identification numbers, refer to Sonnhammer et al. (1997) *Protein* 28:405–420.

The 21117 and 38692 proteins contains a significant number of structural characteristics in common with members of the dual specificity phosphatase family. The term "family" when referring to the protein and nucleic acid molecules of the invention means two or more proteins or nucleic acid molecules having a common structural domain or motif and having sufficient amino acid or nucleotide sequence homology as defined herein. Such family members can be naturally or non-naturally occurring and can be from either the same or different species. For example, a family can contain a first protein of human origin as well as other distinct proteins of human origin, or alternatively, can contain homologues of non-human origin, e.g., rat or mouse proteins. Members of a family can also have common functional characteristics.

Dual specificity phosphatase proteins are characterized by a common fold. Examples of members of the dual specificity phosphatase family include MAP kinase phosphatase-1 (MKP-1), which dephosphorylates MAP kinase on both threonine and tyrosine residues and a human, vaccinia H1-related phosphatase (VHR), which also removes the phosphate from phosphothreonine and phosphotyrosine residues. Dual specificity phosphatases are exemplified by the VH1 or vaccinia virus late H1 gene protein, which hydrolyzes both phosphotyrosine, phosphothreonine, and phosphoserine. VH1 catalytic activity is required for viral replication. A human homolog of VH1, VHR, has been identified. The three dimensional structure of this family is based on models from x-ray crystallographic data of protein tyrosine phosphatases, and human VHR. The VHR structure includes a core domain consisting of a five-stranded mixed β-sheet and six α-helices. This structure closely superimposes on the structure of phosphotyrosine protein phosphatases. However, dual specificity phosphatases lack the KNRY motif, and the N-terminal structures of tyrosine protein phosphatases which endow these enzymes with a deep active site specific for aryl phosphates. Thus, dual specificity phosphatases have a shallower active site relative to tyrosine protein phosphatases and can accommodate phosphoserine and phosphothreonine substrates. Even so dual specificity phosphatases can have a greater than 50-fold faster rate of phosphatase activity for phosphotyrosine substrates than phosphothreonine or phosphoserine substrates.

Similar to the broader class of phosphatases, dual specificity phosphatases have a highly conserved active site including three catalytic residues, a cysteine, an arginine, and an aspartic acid. The active site cysteine and arginine are found in the "C-$X_5$-R" motif of the tyrosine phosphatase signature (Prosite PS00383). This motif forms a binding pocket for three of the phosphate oxyanions. The cysteine acts as a nucleophile to accept the $PO_3$ group. The reaction transiently generates a phospho-cysteine intermediate before the phosphate is transferred to water. The active site arginine stabilizes the transition-state by hydrogen bonding to phosphate oxygens. In addition the histidine preceding the active site cysteine and the serine or threonine following the active site arginine are responsible for lowering the $pK_a$ of the cysteine to stabilize a negative charge on the cysteine. The active site aspartic acid accelerates the reaction by donating a protein to generate an uncharged hydroxyl (for a review, see Fauman and Saper (1996) *Trends in Biochem.* 21:412). A C-$X_5$-R motif is found in the 21117 protein at about amino acids 242 to 254 of SEQ ID NO:2.

The 21117 and 38692 proteins of the present invention show significant homology to members of the dual specificity phosphatase family. Dual specificity phosphatases are known to play critical roles in growth factor signaling. For example, vaccinia H1-related (VHR)-like phosphatases are known to dephosphorylate growth factor receptors and thereby eliminate their signaling. MAP-kinase phosphatases terminate MAP-kinase activity, thus leading to inhibition of growth factor-mediated mitogenic signaling. Thus, dual specificity phosphatases play a key role in inhibiting proliferation and stimulating the differentiation of cells. As the 21117 and 38692 proteins show homology to dual specificity phosphatases, these proteins are likely to be involved in modulating (e.g., inhibiting) the proliferation and (e.g., stimulating) the differentiation of the cells in which they are expressed, e.g., hematopoietic cells such as eythroid cells, myeloid cells, monocytes, or megakaryocytes. Accordingly, the 21117 and 38692 molecules of the invention may be useful for developing novel diagnostic and therapeutic agents for 21117 and 38692-mediated or related disorders, as described below.

A 21117 or 38692 polypeptide of the invention can include a "dual specificity phosphatase catalytic domain" or regions homologous with a "dual specificity phosphatase catalytic domain". As used herein, the term "dual specificity phosphatase catalytic domain" refers to an amino acid sequence having about 50 to 250, preferably about 100 to 200, more preferably about 120 to 160 amino acid residues and having a bit score for the alignment of the sequence to the dual specificity phosphatase domain (HMM) of at least 50, preferably 100, more preferably 120, 200, or more. The dual specificity phosphatase catalytic domain (HMM) has been assigned the PFAM Accession Number PF00782. Alignments of the dual specificity phosphatase domain (amino acids 158 to 297 of SEQ ID NO:2) of human 21117 with consensus amino acid sequences (SEQ ID NO:7 and SEQ ID NO:8) derived from a hidden Markov model is depicted in FIGS. 3A and 3B. Similar alignments of the dual specificity phosphatase domain (amino acids 28 to 173 of SEQ ID NO:5) of human 38692 with consensus amino acid sequences (SEQ ID NO:7 and SEQ ID NO:8) derived from a hidden Markov model are depicted in FIGS. 8A and 8B.

A dual specificity phosphatase domain preferably includes the conserved active site residues cysteine and arginine in a C-X$_5$-R motif found at about amino acids 242 to 254 of SEQ ID NO:2 (the 21117 protein). Preferably, a dual specificity phosphatase domain includes a conserved general acid, e.g., aspartic acid. For example, a 21117 protein has an aspartic acid located at about residue 213 of SEQ ID NO:2 and a 38692 protein has an aspartic acid located at about residue 89 of SEQ ID NO:5. Typically, dual specificity phosphatases are able to dephosphorylate tyrosine residues and serine/threonine residues.

In a preferred embodiment, a 21117 or 38692 polypeptide or protein has a "dual specificity phosphatase catalytic domain" or a region that includes at least about 50 to 250, preferably about 100 to 200, more preferably about 120 to 160, and even more preferably about 130 to 150 amino acid residues and has at least about 70% 80% 90% 95%, 99%, or 100% homology with a "dual specificity phosphatase catalytic domain," e.g., the dual specificity phosphatase catalytic domain of human 21117 (e.g., residues 158 to 297 of SEQ ID NO:2) or 38692 (e.g., residues 28 to 173 of SEQ ID NO:5).

To identify the presence of a "dual specificity phosphatase catalytic domain" in a 21117 or 38692 protein sequence and to make the determination that a polypeptide or protein of interest has a particular profile, the amino acid sequence of the protein can be searched against a database of HMMs (e.g., the Pfam database, release 2.1) using default parameters. For example, the hmmsf program, which is available as part of the HMMER package of search programs, is a family specific default program for MILPAT0063 and a score of 15 is the default threshold score for determining a hit. Alternatively, the threshold score for determining a hit can be lowered (e.g., to 8 bits). A description of the Pfam database can be found in Sonhammer et al. (1997) *Proteins* 28(3):405–420 and a detailed description of HMMs can be found, for example, in Gribskov et al.(1990) *Meth. Enzymol.* 183:146–159; Gribskov et al.(1987) *Proc. Natl. Acad. Sci. USA* 84:4355–4358; Krogh et al.(1994) *J. Mol. Biol.* 235:1501–1531; and Stultz et al.(1993) *Protein Sci.* 2:305–314, the contents of which are incorporated herein by reference. A search was performed against the HMM database resulting in the identification of a "dual specificity phosphatase catalytic domain" e.g., the dual specificity phosphatase catalytic domain of human 21117 (FIGS. 4A–B) or human 38692 (FIGS. 8A–B).

Human 21117 also contains a "rhodanese-like" domain (PF00581) from about amino acid 11 to 131 of SEQ ID NO:2. The rhodanese-like domain is occasionally found in a single copy in phosphatases, such as Cdc25 phosphatase, a dual-specificity phosphatase. Rhodanese is about 300 amino acids in length and has a conserved domain at the N-terminus and at the C-terminus. A cysteine residue is part of the active site of the enzyme. In a preferred embodiment, a 21117 polypeptide or protein has a "rhodanese-like domain" or a region that includes at least about 80 to 300 amino acids, preferably about 100 to 150 amino acid residues, and has at least about 70% 80% 90% 95%, 99%, or 100% homology with a "rhodanese-like domain," e.g., the rhodanese-like domain of human 21117 (e.g., residues 11 to 131 of SEQ ID NO:2).

As used herein, a "21117 or 38692 activity", "biological activity of 21117 or 38692" or "functional activity of 21117 or 38692", refers to an activity exerted by a 21117 or 38692 protein, polypeptide or nucleic acid molecule on e.g., a 21117 or 38692-responsive cell or on a 21117 or 38692 substrate, e.g., a protein substrate, as determined in vivo or in vitro. In one embodiment, an 21117 or 38692 activity is a direct activity, such as an association with a 21117 or 38692 target molecule. A "target molecule" or "binding partner" is a molecule with which an 21117 or 38692 protein binds or interacts in nature. A 21117 or 38692 activity can also be an indirect activity, e.g., a cellular signaling activity mediated by interaction of the 21117 or 38692 protein with an 21117 or 38692 receptor.

Based on the above-described sequence similarities, the 21117 or 38692 molecules of the present invention are predicted to have similar biological activities as dual specificity phosphatase family members, probably of the VHR-type. Since VHR-phosphatases inhibit growth factor signaling by dephosphorylating, e.g., growth factor receptors, the 21117 or 38692 molecules of the invention are predicted to have one or more of the following activities: (1) catalyze the removal of a phosphate group attached to a tyrosine residue in a protein target, e.g., a growth factor receptor; (2) catalyze the removal of a phosphate group attached to a serine or threonine residue in a protein e.g., a growth factor receptor; (3) modulate growth factor activity; (4) modulate an intracellular signaling pathway, e.g., a MAP kinase or ERK kinase pathway; (5) modulate (e.g., stimulate) cell differentiation, e.g., differentiation of a 38692- or a 21117-expressing cell, e.g., a breast, colon, lung, or adipose cell, a bone cell, an endothelial cell, a liver cell, or a hematopoietic cell (e.g., a myeloid (neutrophil) cell, a monocyte, an erythroid cell, a bone marrow cell, a CD34-expressing cell, a megakaryocyte); (6) stimulate hematopoiesis; (7) modulate cell proliferation, e.g., proliferation of a 38692- or a 21117-expressing cell, e.g., a breast, colon, lung, or adipose cell, a bone cell, an endothelial cell, a liver cell, or a hematopoietic cell (e.g., a myeloid (neutrophil) cell, a monocyte, an erythroid cell, a bone marrow cell, a CD34-expressing cell, a megakaryocyte); (8) inactivate cell surface growth factor receptors, e.g., tyrosine kinase receptors; or (9) modulate apoptosis, of a cell, e.g., a cancer cell, e.g., a leukemic cell.

As 38692 mRNA is found in hematopoietic cells, and in particular, in erythroid cell lineages (FIG. 12), the molecules of the invention can be used to develop novel agents or compounds to treat and/or diagnose disorders involving aberrant activities of those cells e.g., hematopoietic, and in particular, erythroid disorders, as described below. For example, 38692 polypeptide is expressed in megakaryocytes, fetal liver CD34+ cells, erythroid progenitor cells (e.g., bone marrow glycophorin A positive cells (BM GPA+)), and Bone Marrow Glycophorin A (BM GPA) low CD71+.

As used herein, a "CD34-positive cell" refers to a cell that expresses detectable levels of the CD34 antigen, preferably human CD34 antigen. The sequence for human CD34 is provided in SwissProt Accession Number P28906. The CD34 antigen is typically present on immature hematopoietic precursor cells and hematopoietic colony-forming cells in the bone marrow, including unipotent (CFU-GM, BFU-E) and pluripotent progenitors (CFU-GEMM, CFU-Mix and CFU-blast). The CD34 is also expressed on stromal cell precursors. Terminal deoxynucleotidyl transferase (TdT)-positive B- and T-lymphoid precursors in normal bone also are CD34+. The CD34 antigen is typically present on early myeloid cells that express the CD33 antigen, but lack the CD14 and CD15 antigens and on early erythroid cells that express the CD71 antigen and dimly express the CD45 antigen. The CD34 antigen is also found on capillary endothelial cells and approximately 1% of human thymocytes. Normal peripheral blood lymphocytes, monocytes, granulocytes and platelets do not express the CD34 antigen. CD34 antigen density is highest on early haematopoietic progenitor cells and decreases as the cells mature. The antigen is undetectably on fully differentiated haematopoietic cells. Approximately 60% of acute B-lymphoid leukemia's and acute myeloid leukemia express the CD34 antigen. The antigen is not expressed on chronic lymphoid leukemia (B or T lineage) or lymphomas.

As the 38692 polypeptides of the invention may modulate 38692-mediated activities, they may be useful as of for developing novel diagnostic and therapeutic agents for 38692-mediated or related disorders, e.g., hematopoietic related disorders, or erythroid-associated disorders.

As used herein, the term "hematopoietic disorder" includes neoplastic and non-neoplastic hematopoietic or immune disorders. Examples of neoplastic immune disorders include, but are not limited to, erythroid leukemias, or leukemias of erythroid precursor cells, e.g., poorly differentiated acute leukemias such as erythroblastic leukemia and acute megakaryoblastic leukemia; acute promyeloid leukemia (APML), acute myelogenous leukemia (AML) and chronic myelogenous leukemia (CML) (reviewed in Vaickus, L. (1991) Crit Rev. in Oncol./Hemotol. 11:267–97). In particular, AML can include the uncontrolled proliferation of CD34+ cells such as AML subtypes M1 and M2, myeloblastic leukemias with and without maturation, and AML subtype M6, erythroleukemia (Di Guglielmo's disease). Additional neoplastic disorders include a myelodysplastic syndrome or preleukemic disorder, e.g., oligoblastic leukemia, smoldering leukemia. Additional cancers of the erythroid lineage include erythroblastosis, and other relevant diseases of the bone marrow.

The term "leukemia" or "leukemic cancer" is intended to have its clinical meaning, namely, a neoplastic disease in which white corpuscle maturation is arrested at a primitive stage of cell development. The disease is characterized by an increased number of leukemic blast cells in the bone marrow, and by varying degrees of failure to produce normal hematopoietic cells. The condition may be either acute or chronic. Leukemias are further typically categorized as being either lymphocytic i.e., being characterized by cells which have properties in common with normal lymphocytes, or myelocytic (or myelogenous), i.e., characterized by cells having some characteristics of normal granulocytic cells. Acute lymphocytic leukemia ("ALL") arises in lymphoid tissue, and ordinarily first manifests its presence in bone marrow. Acute myelocytic leukemia ("AML") arises from bone marrow hematopoietic stem cells or their progeny. The term acute myelocytic leukemia subsumes several subtypes of leukemia: myeloblastic leukemia, promyelocytic leukemia, and myelomonocytic leukemia. In addition, leukemias with erythroid or megakaryocytic properties are considered myelogenous leukemias as well.

Examples of non-neoplastic hematopoieitic disorders or diseases include, but are not limited to, autoimmune diseases (including, for example, diabetes mellitus, arthritis (including rheumatoid arthritis, juvenile rheumatoid arthritis, osteoarthritis, psoriatic arthritis), multiple sclerosis, encephalomyelitis, myasthenia gravis, systemic lupus erythematosis, autoimmune thyroiditis, dermatitis (including atopic dermatitis and eczematous dermatitis), psoriasis, Sjögren's Syndrome, Crohn's disease, aphthous ulcer, iritis, conjunctivitis, keratoconjunctivitis, ulcerative colitis, asthma, allergic asthma, cutaneous lupus erythematosus, scleroderma, vaginitis, proctitis, drug eruptions, leprosy reversal reactions, erythema nodosum leprosum, autoimmune uveitis, allergic encephalomyelitis, acute necrotizing hemorrhagic encephalopathy, idiopathic bilateral progressive sensorineural hearing loss, aplastic anemia, pure red cell anemia, idiopathic thrombocytopenia, polychondritis, Wegener's granulomatosis, chronic active hepatitis, Stevens-Johnson syndrome, idiopathic sprue, lichen planus, Graves' disease, sarcoidosis, primary biliary cirrhosis, uveitis posterior, and interstitial lung fibrosis), graft-versus-host disease, cases of transplantation, and allergy such as, atopic allergy.

As used herein, the term "erythroid associated disorders" include disorders involving aberrant (increased or deficient) erythroblast proliferation, e.g., an erythroleukemia, and aberrant (increased or deficient) erythroblast differentiation, e.g., an anemia. Erythrocyte-associated disorders include anemias such as, for example, hemolytic anemias due to hereditary cell membrane abnormalities, such as hereditary spherocytosis, hereditary elliptocytosis, and hereditary pyropoikilocytosis; hemolytic anemias due to acquired cell membrane defects, such as paroxysmal nocturnal hemoglobinuria and spur cell anemia; hemolytic anemias caused by antibody reactions, for example to the RBC antigens, or antigens of the ABO system, Lewis system, Ii system, Rh system, Kidd system, Duffy system, and Kell system; methemoglobinemia; a failure of erythropoiesis, for example, as a result of aplastic anemia, pure red cell aplasia, myelodysplastic syndromes, sideroblastic anemias, and congenital dyserythropoietic anemia; secondary anemia in nonhematolic disorders, for example, as a result of chemotherapy, alcoholism, or liver disease; anemia of chronic disease, such as chronic renal failure; and endocrine deficiency diseases.

Agents that modulate 38692 polypeptide or nucleic acid activity or expression can be used to treat anemias, in particular, anemias associated with cancer chemotherapy, chronic renal failure, malignancies, adult and juvenile rheumatoid arthritis, disorders of haemoglobin synthesis, prematurity, and zidovudine treatment of HIV infection. A subject receiving the treatment can be additionally treated with a second agent, e.g., erythropoietin, to futher ameliorate the condition.

As used herein, the term "erythropoietin" or "EPO" refers to a glycoprotein produced in the kidney, which is the principal hormone responsible for stimulating red blood cell production (erythrogenesis). EPO stimulates the division and differentiation of committed erythroid progenitors in the bone marrow. Normal plasma erythropoietin levels range from 0.01 to 0.03 Units/mL, and can increase up to 100 to 1,000-fold during hypoxia or anemia. Graber and Krantz, Ann. Rev. Med. 29:51 (1978); Eschbach and Adamson, Kidney Intl. 28:1 (1985). Recombinant human erythropoietin (rHuEpo or epoetin alfa) is commercially available as EPOGEN.RTM. (epoetin alfa, recombinant human erythropoietin) (Amgen Inc., Thousand Oaks, Calif.) and as PROCRIT.RTM. (epoetin alfa, recombinant human erythropoietin) (Ortho Biotech Inc., Raritan, N.J.).

Another example of an erythroid-associated disorder is erythrocytosis. Erythrocytosis, a disorder of red blood cell overproduction caused by excessive and/or ectopic erythropoietin production, can be caused by cancers, e.g., a renal cell cancer, a hepatocarcinoma, and a central nervous system cancer. Diseases associated with erythrocytosis include polycythemias, e.g., polycythemia vera, secondary polycythemia, and relative polycythemia.

Figure 11:
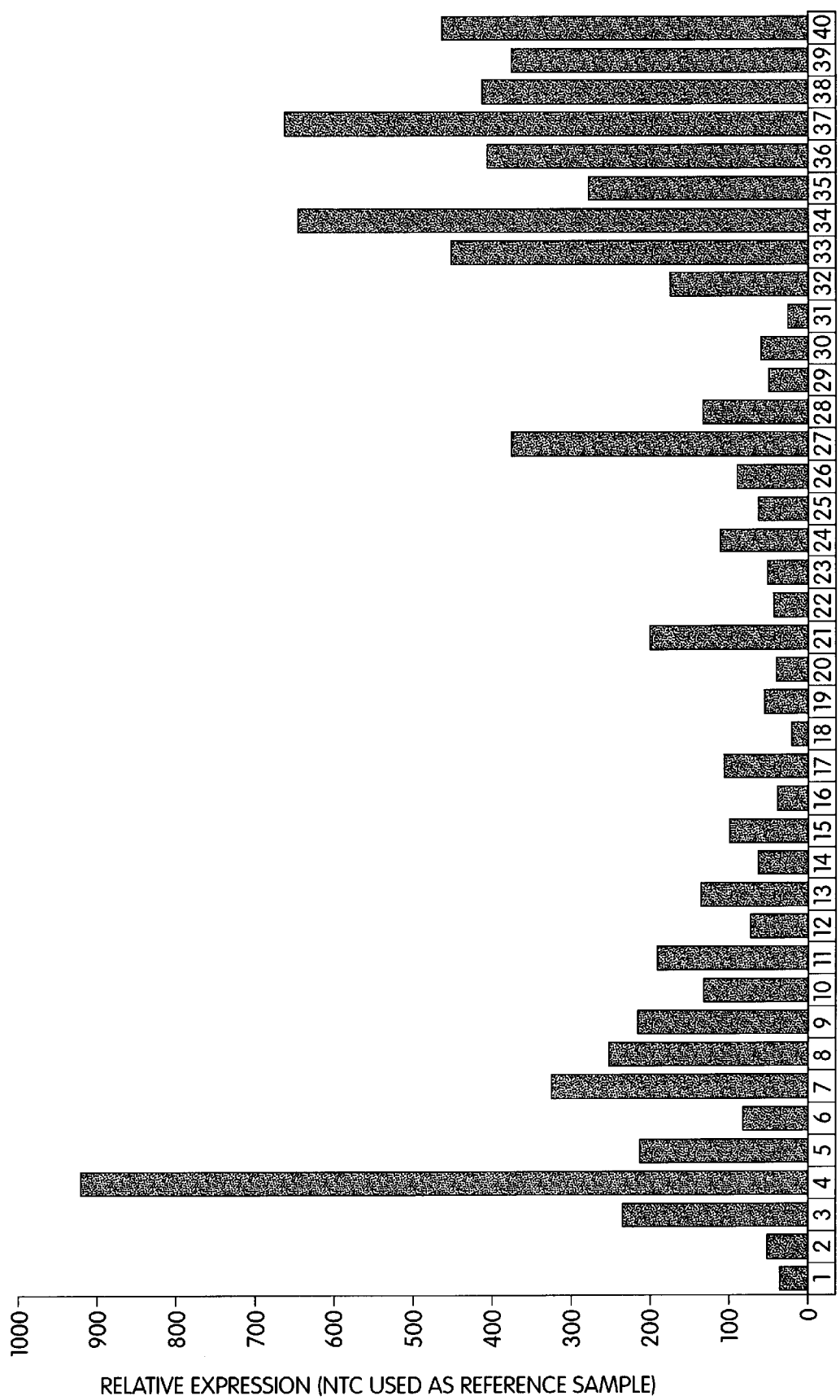
FIG. 11 shows a bar graph depicting relative 38692 mRNA expression as determined by TaqMan assays on mRNA derived from the following tissues or cell lines. Columns are numbered at five-column intervals at the bottom of the Figure (i.e., columns 1–40), and correspond to the following tissues or cell lines: (1) Lung; (2) Kidney; (3) Spleen; (4) Fetal Liver; (5) Granulocytes; (6) NHDF resting; (7) NHDF/TGF-treated for 48 hr; (8) NHLF/CTN-treated for 48 hr; (9) NHLF/TGF-treated for 48 hr; (10) NC Heps; (11) Passage Stellates; (12) Liver Pool; (13) LF/CHT 339; (14) LF/NDR 191; (15) LF/NDR 079; (16) Lymph Nodes NDR 173; (17) Tonsils; (18) TH1 24 hr; (19) CD4; (20) CD14 Resting; (21) CD19; (22) CD3 Resting; (23) bone marrow mononuclear cells (BM MNC) LP26; (24) mPB CD34+; (25) adult bone marrow (ABM) CD34+; (26) Cord Blood CD34+; (27) Erythroid; (28) Megakaryocytes LP16; (29) Neutrophils d14; (30) NBM CD15+/CD14-/34+; (31) mBM CD15+/CD11b-; (32) BM/glycophorin A (GPA); (33) Hepatocyte (Hep)G2-A; (34) HepG2.2.15-A; (35) HBV-Liver MAI-1; (36) HL60; (37) leukemia cell line K562; (38) Molt 4; (39) liver cell line Hep3B Nor; (40)Hep3B Hypoxia. High relative levels of expression were found in fetal liver cells, HepG2.2.15-A liver cells, and leukemic K562 cells.

As 38692 mRNA is also expressed in various liver cells and tissues, the molecules of the invention can be used to develop novel agents or compounds to treat and/or diagnose liver related disorders. For example, 38692 is expressed at high levels in fetal liver, HepG2.2.15-A liver cells, and Hep3B hypoxia cells (FIG. 11). Disorders involving the liver include, but are not limited to, hepatic injury; jaundice and cholestasis, such as bilirubin and bile formation; hepatic failure and cirrhosis, such as cirrhosis, portal hypertension, including ascites, portosystemic shunts, and splenomegaly; infectious disorders, such as viral hepatitis, including hepatitis A-E infection and infection by other hepatitis viruses, clinicopathologic syndromes, such as the carrier state, asymptomatic infection, acute viral hepatitis, chronic viral hepatitis, and fulminant hepatitis; autoimmune hepatitis; drug- and toxin-induced liver disease, such as alcoholic liver disease; inborn errors of metabolism and pediatric liver disease, such as hemochromatosis, Wilson disea $\alpha_1$,-antitrypsin deficiency, and neonatal hepatitis; intrahepatic biliary tract disease, such as secondary biliary cirrhosis, primary biliary cirrhosis, primary sclerosing cholangitis, and anomalies of the biliary tree; circulatory disorders, such as impaired blood flow into the liver, including hepatic artery compromise and portal vein obstruction and thrombosis, impaired blood flow through the liver, including passive congestion and centrilobular necrosis and peliosis hepatis, hepatic vein outflow obstruction, including hepatic vein thrombosis (Budd-Chiari syndrome) and veno-occlusive disease; hepatic disease associated with pregnancy, such as preeclampsia and eclampsia, acute fatty liver of pregnancy, and intrehepatic cholestasis of pregnancy; hepatic complications of organ or bone marrow transplantation, such as drug toxicity after bone marrow transplantation, graft-versus-host disease and liver rejection, and nonimmunologic damage to liver allografts; tumors and tumorous conditions, such as nodular hyperplasias, adenomas, and malignant tumors, including primary carcinoma of the liver and metastatic tumors.

21117 mRNA is expressed in normal breast, colon, and adipose tissue; prostate tumor; and lung chronic obstructive pulmonary disorder (COPD) tissue. Thus, diagnostic and therapeutic methods of using the 21117 molecules of the invention to treat/diagnose breast, colon, adipose, prostate, and lung disorders are also contemplated by the present invention.

Aberrant expression or activity of the 21117 or 38692 molecules may be involved in neoplastic disorders in addition to the ones described above. Accordingly, the molecules of the invention may also modulate the activity of neoplastic, non-hematopoetic tissues in which they are expressed, e.g., liver, colon, breast, lung, prostate, adipose tissue, endothelial cells, or bone cells, e.g., osteoblasts. Accordingly, the 21117 or 38692 molecules can act as novel diagnostic targets and therapeutic agents for controlling one or more of cellular proliferative and/or differentiative disorders. Examples of such cellular proliferative and/or differentiative disorders include cancer, e.g., carcinoma, sarcoma, or metastatic disorders. A metastatic tumor can arise from a multitude of primary tumor types, including but not limited to those of prostate, colon, lung, breast, and liver origin.

As used herein, the terms "cancer," "hyperproliferative" and "neoplastic" refer to cells having the capacity for autonomous growth, i e., an abnormal state or condition characterized by rapidly proliferating cell growth. Hyperproliferative and neoplastic disease states may be categorized as pathologic, i.e., characterizing or constituting a disease state, or may be categorized as non-pathologic, i.e., a deviation from normal but not associated with a disease state. The term is meant to include all types of cancerous growths or oncogenic processes, metastatic tissues or malignantly transformed cells, tissues, or organs, irrespective of histopathologic type or stage of invasiveness. "Pathologic hyperproliferative" cells occur in disease states characterized by malignant tumor growth. Examples of non-pathologic hyperproliferative cells include proliferation of cells associated with wound repair.

The terms "cancer" or "neoplasms" include malignancies of the various organ systems, such as affecting lung, breast, thyroid, lymphoid, gastrointestinal, and genito-urinary tract, as well as adenocarcinomas which include malignancies such as most colon cancers, renal-cell carcinoma, prostate cancer and/or testicular tumors, non-small cell carcinoma of the lung, cancer of the small intestine and cancer of the esophagus.

The term "carcinoma" is art recognized and refers to malignancies of epithelial or endocrine tissues including respiratory system carcinomas, gastrointestinal system carcinomas, genitourinary system carcinomas, testicular carcinomas, breast carcinomas, prostatic carcinomas, endocrine system carcinomas, and melanomas. Exemplary carcinomas include those forming from tissue of the cervix, lung, prostate, breast, head and neck, colon and ovary. The term also includes carcinosarcomas, e.g., which include malignant tumors composed of carcinomatous and sarcomatous tissues. An "adenocarcinoma" refers to a carcinoma derived from glandular tissue or in which the tumor cells form recognizable glandular structures.

The term "sarcoma" is art recognized and refers to malignant tumors of mesenchymal derivation.

The 38692 or 21117 protein, fragments thereof, and derivatives and other variants of the sequence in SEQ ID NO:2 or SEQ ID NO:5 thereof are collectively referred to as "polypeptides or proteins of the invention" or "38692 or 21117 polypeptides or proteins." Nucleic acid molecules encoding such polypeptides or proteins are collectively referred to as "nucleic acids of the invention" or "38692 or 21117 nucleic acids." 38692 or 21117 molecules refer to 38692 or 21117 nucleic acids, polypeptides, and antibodies.

As used herein, the term "nucleic acid molecule" includes DNA molecules (e.g., a cDNA or genomic DNA) and RNA molecules (e.g., an mRNA) and analogs of the DNA or RNA generated, e.g., by the use of nucleotide analogs. The nucleic acid molecule can be single-stranded or double-stranded, but preferably is double-stranded DNA.

The term "isolated or purified nucleic acid molecule" includes nucleic acid molecules that are separated from other nucleic acid molecules that are present in the natural source of the nucleic acid. For example, with respect to genomic DNA, the term "isolated" includes nucleic acid molecules that are separated from the chromosome with which the genomic DNA is naturally associated. Preferably, an "isolated" nucleic acid is free of sequences that naturally flank the nucleic acid (i.e., sequences located at the 5' and/or 3' ends of the nucleic acid) in the genomic DNA of the organism from which the nucleic acid is derived. For example, in various embodiments, the isolated nucleic acid molecule can contain less than about 5 kb, 4 kb, 3 kb, 2 kb, 1 kb, 0.5 kb or 0.1 kb of 5' and/or 3' nucleotide sequences that naturally flank the nucleic acid molecule in genomic DNA of the cell from which the nucleic acid is derived. Moreover, an "isolated" nucleic acid molecule, such as a cDNA molecule, can be substantially free of other cellular material, or culture medium when produced by recombinant techniques, or substantially free of chemical precursors or other chemicals when chemically synthesized.

As used herein, the term "hybridizes under low stringency, medium stringency, high stringency, or very high stringency conditions" describes conditions for hybridization and washing. Guidance for performing hybridization reactions can be found in *Current Protocols in Molecular Biology*, John Wiley & Sons, N.Y. (1989), 6.3.1–6.3.6, which is incorporated by reference. Aqueous and nonaqueous methods are described in that reference and either can be used. Specific hybridization conditions referred to herein are as follows: 1) low stringency hybridization conditions in 6× sodium chloride/sodium citrate (SSC) at about 45° C., followed by two washes in 0.2×SSC, 0.1% SDS at least at 50° C. (the temperature of the washes can be increased to 55° C. for low stringency conditions); 2) medium stringency hybridization conditions in 6×SSC at about 45° C., followed by one or more washes in 0.2×SSC, 0.1% SDS at 60° C.; 3) high stringency hybridization conditions in 6×SSC at about 45° C., followed by one or more washes in 0.2×SSC, 0.1% SDS at 65° C.; and preferably 4) very high stringency hybridization conditions are 0.5M sodium phosphate, 7% SDS at 65° C., followed by one or more washes at 0.2×SSC, 1% SDS at 65° C. Very high stringency conditions (4) are the preferred conditions and the ones that should be used unless otherwise specified.

As used herein, a "naturally-occurring" nucleic acid molecule refers to an RNA or DNA molecule having a nucleotide sequence that occurs in nature (e.g., encodes a natural protein).

As used herein, the terms "gene" and "recombinant gene" refer to nucleic acid molecules that include an open reading frame encoding a 38692 or 21117 protein, preferably a mammalian 38692 or 21117 protein, and further can include non-coding regulatory sequences and introns.

An "isolated" or "purified" polypeptide or protein is substantially free of cellular material or other contaminating proteins from the cell or tissue source from which the protein is derived, or substantially free from chemical precursors or other chemicals when chemically synthesized. In one embodiment, the language "substantially free" means preparation of 38692 or 21117 protein having less than about 30%, 20%, 10% and more preferably 5% (by dry weight), of non-38692 or 21117 protein (also referred to herein as a "contaminating protein"), or of chemical precursors or non-38692 or 21117 chemicals. When the 38692 or 21117 protein or biologically active portion thereof is recombinantly produced, it is also preferably substantially free of culture medium, i e., culture medium represents less than about 20%, more preferably less than about 10%, and most preferably less than about 5% of the volume of the protein preparation. The invention includes isolated or purified preparations of at least 0.01, 0.1, 1.0, and 10 milligrams in dry weight.

A "non-essential" amino acid residue is a residue that can be altered from the wild-type sequence of 38692 or 21117 (e.g., the sequence of SEQ ID NO:1, 3, 4, or 6), without abolishing or more preferably, without substantially altering a biological activity of the 38692 or 21117 protein, whereas an "essential" amino acid residue results in such a change. For example, amino acid residues that are conserved among the polypeptides of the present invention, e.g., those present in the phosphotase catalytic domain, are predicted to be particularly unamenable to alteration.

A "conservative amino acid substitution" is one in which the amino acid residue is replaced with an amino acid residue having a similar side chain. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine). Thus, a predicted nonessential amino acid residue in a 38692 or 21117 protein is preferably replaced with another amino acid residue from the same side chain family. Alternatively, in another embodiment, mutations can be introduced randomly along all or part of a 38692 or 21117 coding sequence, such as by saturation mutagenesis, and the resultant mutants can be screened for 38692 or 21117 biological activity to identify mutants that retain activity. Following mutagenesis of SEQ ID NO:1, 3, 4, or 6, the encoded protein can be expressed recombinantly and the activity of the protein can be determined.

As used herein, a "biologically active portion" of a 38692 or 21117 protein includes a fragment of a 38692 or 21117 protein that participates in an interaction between a 38692 or 21117 molecule and a non-38692 or 21117 molecule. Biologically active portions of a 38692 or 21117 protein include peptides comprising amino acid sequences sufficiently homologous to or derived from the amino acid sequence of the 38692 or 21117 protein, e.g., the amino acid sequence shown in SEQ ID NO:2 or SEQ ID NO:5, which include less amino acids than the full length 38692 or 21117 protein and exhibit at least one activity of a 38692 or 21117 protein.

Typically, biologically active portions comprise a domain or motif with at least one activity of the 38692 or 21117 protein, e.g., serine/threonine phosphatase activity. A biologically active portion of a 38692 or 21117 protein can be a polypeptide that is, for example, 10, 25, 50, 100, 200 or more amino acids in length. Biologically active portions of a 38692 or 21117 protein can be used as targets for developing agents that modulate a 38692 or 21117 mediated activity, e.g., serine/threonine phosphatase activity.

Particularly preferred 38692 or 21117 polypeptides of the present invention have an amino acid sequence substantially identical to the amino acid sequence of SEQ ID NO:2 or SEQ ID NO:5. In the context of an amino acid sequence, the term "substantially identical" is used herein to refer to a first amino acid that contains a sufficient or minimum number of amino acid residues that are i) identical to, or ii) conservative substitutions of aligned amino acid residues in a second amino acid sequence such that the first and second amino acid sequences can have a common structural domain and/or common functional activity. For example, amino acid sequences that contain a common structural domain having at least about 60%, or 65% identity, likely 75% identity, more likely 85%, 90%. 91%, 92%, 93%, 94%, 95%, 96%, 97%, 98% or 99% identity to SE ID NO:2 or SEQ ID NO:5 are termed substantially identical.

In the context of nucleotide sequence, the term "substantially identical" is used herein to refer to a first nucleic acid sequence that contains a sufficient or minimum number of nucleotides that are identical to aligned nucleotides in a second nucleic acid sequence such that the first and second nucleotide sequences encode a polypeptide having common functional activity, or encode a common structural polypeptide domain or a common functional polypeptide activity. For example, nucleotide sequences having at least about 60%, or 65% identity, likely 75% identity, more likely 85%, 90%. 91%, 92%, 93%, 94%, 95%, 96%, 97%, 98% or 99% identity to SEQ ID NO:1, 3, 4, or 6 are termed substantially identical.

Calculations of homology or sequence identity between sequences (the terms are used interchangeably herein) are performed as follows.

To determine the percent identity of two amino acid sequences, or of two nucleic acid sequences, the sequences are aligned for optimal comparison purposes (e.g., gaps can be introduced in one or both of a first and a second amino acid or nucleic acid sequence for optimal alignment and non-homologous sequences can be disregarded for comparison purposes). In a preferred embodiment, the length of a reference sequence aligned for comparison purposes is at least 30%, preferably at least 40%, more preferably at least 50%, even more preferably at least 60%, and even more preferably at least 70%, 80%, 90%, 100% of the length of the reference sequence (e.g., when aligning a second sequence to the 21117 amino acid sequence of SEQ ID NO:2 having 666 amino acid residues, at least 202, preferably at least 268, more preferably at least 335, even more preferably at least 402, and even more preferably at least 469, 536 or 603 amino acid residues are aligned). The amino acid residues or nucleotides at corresponding amino acid positions or nucleotide positions are then compared. When a position in the first sequence is occupied by the same amino acid residue or nucleotide as the corresponding position in the second sequence, then the molecules are identical at that position (as used herein amino acid or nucleic acid "identity" is equivalent to amino acid or nucleic acid "homology"). The percent identity between the two sequences is a function of the number of identical positions shared by the sequences, taking into account the number of gaps, and the length of each gap, which need to be introduced for optimal alignment of the two sequences.

The comparison of sequences and determination of percent identity between two sequences can be accomplished using a mathematical algorithm. In a preferred embodiment, the percent identity between two amino acid sequences is determined using the Needleman and Wunsch (*J. Mol. Biol.* (48):444–453 (1970)) algorithm which has been incorporated into the GAP program in the GCG software package, using either a Blossum 62 matrix or a PAM250 matrix, and a gap weight of 16, 14, 12, 10, 8, 6, or 4 and a length weight of 1, 2, 3, 4, 5, or 6. In yet another preferred embodiment, the percent identity between two nucleotide sequences is determined using the GAP program in the GCG software package, using a NWSgapdna.CIVIP matrix and a gap weight of 40, 50, 60, 70, or 80 and a length weight of 1, 2, 3, 4, 5, or 6. A particularly preferred set of parameters (and the one that should be used if the practitioner is uncertain about what parameters should be applied to determine if a molecule is within the invention) is using a Blossum 62 scoring matrix with a gap open penalty of 12, a gap extend penalty of 4, and a frameshift gap penalty of 5.

The percent identity between two amino acid or nucleotide sequences can be determined using the algorithm of Meyers and Miller (CABIOS, 4:11–17 (1989)) which has been incorporated into the ALIGN program (version 2.0), using a PAM120 weight residue table, a gap length penalty of 12 and a gap penalty of 4.

The nucleic acid and protein sequences described herein can be used as a "query sequence" to perform a search against public databases to, for example, identify other family members or related sequences. Such searches can be performed using the NBLAST and XBLAST programs (version 2.0) of Altschul, et al. (1990) *J. Mol. Biol.* 215:403–10. BLAST nucleotide searches can be performed with the NBLAST program, score=100, wordlength=12 to obtain nucleotide sequences homologous to 38692 or 21117 nucleic acid molecules of the invention. BLAST protein searches can be performed with the XBLAST program, score=50, wordlength=3 to obtain amino acid sequences homologous to 38692 or 21117 protein molecules of the invention. To obtain gapped alignments for comparison purposes, Gapped BLAST can be utilized as described in Altschul et al., (1997) *Nucleic Acids Res.* 25(17):3389–3402. When utilizing BLAST and Gapped BLAST programs, the default parameters of the respective programs (e.g., XBLAST and NBLAST) can be used.

"Misexpression or aberrant expression", as used herein, refers to a non-wild type pattern of gene expression, at the RNA or protein level. It includes: expression at non-wild type levels, i.e., over or under expression; a pattern of expression that differs from wild type in terms of the time or stage at which the gene is expressed, e.g., increased or decreased expression (as compared with wild type) at a predetermined developmental period or stage; a pattern of expression that differs from wild type in terms of decreased expression (as compared with wild type) in a predetermined cell type or tissue type; a pattern of expression that differs from wild type in terms of the splicing size, amino acid sequence, post-transitional modification, or biological activity of the expressed polypeptide; a pattern of expression that differs from wild type in terms of the effect of an environmental stimulus or extracellular stimulus on expression of the gene, e.g., a pattern of increased or decreased expression (as compared with wild type) in the presence of an increase or decrease in the strength of the stimulus.

"Subject," as used herein, refers to human and non-human animals. The term "non-human animals" of the invention includes all vertebrates, e.g., mammals, such as non-human primates (particularly higher primates), sheep, dog, rodent (e.g., mouse or rat), guinea pig, goat, pig, cat, rabbits, cow, and non-mammals, such as chickens, amphibians, reptiles, etc. In a preferred embodiment, the subject is a human. In another embodiment, the subject is an experimental animal or animal suitable as a disease model.

A "purified preparation of cells", as used herein, refers to, in the case of plant or animal cells, an in vitro preparation of cells and not an entire intact plant or animal. In the case of cultured cells or microbial cells, it consists of a preparation of at least 10% and more preferably 50% of the subject cells.

Various aspects of the invention are described in further detail below.

Isolated Nucleic Acid Molecules

In one aspect, the invention provides an isolated or purified nucleic acid molecule that encodes a 38692 or 21117 polypeptide described herein, e.g., a full-length 38692 or 21117 protein or a fragment thereof, e.g., a biologically active portion of a 38692 or 21117 protein. Also included is a nucleic acid fragment suitable for use as a hybridization probe, which can be used, e.g., to identify a nucleic acid molecule encoding a polypeptide of the invention, 38692 or 21117 mRNA, or fragments suitable for use as primers, e.g., PCR primers for the amplification or mutation of nucleic acid molecules.

In one embodiment, an isolated nucleic acid molecule of the invention includes the nucleotide sequence shown in SEQ ID NO: 1, 3, 4, 6, or a portion of any of these nucleotide sequences. In one embodiment, the nucleic acid molecule includes sequences encoding the 38692 or 21117 protein (i.e., "the coding region,") as well as 5' untranslated sequences. Alternatively, the nucleic acid molecule can include only the coding region of SEQ ID NO:1 or 4 (e.g., the sequences corresponding to SEQ ID NOs:3 and 6) and, e.g., no flanking sequences that normally accompany the subject sequence.

In another embodiment, an isolated nucleic acid molecule of the invention includes a nucleic acid molecule that is a complement of the nucleotide sequence shown in SEQ ID NO: 1, 3, 4, or 6, or a portion of any of these nucleotide sequences. In other embodiments, the nucleic acid molecule of the invention is sufficiently complementary to the nucleotide sequence shown in SEQ ID NO:1, 3, 4, or 6, such that it can hybridize to the nucleotide sequence shown in SEQ ID NO:1, 3, 4, or 6, thereby forming a stable duplex.

In one embodiment, an isolated nucleic acid molecule of the present invention includes a nucleotide sequence that is at least about: 60%, 65%, 70%, 75%, 80%, 85%, 90%, 91%, 92%, 93%, 94%, 95%, 96%, 97%, 98%, 99%, or more homologous to the entire length of the nucleotide sequence shown in SEQ ID NO: 1, 3, 4, or 6. In the case of an isolated nucleic acid molecule which is longer than or equivalent in length to the reference sequence, e.g., SEQ ID NO:1 or 3, the comparison is made with the full length of the reference sequence. Where the isolated nucleic acid molecule is shorter that the reference sequence, e.g., shorter than SEQ ID NO:1 or 3, the comparison is made to a segment of the reference sequence of the same length (excluding any loop required by the homology calculation).

38692 or 21117 Nucleic Acid Fragments

A nucleic acid molecule of the invention can include only a portion of the nucleic acid sequence of SEQ ID NO:1, 3, 4, or 6. For example, such a nucleic acid molecule can include a fragment that can be used as a probe or primer or a fragment encoding a portion of a 38692 or 21117 protein, e.g., an immunogenic or biologically active portion of a 38692 or 21117 protein. A fragment can comprise a nucleotides encoding amino acids 158 to 297 of SEQ ID NO:2 or amino acids 28 to 173 of SEQ ID NO:5, which encode a phosphotase catalytic domain of human 21117 or 38692. The nucleotide sequence determined from the cloning of the 38692 or 21117 gene allows for the generation of probes and primers designed for use in identifying and/or cloning other 38692 or 21117 family members, or fragments thereof, as well as 38692 or 21117 homologues or fragments thereof, from other species.

In another embodiment, a nucleic acid includes a nucleotide sequence that includes part, or all, of the coding region and extends into either (or both) the 5' or 3' noncoding region. Other embodiments include a fragment that includes a nucleotide sequence encoding an amino acid fragment described herein. Nucleic acid fragments can encode a specific domain or site described herein or fragments thereof, particularly fragments thereof which are at least 183 or 185 amino acids in length. Fragments also include nucleic acid sequences corresponding to specific amino acid sequences described above or fragments thereof. Nucleic acid fragments should not to be construed as encompassing those fragments that may have been disclosed prior to the invention.

A nucleic acid fragment can include a sequence corresponding to a domain, region, or functional site described herein. A nucleic acid fragment also can include one or more domains, regions, or functional sites described herein.

In a preferred embodiment, the fragment is at least 50, 100, 150, 182, 185, 200, 250, 300, 350, 400, 450, 500, 550, 600, 650, 700, 750, 800, 850, 900, 950, or 1000 nucleotides in length, and hybridizes under a stringent hybridization condition as described herein to a nucleic acid molecule of SEQ ID NO:1, or SEQ ID NO:3.

38692 or 21117 probes and primers are provided. Typically a probe/primer is an isolated or purified oligonucleotide. The oligonucleotide typically includes a region of nucleotide sequence that hybridizes under a stringent hybridization condition as described herein to at least about 7, 12 or 15, preferably about 20 or 25, more preferably about 30, 35, 40, 45, 50, 55, 60, 65, or 75 consecutive nucleotides of a sense or antisense sequence of SEQ ID NO: 1, 3, 4, or 6, of a naturally occurring allelic variant or mutant of SEQ ID NO:1, 3, 4, or 6.

In a preferred embodiment the nucleic acid is a probe that is at least 5 or 10 and less than 500, 300, or 200 base pains in length, and more preferably is less than 100 or less than 50 base pairs in length. It should be identical, or differ by 1, or less than 5 or 10 bases, from a sequence disclosed herein. If alignment is needed for this comparison, the sequences should be aligned for maximum homology. "Looped" out sequences in the alignment from deletions, insertions, or mismatches, are considered differences.

A probe or primer can be derived from the sense or anti-sense strand of a nucleic acid that encodes a dual specificity phosphatase catalytic domain: amino acids 158 to 297 of SEQ ID NO:2 or 28 to 173 of SEQ ID NO:5.

In another embodiment a set of primers is provided, e.g., primers suitable for use in a PCR, which can be used to amplify a selected region of a 38692 or 21117 sequence, e.g., a region, domain, or site described herein. The primers should be at least 5, 10, or 50 base pairs in length and less than 100 or 200 base pairs in length. The primers should be identical, or differ by one base from a sequence disclosed herein or from a naturally occurring variant. E.g., primers suitable for amplifying all or a portion of the dual specificity phosphatase catalytic domain: amino acids 158 to 297 of SEQ ID NO:2 or 28 to 173 of SEQ ID NO:5.

A nucleic acid fragment can encode an epitope bearing region of a polypeptide described herein.

A nucleic acid fragment encoding a "biologically active portion of a 38692 or 21117 polypeptide" can be prepared by isolating a portion of the nucleotide sequence of SEQ ID NO:1, 3, 4, or 6, which encodes a polypeptide having a 38692 or 21117 biological activity (e.g., the biological activities of the 38692 or 21117 proteins described herein), expressing the encoded portion of the 38692 or 21117 protein (e.g., by recombinant expression in vitro) and assessing the activity of the encoded portion of the 38692 or 21117 protein. For example, a nucleic acid fragment encoding a biologically active portion of 38692 or 21117 includes a dual specificity phosphatase catalytic domain, e.g., amino acid residues 158 to 297 of SEQ ID NO:2 or residues 28 to 173 of SEQ ID NO:5. A nucleic acid fragment encoding a biologically active portion of a 38692 or 21117 polypeptide, may comprise a nucleotide sequence that is greater than about 300 or more nucleotides in length (e.g., greater than about 400 nucleotides in length).

In preferred embodiments, a nucleic acid includes a nucleotide sequence which is about 300, 400, 500, 600, 700, 800, 900, 1000, 1100, 1200, 1300 or more nucleotides in length and hybridizes under a stringency condition described herein to a nucleic acid molecule of SEQ ID NO:3.

In preferred embodiments, a nucleic acid includes a nucleotide sequence which is about 554, 600, 700, 800, 900, 1000, 1100, 1200, 1300 or more nucleotides in length and hybridizes under a stringency condition described herein to a nucleic acid molecule of SEQ ID NO:1.

In preferred embodiments, a nucleic acid includes a nucleotide sequence which is about 400, 500, 550, 600, 650, 700, 800, 900, 1000, 1100, 1200, 1300 or more nucleotides in length and hybridizes under a stringency condition described herein to a nucleic acid molecule of SEQ ID NO:4 or 6.

In a preferred embodiment, a nucleic acid fragment has a nucleotide sequence other than (e.g., differs by one or more nucleotides from) Genbank accession numbers: AW014773, AI807619, AI492892, AI206123, AI637845, AA761314, or HSU87169.

In a preferred embodiment, a nucleic acid fragment includes at least one, preferably more, nucleotides from the sequence of nucleotide 1 to 2985 of SEQ ID NO:1.

In a preferred embodiment, a nucleic acid fragment includes at least one, preferably more, nucleotides from the sequence of nucleotides 1 to 432 of SEQ ID NO:4, or nucleotides 850 to 1114 of SEQ ID NO:4.

38692 or 21117 Nucleic Acid Variants

The invention further encompasses nucleic acid molecules that differ from the nucleotide sequence shown in SEQ ID NO:1, 3, 4, or 6. Such differences can be due to degeneracy of the genetic code (and result in a nucleic acid that encodes the same 38692 or 21117 proteins as those encoded by the nucleotide sequence disclosed herein. In another embodiment, an isolated nucleic acid molecule of the invention has a nucleotide sequence encoding a protein having an amino acid sequence that differs by at least 1, but less than 5, 10, 20, 50, or 100 amino acid residues than that shown in SEQ ID NO:2 or SEQ ID NO:5. If alignment is needed for this comparison the sequences should be aligned for maximum homology. "Looped" out sequences from deletions, insertions, or mismatches are considered differences.

Nucleic acids of the invention can be chosen for having codons, which are preferred, or non-preferred, for a particular expression system (e.g., the nucleic acid can be one in which at least one codon, at preferably at least 10%, or 20% of the codons has been altered such that the sequence is optimized for expression in E. Coli, yeast, human, insect, or chinese hamster ovary (CHO) cells).

Nucleic acid variants can be naturally occurring, such as allelic variants (same locus), homologs (different locus), and orthologs (different organism) or can be non-naturally occurring. Non-naturally occurring variants can be made by mutagenesis techniques, including those applied to polynucleotides, cells, or organisms. The variants can contain nucleotide substitutions, deletions, inversions, and insertions. Variation can occur in either or both the coding and non-coding regions. The variations can produce both conservative and non-conservative amino acid substitutions (as compared with the encoded product).

In a preferred embodiment, the nucleic acid differs from that of SEQ ID NO: 1 or 3, as follows: by at least one but less than 10, 20, 30, or 40 nucleotides; at least one but less than 1%, 5%, 10% or 20% of the nucleotides in the subject nucleic acid, if necessary for this analysis, the sequences should be aligned for maximum homology. "Looped" out sequences from deletions, insertions, or mismatches, are considered differences.

Orthologs, homologs, and allelic variants can be identified using methods known in the art. These variants comprise a nucleotide sequence encoding a polypeptide that is 50%, at least about 55%, typically at least about 70–75%, more typically at least about 80–85%, and most typically at least about 90–95% or more identical to the amino acid sequence shown in SEQ ID NO:2 or SEQ ID NO:5 or a fragment of this sequence. Such nucleic acid molecules can be obtained as being able to hybridize under a stringent hybridization condition as described herein, to the nucleotide sequence shown in SEQ ID NO:1 or 3 or a fragment of the sequence. Nucleic acid molecules corresponding to orthologs, homologs, and allelic variants of the 38692 or 21117 cDNAs of the invention can further be isolated by mapping to the same chromosome or locus as the 38692 or 21117 gene. Preferred variants include those that are correlated with serine/threonine phosphatase activity.

Orthologs, homologs, and allelic variants can be identified using methods known in the art. These variants comprise a nucleotide sequence encoding a polypeptide that is 50%, at least about 55%, typically at least about 70–75%, more typically at least about 80–85%, and most typically at least about 90–95% or more identical to the amino acid sequence shown in SEQ ID NO:2 or SEQ ID NO:5 or a fragment of this sequence. Such nucleic acid molecules can readily be identified as being able to hybridize under stringent conditions, to the nucleotide sequence shown in SEQ ID NO:1 or 3 or a fragment of the sequence. Nucleic acid molecules corresponding to orthologs, homologs, and allelic variants of the 38692 or 21117 cDNAs of the invention can further be isolated by mapping to the same chromosome or locus as the 38692 or 21117 gene. Preferred variants include those that are correlated with phosphatase activity, e.g., dual specificity phosphatase activity.

Allelic variants of 38692 or 21117, e.g., human 38692 or 21117, include both functional and non-functional proteins. Functional allelic variants are naturally occurring amino acid sequence variants of the 38692 or 21117 protein within a population that maintain the ability to remove the phosphate from a serine or threonine residue of a phosphorylated protein. Functional allelic variants typically will contain only conservative substitution of one or more amino acids of SEQ ID NO:2 or SEQ ID NO:5, or substitution, deletion or insertion of non-critical residues in non-critical regions of the protein. Non-functional allelic variants are naturally-occurring amino acid sequence variants of the 38692 or 21117, e.g., human 38692 or 21117, protein within a population that do not have the ability to remove the phosphate from a serine or threonine residue of a phosphorylated protein. Non-functional allelic variants will typically contain a non-conservative substitution, a deletion, or insertion, or premature truncation of the amino acid sequence of SEQ ID NO:2 or SEQ ID NO:5, or a substitution, insertion, or deletion in critical residues or critical regions of the protein.

Moreover, nucleic acid molecules encoding other 38692 or 21117 family members and, thus have a nucleotide sequence that differs from the 38692 or 21117 sequences of SEQ ID NO:1, 3, 4, or 6.

Antisense Nucleic Acid Molecules, Ribozymes and Modified 38692 or 21117 Nucleic Acid Molecules In another aspect, the invention features, an isolated nucleic acid molecule that is antisense to 38692 or 21117. An "antisense" nucleic acid can include a nucleotide sequence that is complementary to a "sense" nucleic acid encoding a protein, e.g., complementary to the coding strand of a double-stranded cDNA molecule or complementary to an mRNA sequence. The antisense nucleic acid can be complementary to an entire 38692 or 21117 coding strand, or to only a portion thereof (e.g., the coding region of 38692 or 21117 corresponding to SEQ ID NO:3 or 6). In another embodiment, the antisense nucleic acid molecule is antisense to a "noncoding region" of the coding strand of a nucleotide sequence encoding 38692 or 21117 (e.g., the 5' and 3' untranslated regions).

An antisense nucleic acid can be designed such that it is complementary to the entire coding region of 38692 or 21117 mRNA, but more preferably is an oligonucleotide that is antisense to only a portion of the coding or noncoding region of 38692 or 21117 mRNA. For example, the antisense oligonucleotide can be complementary to the region surrounding the translation start site of 38692 or 21117 mRNA, e.g., between the −10 and +10 regions of the target gene nucleotide sequence. An antisense oligonucleotide can be, for example, about 7, 10, 15, 20, 25, 30, 35, 40, 45, 50, 55, 60, 65, 70, 75, 80, or more nucleotides in length.

An antisense nucleic acid of the invention can be constructed using chemical synthesis and enzymatic ligation reactions with procedures known in the art. For example, an antisense nucleic acid (e.g., an antisense oligonucleotide) can be chemically synthesized using naturally occurring nucleotides or variously modified nucleotides designed to increase the biological stability of the molecules or to increase the physical stability of the duplex formed between the antisense and sense nucleic acids, e.g., phosphorothioate derivatives and acridine substituted nucleotides can be used. The antisense nucleic acid also can be produced biologically using an expression vector into which a nucleic acid has been subcloned in an antisense orientation (i.e., RNA transcribed from the inserted nucleic acid will be of an antisense orientation to a target nucleic acid of interest, described further in the following subsection).

The antisense nucleic acid molecules of the invention are typically administered to a subject (e.g., by direct injection at a tissue site), or generated in situ such that they hybridize with or bind to cellular mRNA and/or genomic DNA encoding a 38692 or 21117 protein to thereby inhibit expression of the protein, e.g., by inhibiting transcription and/or translation. Alternatively, antisense nucleic acid molecules can be modified to target selected cells and then administered systemically. For systemic administration, antisense molecules can be modified such that they specifically bind to receptors or antigens expressed on a selected cell surface, e.g., by linking the antisense nucleic acid molecules to peptides or antibodies that bind to cell surface receptors or antigens. The antisense nucleic acid molecules can also be delivered to cells using the vectors described herein. To achieve sufficient intracellular concentrations of the antisense molecules, vector constructs in which the antisense nucleic acid molecule is placed under the control of a strong polymerase II or polymerase III promoter are preferred.

In yet another embodiment, the antisense nucleic acid molecule of the invention is an α-anomeric nucleic acid molecule. An α-anomeric nucleic acid molecule forms specific double-stranded hybrids with complementary RNA in which, contrary to the usual β-units, the strands run parallel to each other (Gaultier et al. (1987) *Nucleic Acids. Res.* 15:6625–6641). The antisense nucleic acid molecule can also comprise a 2'-o-methylribonucleotide (Inoue et al. (1987) *Nucleic Acids Res.* 15:6131–6148) or a chimeric RNA-DNA analogue (Inoue et al. (1987) *FEBS Lett.* 215:327–330).

In still another embodiment, an antisense nucleic acid of the invention is a ribozyme. A ribozyme having specificity for a 38692 or 21117-encoding nucleic acid can include one or more sequences complementary to the nucleotide sequence of a 38692 or 21117 cDNA disclosed herein (i.e., SEQ ID NO:1, 3, 4, or 6), and a sequence having known catalytic sequence responsible for mRNA cleavage (see U.S. Pat. No. 5,093,246 or Haselhoff and Gerlach (1988) *Nature* 334:585–591). For example, a derivative of a Tetrahymena L-19 IVS RNA can be constructed in which the nucleotide sequence of the active site is complementary to the nucleotide sequence to be cleaved in a 38692 or 21117-encoding mRNA. See, e.g., Cech et al. U.S. Pat. No. 4,987,071; and Cech et al. U.S. Pat. No. 5,116,742. Alternatively, 38692 or 21117 mRNA can be used to select a catalytic RNA having a specific ribonuclease activity from a pool of RNA molecules. See, e.g., Bartel, D. and Szostak, J. W. (1993) *Science* 261:1411–1418.

38692 or 21117 gene expression can be inhibited by targeting nucleotide sequences complementary to the regulatory region of the 38692 or 21117 (e.g., the 38692 or 21117 promoter and/or enhancers) to form triple helical structures that prevent transcription of the 38692 or 21117 gene in target cells. See generally, Helene, C. (1991) *Anticancer Drug Des.* 6(6):569–84; Helene, C. et al. (1992) *Ann. N.Y. Acad. Sci.* 660:27–36; and Maher, L. J. (1992) *Bioassays* 14(12):807–15. The potential sequences that can be targeted for triple helix formation can be increased by creating a "switchback" nucleic acid molecule. Switchback molecules are synthesized in an alternating 5'–3',3'–5' manner, such that they base pair with first one strand of a duplex and then the other, eliminating the necessity for a sizeable stretch of either purines or pyrimidines to be present on one strand of a duplex.

The invention also provides detectably labeled oligonucleotide primer and probe molecules. Typically, such labels are chemiluminescent, fluorescent, radioactive, or colorimetric.

A 38692 or 21117 nucleic acid molecule can be modified at the base moiety, sugar moiety or phosphate backbone to improve, e.g., the stability, hybridization, or solubility of the molecule. For example, the deoxyribose phosphate backbone of the nucleic acid molecules can be modified to generate peptide nucleic acids (see Hyrup B. et al. (1996)

*Bioorganic & Medicinal Chemistry* 4 (1): 5–23). As used herein, the terms "peptide nucleic acid" or "PNA" refers to a nucleic acid mimic, e.g., a DNA mimic in which the deoxyribose phosphate backbone is replaced by a pseudopeptide backbone and only the four natural nucleobases are retained. The neutral backbone of a PNA can allow for specific hybridization to DNA and RNA under conditions of low ionic strength. The synthesis of PNA oligomers can be performed using standard solid phase peptide synthesis protocols as described in Hyrup B. et al. (1996) supra; Perry-O'Keefe et al. Proc. Natl. Acad. Sci. 93: 14670–675.

PNAs of 38692 or 21117 nucleic acid molecules can be used in therapeutic and diagnostic applications. For example, PNAs can be used as antisense or antigene agents for sequence-specific modulation of gene expression by, for example, inducing transcription or translation arrest or inhibiting replication. PNAs of 38692 or 21117 nucleic acid molecules can also be used in the analysis of single base pair mutations in a gene, (e.g., by PNA-directed PCR clamping); as 'artificial restriction enzymes' when used in combination with other enzymes, (e.g., S1 nucleases (Hyrup B. (1996) supra)); or as probes or primers for DNA sequencing or hybridization (Hyrup B. et al. (1996) supra; Perry-O'Keefe supra).

In other embodiments, the oligonucleotide may include other appended groups such as peptides (e.g., for targeting host cell receptors in vivo), or agents facilitating transport across the cell membrane (see, e.g., Letsinger et al. (1989) *Proc. Natl. Acad. Sci. USA* 86:6553–6556; Lemaitre et al. (1987) *Proc. Natl. Acad. Sci. USA* 84:648–652; PCT Publication No. WO88/09810) or the blood-brain barrier (see, e.g., PCT Publication No. WO89/10134). In addition, oligonucleotides can be modified with hybridization-triggered cleavage agents (see, e.g., Krol et al. (1988) *Bio-Techniques* 6:958–976) or intercalating agents (see, e.g., Zon (1988) *Pharm. Res.* 5:539–549). To this end, the oligonucleotide may be conjugated to another molecule, (e.g., a peptide, hybridization triggered cross-linking agent, transport agent, or hybridization-triggered cleavage agent).

The invention also includes molecular beacon oligonucleotide primer and probe molecules having at least one region that is complementary to a 38692 or 21117 nucleic acid of the invention. The molecular beacon primer and probe molecules also have two complementary regions, one having a fluorophore and one having a quencher, such that the molecular beacon is useful for quantitating the presence of a 38692 or 21117 nucleic acid of the invention in a sample. Molecular beacon nucleic acids are described, for example, in Lizardi et al., U.S. Pat. No. 5,854,033; Nazarenko et al., U.S. Pat. No. 5,866,336, and Livak et al., U.S. Pat. No. 5,876,930.

Isolated 38692 or 21117 Polypeptides

In another aspect, the invention features an isolated 38692 or 21117 protein or fragment thereof, e.g., a biologically active portion for use as immunogens or antigens to raise or test (or more generally to bind) anti-38692 or 21117 antibodies. 38692 or 21117 protein can be isolated from cells or tissue sources using standard protein purification techniques. 38692 or 21117 protein or fragments thereof can be produced by recombinant DNA techniques or synthesized chemically.

Polypeptides of the invention include those that arise as a result of the existence of multiple genes, alternative transcription events, alternative RNA splicing events, and alternative translational and postranslational events. The polypeptide can be expressed in systems, e.g., cultured cells, which result in substantially the same postranslational modifications present when expressed the polypeptide is expressed in a native cell, or in systems which result in the alteration or omission of postranslational modifications, e.g., glycosylation or cleavage, present when expressed in a native cell.

In a preferred embodiment, a 38692 or 21117 polypeptide has one or more of the following characteristics:

(i) it has the ability to promote removal of phosphate from phosphorylated serine, threonine, or tyrosine residues of protein;

(ii) it has a molecular weight (e.g., a deduced molecular weight), amino acid composition or other physical characteristic of a 38692 or 21117 protein, e.g., a 38692 or 21117 protein of SEQ ID NO:2 or SEQ ID NO:5;

(iii) it has an overall sequence similarity of at least 60%, more preferably at least 70, 80, 90, 95%, most preferably at least 99%, with a polypeptide encoded by SEQ ID NO:2 or 5;

(iv) it has a dual specificity phosphatase catalytic domain which is preferably about 70%, 80%, 90%, 95%, most preferably at least 99%, identical to amino acid residues 158 to 297 of SEQ ID NO:2 or 28 to 173 of SEQ ID NO:5; or (v) it has at least 70%, preferably at least 80%, and most preferably at least 95% of the cysteines found in the amino acid sequence of the native protein.

In a preferred embodiment, the 38692 or 21117 protein or fragment thereof differs from the corresponding sequence in SEQ ID NO:2 or SEQ ID NO:5. In one embodiment, it differs by at least one but by less than 15, 10 or 5 amino acid residues. In another embodiment, it differs from the corresponding sequence in SEQ ID NO:2 or SEQ ID NO:5 by at least one residue but less than 20%, 15%, 10% or 5% of the residues in it differ from the corresponding sequence in SEQ ID NO:2 or SEQ ID NO:5. (If this comparison requires alignment, the sequences should be aligned for maximum homology. "Looped" out sequences from deletions, insertions, or mismatches, are considered differences.) The differences are, preferably, differences or changes at a non-essential residue or a conservative substitution. In a preferred embodiment, the differences are not in the dual specificity phosphatase catalytic domain. In another preferred embodiment one or more differences are at non-active site residues, e.g., amino acids 1–157 or 298–666 of SEQ ID NO:2 or amino acids 1–27 or 174–223 of SEQ ID NO:5.

Other embodiments include a protein that contains one or more changes in amino acid sequence, e.g., a change in an amino acid residue that is not essential for activity. Such 38692 or 21117 proteins differ in amino acid sequence from SEQ ID NO:2 or SEQ ID NO:5, yet retain biological activity.

In one embodiment, the protein includes an amino acid sequence at least about 60%, 65%, 70%, 75%, 80%, 85%, 90%, 95%, 98%, 99% or more homologous to SEQ ID NO:2 or SEQ ID NO:5.

In another embodiment, the protein includes an amino acid sequence at least 55 amino acids in length, and about 60%, 65%, 70%, 75%, 80%, 85%, 90%, 95%, 98%, homologous to SEQ ID NO:2.

In another embodiment, the protein includes an amino acid sequence at least 67 amino acids in length, and about 60%, 65%, 70%, 75%, 80%, 85%, 90%, 95%, 98%, homologous to SEQ ID NO:5.

In another embodiment, a 38692 protein or fragment has an amino acid sequence which differs from the sequence of AAB47561 by at least one, two, three, five or more amino acids. The variations may include the addition, replacement, and/or deletion of amino acid residues.

In another embodiment, a 38692 protein fragment has an amino acid sequence which contains one, preferably more, residues from the sequence of residues 1–115 or 182–223 of SEQ ID NO:5.

A 38692 or 21117 protein or fragment is provided which varies from the sequence of SEQ ID NO:2 or SEQ ID NO:5 in non-active site residues by at least one but by less than 15, 10 or 5 amino acid residues in the protein or fragment, but which does not differ from SEQ ID NO:2 or SEQ ID NO:5 in regions having phosphatase catalytic activity. (If this comparison requires alignment the sequences should be aligned for maximum homology. "Looped" out sequences from deletions, insertions, or mismatches, are considered differences.) In some embodiments, the difference is at a non-essential residue or is a conservative substitution, while in others, the difference is at an essential residue or is a non conservative substitution.

In one embodiment, a biologically active portion of a 38692 or 21117 protein includes a dual specificity phosphatase catalytic domain. Moreover, other biologically active portions, in which other regions of the protein are deleted, can be prepared by recombinant techniques and evaluated for one or more of the functional activities of a native 38692 or 21117 protein.

In a preferred embodiment, the 38692 or 21117 protein has an amino acid sequence shown in SEQ ID NO:2 or SEQ ID NO:5. In other embodiments, the 38692 or 21117 protein is substantially identical to SEQ ID NO:2 or SEQ ID NO:5. In yet another embodiment, the 38692 or 21117 protein is substantially identical to SEQ ID NO:2 or SEQ ID NO:5 and retains the functional activity of the protein of SEQ ID NO:2 or SEQ ID NO:5, as described in detail in subsection I above. Accordingly, in another embodiment, the 38692 or 21117 protein is a protein which includes an amino acid sequence at least about 60%, 65%, 70%, 75%, 80%, 85%, 90%, 95%, 98%, 99% or more identical to SEQ ID NO:2 or SEQ ID NO:5.

38692 or 21117 Chimeric or Fusion Proteins

In another aspect, the invention provides 38692 or 21117 chimeric or fusion proteins. As used herein, a 38692 or 21117 "chimeric protein" or "fusion protein" includes a 38692 or 21117 polypeptide linked to a non-38692 or 21117 polypeptide. A "non-38692 or 21117 polypeptide" refers to a polypeptide having an amino acid sequence corresponding to a protein that is not substantially homologous to the 38692 or 21117 protein, e.g., a protein that is different from the 38692 or 21117 protein and that is derived from the same or a different organism. The 38692 or 21117 polypeptide of the fusion protein can correspond to all or a portion e.g., a fragment described herein of a 38692 or 21117 amino acid sequence. In a preferred embodiment, a 38692 or 21117 fusion protein includes at least one (e.g., two) biologically active portion of a 38692 or 21117 protein. The non-38692 or 21117 polypeptide can be fused to the N-terminus or C-terminus of a 38692 or 21117 polypeptide.

The fusion protein can include a moiety that has high affinity for a ligand. For example, the fusion protein can be a GST-38692 or 21117 fusion protein in which the 38692 or 21117 sequences are fused to the C-terminus of the GST sequences. Such fusion proteins can facilitate the purification of recombinant 38692 or 21117. Alternatively, the fusion protein can be a 38692 or 21117 protein containing a heterologous signal sequence at its N-terminus. In certain host cells (e.g., mammalian host cells), expression and/or secretion of 38692 or 21117 can be increased through use of a heterologous signal sequence.

Fusion proteins can include all or a part of a serum protein, e.g., an IgG constant region, or human serum albumin.

The 38692 or 21117 fusion proteins of the invention can be incorporated into pharmaceutical compositions and administered to a subject in vivo. The 38692 or 21117 fusion proteins can be used to affect the bioavailability of a 38692 or 21117 substrate. 38692 or 21117 fusion proteins may be useful therapeutically for the treatment of disorders caused by, for example: (i) aberrant modification or mutation of a gene encoding a 38692 or 21117 protein; (ii) misregulation of the 38692 or 21117 gene; and (iii) aberrant post-translational modification of a 38692 or 21117 protein.

Moreover, 38692 or 21117-fusion proteins of the invention can be used as immunogens to produce anti-38692 or 21117 antibodies in a subject, to purify 38692 or 21117 ligands, and in screening assays to identify molecules that inhibit the interaction of 38692 or 21117 with a 38692 or 21117 substrate.

Expression vectors are commercially available that already encode a fusion moiety (e.g., a GST polypeptide). A 38692 or 21117-encoding nucleic acid can be cloned into such an expression vector such that the fusion moiety is linked in-frame to the 38692 or 21117 protein.

Variants of 38692 or 21117 Proteins

In another aspect, the invention features a variant of a 38692 or 21117 polypeptide, e.g., a polypeptide that functions as an agonist (mimetic) or as an antagonist of 38692 or 21117 activities. Variants of the 38692 or 21117 proteins can be generated by mutagenesis, e.g., discrete point mutations, the insertion or deletion of sequences or the truncation of a 38692 or 21117 protein. An agonist of the 38692 or 21117 protein retains substantially the same, or a subset, of the biological activities of the naturally occurring form of a 38692 or 21117 protein. An antagonist of a 38692 or 21117 protein can inhibit one or more of the activities of the naturally occurring form of the 38692 or 21117 protein by, for example, competitively modulating a 38692 or 21117-mediated activity of a 38692 or 21117 protein. Thus, specific biological effects can be elicited by treatment with a variant of limited function. Preferably, treatment of a subject with a variant having a subset of the biological activities of the naturally occurring form of the protein has fewer side effects in a subject relative to treatment with the naturally occurring form of the 38692 or 21117 protein.

Variants of a 38692 or 21117 protein can be identified by screening combinatorial libraries of mutants, e.g., truncation mutants, of a 38692 or 21117 protein for agonist or antagonist activity.

Libraries of fragments e.g., N terminal, C terminal, or internal fragments, of a 38692 or 21117 protein coding sequence can be used to generate a variegated population of fragments for screening and subsequent selection of variants of a 38692 or 21117 protein.

Variants in which a cysteine residue is added or deleted or in which a residue that is glycosylated is added or deleted are particularly preferred.

Methods for screening gene products of combinatorial libraries made by point mutations or truncation, and for screening cDNA libraries for gene products having a selected property are known. Recursive ensemble mutagenesis (REM), a new technique which enhances the frequency of functional mutants in the libraries, can be used in combination with screening assays to identify 38692 or 21117 variants (Arkin and Yourvan (1992) *Proc. Natl. Acad. Sci. USA* 89:7811–7815; Delgrave et al. (1993) *Protein Engineering* 6(3):327–331).

Cell based assays can be exploited to analyze a variegated 38692 or 21117 library. For example, a library of expression vectors can be transfected into a cell line, e.g., a cell line, which ordinarily responds to 38692 or 21117 in a substrate-dependent manner. The transfected cells are then contacted with 38692 or 21117 and the effect of the expression of the mutant on signaling by a 38692 or 21117 substrate can be detected, e.g., by measuring phosphorylation of serine or threonine residues. Plasmid DNA can then be recovered from the cells that score for inhibition, or alternatively, potentiation of signaling by the 38692 or 21117 substrate, and the individual clones further characterized.

In another aspect, the invention features a method of making a 38692 or 21117 polypeptide, e.g., a peptide having a non-wild type activity, e.g., an antagonist, agonist, or super agonist of a naturally occurring 38692 or 21117 polypeptide, e.g., a naturally occurring 38692 or 21117 polypeptide. The method includes: altering the sequence of a 38692 or 21117 polypeptide, e.g., by substitution or deletion of one or more residues of a non-conserved region, a domain, or residue disclosed herein, and testing the altered polypeptide for the desired activity.

In another aspect, the invention features a method of making a fragment or analog of a 38692 or 21117 polypeptide that retains at least one biological activity of a naturally occurring 38692 or 21117 polypeptide. The method includes: altering the sequence, e.g., by substitution or deletion of one or more residues, of a 38692 or 21117 polypeptide, e.g., altering the sequence of a non-conserved region, or a domain or residue described herein, and testing the altered polypeptide for the desired activity.

Anti-38692 or 21117 Antibodies

In another aspect, the invention provides an anti-38692 or 21117 antibody, or a fragment thereof (e.g., an antigen-binding fragment thereof). The term "antibody" as used herein refers to an immunoglobulin molecule or immunologically active portion thereof, i.e., an antigen-binding portion. As used herein, the term "antibody" refers to a protein comprising at least one, and preferably two, heavy (H) chain variable regions (abbreviated herein as VH), and at least one and preferably two light (L) chain variable regions (abbreviated herein as VL). The VH and VL regions can be further subdivided into regions of hypervariability, termed "complementarity determining regions" ("CDR"), interspersed with regions that are more conserved, termed "framework regions" (FR). The extent of the framework region and CDR's has been precisely defined (see, Kabat et al. (1991) *Sequences of Proteins of Immunological Interest, Fifth Edition,* U.S. Department of Health and Human Services, NIH Publication No. 91–3242, and Chothia et al. (1987) *J. Mol. Biol.* 196:901–917, which are incorporated herein by reference). Each VH and VL is composed of three CDR's and four FRs, arranged from amino-terminus to carboxy-terminus in the following order: FR1, CDR1, FR2, CDR2, FR3, CDR3, FR4.

The anti-38692 or 21117 antibody can further include a heavy and light chain constant region, to thereby form a heavy and light immunoglobulin chain, respectively. In one embodiment, the antibody is a tetramer of two heavy immunoglobulin chains and two light immunoglobulin chains, wherein the heavy and light immunoglobulin chains are inter-connected by, e.g., disulfide bonds. The heavy chain constant region is comprised of three domains, CH1, CH2 and CH3. The light chain constant region is comprised of one domain, CL. The variable region of the heavy and light chains contains a binding domain that interacts with an antigen. The constant regions of the antibodies typically mediate the binding of the antibody to host tissues or factors, including various cells of the immune system (e.g., effector cells) and the first component (Clq) of the classical complement system.

As used herein, the term "immunoglobulin" refers to a protein consisting of one or more polypeptides substantially encoded by immunoglobulin genes. The recognized human immunoglobulin genes include the kappa, lambda, alpha (IgA 1 and IgA2), gamma (IgG1, IgG2, IgG3, IgG4), delta, epsilon and mu constant region genes, as well as the myriad immunoglobulin variable region genes. Full-length immunoglobulin "light chains" (about 25 Kd or 214 amino acids) are encoded by a variable region gene at the NH2-terminus (about 110 amino acids) and a kappa or lambda constant region gene at the COOH—terminus. Full-length immunoglobulin "heavy chains" (about 50 Kd or 446 amino acids), are similarly encoded by a variable region gene (about 116 amino acids) and one of the other aforementioned constant region genes, e.g., gamma (encoding about 330 amino acids).

The term "antigen-binding fragment" of an antibody (or simply "antibody portion," or "fragment"), as used herein, refers to one or more fragments of a full-length antibody that retain the ability to specifically bind to the antigen, e.g., 38692 or 21117 polypeptide or fragment thereof. Examples of antigen-binding fragments of the anti-38692 or 21117 antibody include, but are not limited to: (i) a Fab fragment, a monovalent fragment consisting of the VL, VH, CL and CH1 domains; (ii) a F(ab')$_2$ fragment, a bivalent fragment comprising two Fab fragments linked by a disulfide bridge at the hinge region; (iii) a Fd fragment consisting of the VH and CH1 domains; (iv) a Fv fragment consisting of the VL and VH domains of a single arm of an antibody, (v) a dAb fragment (Ward et al., (1989) *Nature* 341:544–546), which consists of a VH domain; and (vi) an isolated complementarity determining region (CDR). Furthermore, although the two domains of the Fv fragment, VL and VH, are coded for by separate genes, they can be joined, using recombinant methods, by a synthetic linker that enables them to be made as a single protein chain in which the VL and VH regions pair to form monovalent molecules (known as single chain Fv (scFv); see e.g., Bird et al. (1988) *Science* 242:423–426; and Huston et al. (1988) *Proc. Natl. Acad. Sci. USA* 85:5879–5883). Such single chain antibodies are also encompassed within the term "antigen-binding fragment" of an antibody. These antibody fragments are obtained using conventional techniques known to those with skill in the art, and the fragments are screened for utility in the same manner as are intact antibodies.

The anti-38692 or 21117 antibody can be a polyclonal or a monoclonal antibody. In other embodiments, the antibody can be recombinantly produced, e.g., produced by phage display or by combinatorial methods.

Phage display and combinatorial methods for generating anti-38692 or 21117 antibodies are known in the art (as described in, e.g., Ladner et al. U.S. Pat. No. 5,223,409; Kang et al. International Publication No. WO 92/18619; Dower et al. International Publication No. WO 91/17271; Winter et al. International Publication WO 92/20791; Markland et al. International Publication No. WO 92/15679; Breitling et al. International Publication WO 93/01288; McCafferty et al. International Publication No. WO 92/01047; Garrard et al. International Publication No. WO 92/09690; Ladner et al. International Publication No. WO 90/02809; Fuchs et al. (1991) *Bio/Technology* 9:1370–1372; Hay et al. (1992) *Hum Antibod Hybridomas* 3:81–85; Huse et al. (1989) *Science* 246:1275–1281; Griffths et al. (1993)

EMBO J 12:725–734; Hawkins et al. (1992) *J Mol Biol* 226:889–896; Clackson et al. (1991) *Nature* 352:624–628; Gram et al. (1992) *PNAS* 89:3576–3580; Garrad et al. (1991) *Bio/Technology* 9:1373–1377; Hoogenboom et al. (1991) *Nuc Acid Res* 19:4133–4137; and Barbas et al. (1991) *PNAS* 88:7978–7982, the contents of all of which are incorporated by reference herein).

In one embodiment, the anti-38692 or 21117 antibody is a fully human antibody (e.g., an antibody made in a mouse which has been genetically engineered to produce an antibody from a human immunoglobulin sequence), or a non-human antibody, e.g., a rodent (mouse or rat), goat, primate (e.g., monkey), camel antibody. Preferably, the non-human antibody is a rodent (mouse or rat antibody). Method of producing rodent antibodies are known in the art.

Human monoclonal antibodies can be generated using transgenic mice carrying the human immunoglobulin genes rather than the mouse system. Splenocytes from these transgenic mice immunized with the antigen of interest are used to produce hybridomas that secrete human mAbs with specific affinities for epitopes from a human protein (see, e.g., Wood et al. International Application WO 91/00906, Kucherlapati et al. PCT publication WO 91/10741; Lonberg et al. International Application WO 92/03918; Kay et al. International Application 92/03917; Lonberg, N. et al. 1994 *Nature* 368:856–859; Green, L. L. et al. 1994 *Nature Genet.* 7:13–21; Morrison, S. L. et al. 1994 *Proc. Natl. Acad. Sci. USA* 81:6851–6855; Bruggeman et al. 1993 *Year Immunol* 7:33–40; Tuaillon et al. 1993 *PNAS* 90:3720–3724; Bruggeman et al. 1991 *Eur J Immunol* 21:1323–1326).

An anti-38692 or 21117 antibody can be one in which the variable region, or a portion thereof, e.g., the CDR's, are generated in a non-human organism, e.g., a rat or mouse. Chimeric, CDR-grafted, and humanized antibodies are within the invention. Antibodies generated in a non-human organism, e.g., a rat or mouse, and then modified, e.g., in the variable framework or constant region, to decrease antigenicity in a human are within the invention.

Chimeric antibodies can be produced by recombinant DNA techniques known in the art. For example, a gene encoding the Fc constant region of a murine (or other species) monoclonal antibody molecule is digested with restriction enzymes to remove the region encoding the murine Fc, and the equivalent portion of a gene encoding a human Fc constant region is substituted (see Robinson et al., International Patent Publication PCT/US86/02269; Akira, et al., European Patent Application 184,187; Taniguchi, M., European Patent Application 171,496; Morrison et al., European Patent Application 173,494; Neuberger et al., International Application WO 86/01533; Cabilly et al. U.S. Pat. No. 4,816,567; Cabilly et al., European Patent Application 125, 023; Better et al. (1988 *Science* 240:1041–1043); Liu et al. (1987) *PNAS* 84:3439–3443; Liu et al., 1987, *J. Immunol.* 139:3521–3526; Sun et al. (1987) *PNAS* 84:214–218; Nishimura et al., 1987, *Canc. Res.* 47:999–1005; Wood et al. (1985) *Nature* 314:446–449; and Shaw et al., 1988, *J. Natl Cancer Inst.* 80:1553–1559).

A humanized or CDR-grafted antibody will have at least one or two but generally all three recipient CDR's (of heavy and or light immuoglobulin chains) replaced with a donor CDR. The antibody may be replaced with at least a portion of a non-human CDR or only some of the CDR's may be replaced with non-human CDR's. It is only necessary to replace the number of CDR's required for binding of the humanized antibody to a 38692 or 21117 or a fragment thereof. Preferably, the donor will be a rodent antibody, e.g., a rat or mouse antibody, and the recipient will be a human framework or a human consensus framework. Typically, the immunoglobulin providing the CDR's is called the "donor" and the immunoglobulin providing the framework is called the "acceptor." In one embodiment, the donor immunoglobulin is a non-human (e.g., rodent). The acceptor framework is a naturally-occurring (e.g., a human) framework or a consensus framework, or a sequence about 85% or higher, preferably 90%, 95%, 99% or higher identical thereto.

As used herein, the term "consensus sequence" refers to the sequence formed from the most frequently occurring amino acids (or nucleotides) in a family of related sequences (See e.g., Winnaker, From Genes to Clones (Verlagsgesellschaft, Weinheim, Germany 1987). In a family of proteins, each position in the consensus sequence is occupied by the amino acid occurring most frequently at that position in the family. If two amino acids occur equally frequently, either can be included in the consensus sequence. A "consensus framework" refers to the framework region in the consensus immunoglobulin sequence.

An antibody can be humanized by methods known in the art. Humanized antibodies can be generated by replacing sequences of the Fv variable region which are not directly involved in antigen binding with equivalent sequences from human Fv variable regions. General methods for generating humanized antibodies are provided by Morrison, S. L., 1985, *Science* 229:1202–1207, by Oi et al., 1986, *Bio Techniques* 4:214, and by Queen et al. U.S. Pat. No. 5,585, 089, U.S. Pat. No. 5,693,761 and U.S. Pat. No. 5,693,762, the contents of all of which are hereby incorporated by reference. Those methods include isolating, manipulating, and expressing the nucleic acid sequences that encode all or part of immunoglobulin Fv variable regions from at least one of a heavy or light chain. Sources of such nucleic acid are well known to those skilled in the art and, for example, may be obtained from a hybridoma producing an antibody against a 38692 or 21117 polypeptide or fragment thereof. The recombinant DNA encoding the humanized antibody, or fragment thereof, can then be cloned into an appropriate expression vector.

Humanized or CDR-grafted antibodies can be produced by CDR-grafting or CDR substitution, wherein one, two, or all CDR's of an immunoglobulin chain can be replaced. See e.g., U.S. Pat. No. 5,225,539; Jones et al. 1986 *Nature* 321:552–525; Verhoeyan et al. 1988 *Science* 239:1534; Beidler et al. 1988 *J. Immunol.* 141:4053–4060; Winter U.S. Pat. No. 5,225,539, the contents of all of which are hereby expressly incorporated by reference. Winter describes a CDR-grafting method which may be used to prepare the humanized antibodies of the present invention (UK Patent Application GB 2188638A, filed on Mar. 26, 1987; Winter U.S. Pat. No. 5,225,539), the contents of which is expressly incorporated by reference.

Also within the scope of the invention are humanized antibodies in which specific amino acids have been substituted, deleted or added. Preferred humanized antibodies have amino acid substitutions in the framework region, such as to improve binding to the antigen. For example, a humanized antibody will have framework residues identical to the donor framework residue or to another amino acid other than the recipient framework residue. To generate such antibodies, a selected, small number of acceptor framework residues of the humanized immunoglobulin chain can be replaced by the corresponding donor amino acids. Preferred locations of the substitutions include amino acid residues adjacent to the CDR, or which are capable of interacting with a CDR (see e.g., U.S. Pat. No. 5,585,089). Criteria for selecting amino acids from the donor are described in U.S.

Pat. No. 5,585,089, e.g., columns 12–16 of U.S. Pat. No. 5,585,089, the e.g., columns 12–16 of U.S. Pat. No. 5,585,089, the contents of which are hereby incorporated by reference. Other techniques for humanizing antibodies are described in Padlan et al. EP 519596 A1, published on December 23, 1992.

In preferred embodiments an antibody can be made by immunizing with purified 38692 or 21117 antigen, or a fragment thereof, e.g., a fragment described herein.

A full-length 38692 or 21117 protein or, antigenic peptide fragment of 38692 or 21117 can be used as an immunogen or can be used to identify anti-38692 or 21117 antibodies made with other immunogens, e.g., cells, membrane preparations, and the like. The antigenic peptide of 38692 or 21117 should include at least 8 amino acid residues of the amino acid sequence shown in SEQ ID NO:2 or SEQ ID NO:5 and encompass an epitope of 38692 or 21117. Preferably, the antigenic peptide includes at least 10 amino acid residues, more preferably at least 15 amino acid residues, even more preferably at least 20 amino acid residues, and most preferably at least 30 amino acid residues.

Fragments of 21117 which include residues about 592–633 can be used to make, e.g., used as immunogens or used to characterize the specificity of an antibody, antibodies against hydrophilic regions of the 21117 protein. Similarly, fragments of 21117 which include residues 91–106 can be used to make an antibody against a hydrophobic region of the 21117 protein; a fragment of 21117 which includes residues about 158 to 297 can be used to make an antibody against the phosphatase region of the 21117 protein.

Fragments of 38692 which include residues about 200–212 can be used to make, e.g., used as immunogens or used to characterize the specificity of an antibody, antibodies against hydrophilic regions of the 38692 protein. Similarly, fragments of 38692 which include residues 31–41 be used to make an antibody against a hydrophobic region of the 38692 protein; a fragment of 38692 which includes residues about 28–173 can be used to make an antibody against the phosphatase region of the 38692 protein.

Antibodies reactive with, or specific for, any of these regions, or other regions or domains described herein are provided.

Antibodies which bind only native 38692 or 21117 protein, only denatured or otherwise non-native 38692 or 21117 protein, or which bind both, are with in the invention. Antibodies with linear or conformational epitopes are within the invention. Confromational epitopes can sometimes be identified by indentifying antibodies which bind to native but not denatured 38692 or 21117 protein.

Preferred epitopes encompassed by the antigenic peptide are regions of 38692 or 21117 are located on the surface of the protein, e.g., hydrophilic regions, as well as regions with high antigenicity. For example, an Emini surface probability analysis of the human 38692 or 21117 protein sequence can be used to indicate the regions that have a particularly high probability of being localized to the surface of the 38692 or 21117 protein and are thus likely to constitute surface residues useful for targeting antibody production.

In preferred embodiments antibodies can bind one or more of purified antigen; tissue, e.g., tissue sections; whole cells, preferably living cells; lysed cells; cell fractions.

The anti-38692 or 21117 antibody can be a single chain antibody. A single-chain antibody (scFV) may be engineered (see, for example, Colcher et al. (1999) *Ann N Y Acad Sci* 880:263–80; and Reiter (1996) *Clin Cancer Res* 2:245–52). The single chain antibody can be dimerized or multimerized to generate multivalent antibodies having specificities for different epitopes of the same target 38692 or 21117 protein.

In a preferred embodiment the antibody has: effector function; and can fix complement. In other embodiments the antibody does not; recruit effector cells; or fix complement.

In a preferred embodiment, the antibody has reduced or no ability to bind an Fc receptor. For example., it is a isotype or subtype, fragment or other mutant, which does not support binding to an Fc receptor, e.g., it has a mutagenized or deleted Fc receptor binding region.

The antibody can be coupled to a toxin, e.g., a polypeptide toxin, e,g, ricin or diptheria toxin or active fragment hereof, or a radionuclide, or imaging agent, e.g. a radioactive, enzymatic, or other, e.g., imaging agent, e.g., a NMR contrast agent. Labels which produce detectable radioactive emissions or fluorescence are preferred.

An anti-38692 or 21117 antibody (e.g., monoclonal antibody) can be used to isolate 38692 or 21117 by standard techniques, such as affinity chromatography or immunoprecipitation. Moreover, an anti-38692 or 21117 antibody can be used to detect 38692 or 21117 protein (e.g., in a cellular lysate or cell supernatant) in order to evaluate the abundance and pattern of expression of the protein. Anti-38692 or 21117 antibodies can be used diagnostically to monitor protein levels in tissue as part of a clinical testing procedure, e.g., to determine the efficacy of a given treatment regimen. Detection can be facilitated by coupling (i.e., physically linking) the antibody to a detectable substance (i.e., antibody labelling). Examples of detectable substances include various enzymes, prosthetic groups, fluorescent materials, luminescent materials, bioluminescent materials, and radioactive materials. Examples of suitable enzymes include horseradish peroxidase, alkaline phosphatase, β-galactosidase, or acetylcholinesterase; examples of suitable prosthetic group complexes include streptavidin/biotin and avidin/biotin; examples of suitable fluorescent materials include umbelliferone, fluorescein, fluorescein isothiocyanate, rhodamine, dichlorotriazinylamine fluorescein, dansyl chloride or phycoerythrin; an example of a luminescent material includes luminol; examples of bioluminescent materials include luciferase, luciferin, and aequorin, and examples of suitable radioactive material include $^{125}I$, $^{131}I$, $^{35}S$ or $^{3}H$.

The invention also includes a nucleic acid that encodes an anti-38692 or 21117 antibody, e.g., an anti-38692 or 21117 antibody described herein. Also included are vectors which include the nucleic acid and cells transformed with the nucleic acid, particularly cells which are useful for producing an antibody, e.g., mammalian cells, e.g. CHO or lymphatic cells.

The invention also includes cell lines, e.g., hybridomas, which make an anti-38692 or 21117 antibody, e.g., and antibody described herein, and method of using said cells to make a 38692 or 21117 antibody.

Recombinant Expression Vectors Host Cells and Genetically Engineered Cells

In another aspect, the invention includes, vectors, preferably expression vectors, containing a nucleic acid encoding a polypeptide described herein. As used herein, the term "vector" refers to a nucleic acid molecule capable of transporting another nucleic acid to which it has been linked and can include a plasmid, cosmid or viral vector. The vector can be capable of autonomous replication or it can integrate into a host DNA. Viral vectors include, e.g., replication defective retroviruses, adeno-viruses and adeno-associated viruses.

A vector can include a 38692 or 21117 nucleic acid in a form suitable for expression of the nucleic acid in a host cell. Preferably, the recombinant expression vector includes one or more regulatory sequences operatively linked to the nucleic acid sequence to be expressed. The term "regulatory sequence" includes promoters, enhancers and other expression control elements (e.g., polyadenylation signals). Regulatory sequences include those that direct constitutive expression of a nucleotide sequence, as well as tissue-specific regulatory and/or inducible sequences. The design of the expression vector can depend on such factors as the choice of the host cell to be transformed, the level of expression of protein desired, and the like. The expression vectors of the invention can be introduced into host cells to thereby produce proteins or polypeptides, including fusion proteins or polypeptides, encoded by nucleic acids as described herein (e.g., 38692 or 21117 proteins, mutant forms of 38692 or 21117 proteins, fusion proteins, and the like).

The recombinant expression vectors of the invention can be designed for expression of 38692 or 21117 proteins in prokaryotic or eukaryotic cells. For example, polypeptides of the invention can be expressed in E. coli, insect cells (e.g., using baculovirus expression vectors), yeast cells or mammalian cells. Suitable host cells are discussed further in Goeddel, Gene Expression Technology: Methods in Enzymology 185, Academic Press, San Diego, Calif. (1990). Alternatively, the recombinant expression vector can be transcribed and translated in vitro, for example using T7 promoter regulatory sequences and T7 polymerase.

Expression of proteins in prokaryotes is most often carried out in E. coli with vectors containing constitutive or inducible promoters directing the expression of either fusion or non-fusion proteins. Fusion vectors add a number of amino acids to a protein encoded therein, usually to the amino terminus of the recombinant protein. Such fusion vectors typically serve three purposes: (1) to increase expression of recombinant protein; (2) to increase the solubility of the recombinant protein; and (3) to aid in the purification of the recombinant protein by acting as a ligand in affinity purification. Often, a proteolytic cleavage site is introduced at the junction of the fusion moiety and the recombinant protein to enable separation of the recombinant protein from the fusion moiety subsequent to purification of the fusion protein. Such enzymes, and their cognate recognition sequences, include Factor Xa, thrombin and enterokinase. Typical fusion expression vectors include pGEX (Pharmacia Biotech Inc; Smith, D. B. and Johnson, K. S. (1988) Gene 67:31–40), pMAL (New England Biolabs, Beverly, Mass.) and pRIT5 (Pharmacia, Piscataway, N.J.), which fuse glutathione S-transferase (GST), maltose E binding protein, and protein A, respectively, to the target recombinant protein.

Purified fusion proteins can be used in 38692 or 21117 activity assays, (e.g., direct assays or competitive assays described in detail below), or to generate antibodies specific for 38692 or 21117 proteins. In a preferred embodiment, a fusion protein expressed in a retroviral expression vector of the present invention can be used to infect bone marrow cells that are subsequently transplanted into irradiated recipients. The pathology of the subject recipient is then examined after sufficient time has passed (e.g., six weeks).

To maximize recombinant protein expression in E. coli is to express the protein in a host bacteria with an impaired capacity to proteolytically cleave the recombinant protein (Gottesman, S., Gene Expression Technology: Methods in Enzymology 185, Academic Press, San Diego, Calif. (1990) 119–128). Another strategy is to alter the nucleic acid sequence of the nucleic acid to be inserted into an expression vector so that the individual codons for each amino acid are those preferentially utilized in E. coli (Wada et al., (1992) Nucleic Acids Res. 20:2111–2118). Such alteration of nucleic acid sequences of the invention can be carried out by standard DNA synthesis techniques.

A 38692 or 21117 expression vector can be a yeast expression vector, a vector for expression in insect cells, e.g., a baculovirus expression vector or a vector suitable for expression in mammalian cells.

When used in mammalian cells, the expression vector's control functions are often provided by viral regulatory elements. For example, commonly used promoters are derived from polyoma, Adenovirus 2, cytomegalovirus and Simian Virus 40.

In another embodiment, the recombinant mammalian expression vector is capable of directing expression of the nucleic acid preferentially in a particular cell type (e.g., tissue-specific regulatory elements are used to express the nucleic acid). Non-limiting examples of suitable tissue-specific promoters include the albumin promoter (liver-specific; Pinkert et al. (1987) Genes Dev. 1:268–277), lymphoid-specific promoters (Calame and Eaton (1988) Adv. Immunol. 43:235–275), in particular promoters of T cell receptors (Winoto and Baltimore (1989) EMBO J. 8:729–733) and immunoglobulins (Banerji et al. (1983) Cell 33:729–740; Queen and Baltimore (1983) Cell 33:741–748), neuron-specific promoters (e.g., the neurofilament promoter; Byrne and Ruddle (1989) Proc. Natl. Acad. Sci. USA 86:5473–5477), pancreas-specific promoters (Edlund et al. (1985) Science 230:912–916), and mammary gland-specific promoters (e.g., milk whey promoter; U.S. Pat. No. 4,873, 316 and European Application Publication No. 264,166). Developmentally regulated promoters are also encompassed, including for example, the murine hox promoters (Kessel and Gruss (1990) Science 249:374–379) and the α-fetoprotein promoter (Campes and Tilghman (1989) Genes Dev. 3:537–546).

The invention further provides a recombinant expression vector comprising a DNA molecule of the invention cloned into the expression vector in an antisense orientation. Regulatory sequences (e.g., viral promoters and/or enhancers) operatively linked to a nucleic acid cloned in the antisense orientation can be chosen which direct the constitutive, tissue specific or cell type specific expression of antisense RNA in a variety of cell types. The antisense expression vector can be in the form of a recombinant plasmid, phagemid or attenuated virus. For a discussion of the regulation of gene expression using antisense genes see Weintraub, H. et al., Antisense RNA as a molecular tool for genetic analysis, Reviews—Trends in Genetics, Vol. 1(1) 1986.

Another aspect the invention provides a host cell that includes a nucleic acid molecule described herein, e.g., a 38692 or 21117 nucleic acid molecule within a recombinant expression vector or a 38692 or 21117 nucleic acid molecule containing sequences which allow it to homologously recombine into a specific site of the host cell's genome. The terms "host cell" and "recombinant host cell" are used interchangeably herein. Such terms refer not only to the particular subject cell, but to the progeny or potential progeny of such a cell. Because certain modifications may occur in succeeding generations due to either mutation or environmental influences, such progeny may not, in fact, be identical to the parent cell, but are still included within the scope of the term as used herein.

A host cell can be any prokaryotic or eukaryotic cell. For example, a 38692 or 21117 protein can be expressed in bacterial cells such as E. coli, insect cells, yeast or mammalian cells (such as CHO or COS cells). Other suitable host cells are known to those skilled in the art.

Vector DNA can be introduced into host cells via conventional transformation or transfection techniques. As used herein, the terms "transformation" and "transfection" are intended to refer to a variety of art-recognized techniques for introducing foreign nucleic acid (e.g., DNA) into a host cell, including calcium phosphate or calcium chloride co-precipitation, DEAE-dextran-mediated transfection, lipofection, or electroporation A host cell of the invention can be used to produce (i.e., express) a 38692 or 21117 protein. Accordingly, the invention further provides methods for producing a 38692 or 21117 protein using the host cells of the invention. In one embodiment, the method includes culturing the host cell of the invention (into which a recombinant expression vector encoding a 38692 or 21117 protein has been introduced) in a suitable medium such that a 38692 or 21117 protein is produced. In another embodiment, the method further includes isolating a 38692 or 21117 protein from the medium or the host cell.

In another aspect, the invention features a cell or purified preparation of cells that include a 38692 or 21117 transgene, or which otherwise misexpress 38692 or 21117. The cell preparation can consist of human or non-human cells, e.g., rodent cells such as mouse or rat cells, rabbit cells, or pig cells. In preferred embodiments, the cell or cells include a 38692 or 21117 transgene, e.g., a heterologous form of a 38692 or 21117 nucleic acid, e.g., a gene derived from humans (in the case of a non-human cell). The 38692 or 21117 transgene can be misexpressed, e.g., overexpressed or underexpressed. In other preferred embodiments, the cell or cells include a gene that misexpresses an endogenous 38692 or 21117 nucleic acid, e.g., disruption in the expression of a gene, e.g., a knockout. Such cells can serve as a model for studying disorders that are related to mutated or misexpressed 38692 or 21117 alleles or for use in drug screening.

In another aspect, the invention features, a human cell, e.g., a hematopoietic stem cell, transformed with nucleic acid that encodes a 38692 or 21117 polypeptide.

Also provided are cells (e.g., human cells, e.g., a hematopoietic cell or a fibroblast cell), or a purified preparation thereof, in which an endogenous 38692 or 21117 is under the control of a regulatory sequence that does not normally control the expression of the endogenous 38692 or 21117 gene. The expression characteristics of an endogenous gene within a cell, e.g., a cell line or microorganism, can be modified by inserting a heterologous DNA regulatory element into the genome of the cell such that the inserted regulatory element is operably linked to the endogenous 38692 or 21117 gene. For example, an endogenous 38692 or 21117 gene, e.g., a gene that is "transcriptionally silent," e.g., not normally expressed, or expressed only at very low levels, may be activated by inserting a regulatory element that is capable of promoting the expression of a normally expressed gene product in that cell. Techniques such as targeted homologous recombinations, can be used to insert the heterologous DNA as described in, e.g., Chappel, U.S. Pat. No. 5,272,071; WO 91/06667, published in May 16, 1991.

In a preferred embodiment, recombinant cells described herein can be used for replacement therapy in a subject. For example, a nucleic acid encoding a 38692 or 21117 polypeptide operably linked to an inducible promoter (e.g., a steroid hormone receptor-regulated promoter) is introduced into a human or nonhuman, e.g., mammalian, e.g., porcine recombinant cell. The cell is cultivated and encapsulated in a biocompatible material, such as poly-lysine alginate, and subsequently implanted into the subject. See, e.g., Lanza (1996) Nat. Biotechnol. 14:1107; Joki et al. (2001) Nat. Biotechnol. 19:35; and U.S. Pat. No. 5,876,742. Production of 38692 or 21117 polypeptide can be regulated in the subject by administering an agent (e.g., a steroid hormone) to the subject. In another preferred embodiment, the implanted recombinant cells express and secrete an antibody specific for a 38692 or 21117 polypeptide. The antibody can be any antibody or any antibody derivative described herein.

Transgenic Animals

The invention provides non-human transgenic animals. Such animals are useful for studying the function and/or activity of a 38692 or 21117 protein and for identifying and/or evaluating modulators of 38692 or 21117 activity. As used herein, a "transgenic animal" is a non-human animal, preferably a mammal, more preferably a rodent such as a rat or mouse, in which one or more of the cells of the animal include a transgene. Other examples of transgenic animals include non-human primates, sheep, dogs, cows, goats, chickens, amphibians, and the like. A transgene is exogenous DNA or a rearrangment, e.g., a deletion of endogenous chromosomal DNA, which preferably is integrated into or occurs in the genome of the cells of a transgenic animal. A transgene can direct the expression of an encoded gene product in one or more cell types or tissues of the transgenic animal, other transgenes, e.g., a knockout, reduce expression. Thus, a transgenic animal can be one in which an endogenous 38692 or 21117 gene has been altered by, e.g., by homologous recombination between the endogenous gene and an exogenous DNA molecule introduced into a cell of the animal, e.g., an embryonic cell of the animal, prior to development of the animal.

Intronic sequences and polyadenylation signals can also be included in the transgene to increase the efficiency of expression of the transgene. A tissue-specific regulatory sequence(s) can be operably linked to a transgene of the invention to direct expression of a 38692 or 21117 protein to particular cells. A transgenic founder animal can be identified based upon the presence of a 38692 or 21117 transgene in its genome and/or expression of 38692 or 21117 mRNA in tissues or cells of the animals. A transgenic founder animal can then be used to breed additional animals carrying the transgene. Moreover, transgenic animals carrying a transgene encoding a 38692 or 21117 protein can further be bred to other transgenic animals carrying other transgenes.

38692 or 21117 proteins or polypeptides can be expressed in transgenic animals or plants, e.g., a nucleic acid encoding the protein or polypeptide can be introduced into the genome of an animal. In preferred embodiments the nucleic acid is placed under the control of a tissue specific promoter, e.g., a milk or egg specific promoter, and recovered from the milk or eggs produced by the animal. Suitable animals are mice, pigs, cows, goats, and sheep.

The invention also includes a population of cells from a transgenic animal, as discussed herein.

Uses

The nucleic acid molecules, proteins, protein homologues, and antibodies described herein can be used in one or more of the following methods: (a) screening assays; (b) predictive medicine (e.g., diagnostic assays, prognostic assays, monitoring clinical trials, and pharmacogenetics); and (c) methods of treatment (e.g., therapeutic and prophylactic). The isolated nucleic acid molecules of the invention can be used, for example, to express a 38692 or 21117 protein (e.g., via a recombinant expression vector in a host cell in gene therapy applications), to detect a 38692 or 21117 mRNA (e.g., in a biological sample) or a genetic alteration in a 38692 or 21117 gene, and to modulate 38692 or 21117 activity, as described further below. The 38692 or 21117 proteins can be used to treat disorders characterized by insufficient or excessive production of a 38692 or 21117 substrate or production of 38692 or 21117 inhibitors. In addition, the 38692 or 21117 proteins can be used to screen for naturally occurring 38692 or 21117 substrates, to screen for drugs or compounds that modulate 38692 or 21117 activity, as well as to treat disorders characterized by insufficient or excessive production of 38692 or 21117 protein or production of 38692 or 21117 protein forms which have decreased, aberrant or unwanted activity compared to 38692 or 21117 wild type protein (e.g., imbalance of protein serine/threonine kinase and protein serine/threonine phosphorylase activities, leading to an increase or decrease in lipid biosynthesis, such as cholesterol or cell cycle progression and neoplastic transformation). Moreover, the anti-38692 or 21117 antibodies of the invention can be used to detect and isolate 38692 or 21117 proteins, regulate the bioavailability of 38692 or 21117 proteins, and modulate 38692 or 21117 activity.

A method of evaluating a compound for the ability to interact with, e.g., bind, a subject 38692 or 21117 polypeptide is provided. The method includes: contacting the compound with the subject 38692 or 21117 polypeptide; and evaluating ability of the compound to interact with, e.g., to bind or form a complex with the subject 38692 or 21117 polypeptide. This method can be performed in vitro, e.g., in a cell free system, or in vivo, e.g., in a two-hybrid interaction trap assay. This method can be used to identify naturally occurring molecules that interact with a subject 38692 or 21117 polypeptide. It can also be used to find natural or synthetic inhibitors of a subject 38692 or 21117 polypeptide. Screening methods are discussed in more detail below.

Screening Assays

The invention provides methods (also referred to herein as "screening assays") for identifying modulators, i.e., candidate or test compounds or agents (e.g., proteins, peptides, peptidomimetics, peptoids, small molecules or other drugs) that bind to 38692 or 21117 proteins, have a stimulatory or inhibitory effect on, for example, 38692 or 21117 expression or 38692 or 21117 activity, or have a stimulatory or inhibitory effect on, for example, the expression or activity of a 38692 or 21117 substrate. Compounds thus identified can be used to modulate the activity of target gene products (e.g., 38692 or 21117 genes) in a therapeutic protocol, to elaborate the biological function of the target gene product, or to identify compounds that disrupt normal target gene interactions.

In one embodiment, the invention provides assays for screening candidate or test compounds that are substrates of a 38692 or 21117 protein or polypeptide or a biologically active portion thereof. In another embodiment, the invention provides assays for screening candidate or test compounds that bind to or modulate the activity of a 38692 or 21117 protein or polypeptide or a biologically active portion thereof.

In any screening assay, a 38692 or 21117 polypeptide that may have, e.g., a phosphatase domain, can be used.

The test compounds of the present invention can be obtained using any of the numerous approaches in combinatorial library methods known in the art, including: biological libraries; peptoid libraries [libraries of molecules having the functionalities of peptides, but with a novel, non-peptide backbone which are resistant to enzymatic degradation but which nevertheless remain bioactive] (see, e.g., Zuckermann, R. N. et al. *J. Med. Chem.* 1994, 37: 2678–85); spatially addressable parallel solid phase or solution phase libraries; synthetic library methods requiring deconvolution; the 'one-bead one-compound' library method; and synthetic library methods using affinity chromatography selection. The biological library and peptoid library approaches are limited to peptide libraries, while the other four approaches are applicable to peptide, non-peptide oligomer or small molecule libraries of compounds (Lam, K. S. (1997) *Anticancer Drug Des.* 12:145).

Examples of methods for the synthesis of molecular libraries can be found in the art, for example in: DeWitt et al. (1993) *Proc. Natl. Acad. Sci. U.S.A.* 90:6909; Erb et al. (1994) *Proc. Natl. Acad. Sci. USA* 91:11422; Zuckermann et al. (1994). *J. Med. Chem.* 37:2678; Cho et al. (1993) *Science* 261:1303; Carrell et al. (1994) *Angew. Chem. Int. Ed. Engl.* 33:2059; Carell et al. (1994) *Angew. Chem. Int. Ed. Engl.* 33:2061; and in Gallop et al. (1994) *J. Med. Chem.* 37:1233.

Libraries of compounds may be presented in solution (e.g., Houghten (1992) *Biotechniques* 13:412–421), or on beads (Lam (1991) *Nature* 354:82–84), chips (Fodor (1993) *Nature* 364:555–556), bacteria or spores (Ladner U.S. Pat. No. 5,223,409), plasmids (Cull et al. (1992) *Proc. Natl. Acad. Sci. USA* 89:1865–1869) or on phage (Scott and Smith (1990) *Science* 249:386–390); (Devlin (1990) *Science* 249:404–406); (Cwirla et al. (1990) *Proc. Natl. Acad Sci.* 87:6378–6382); (Felici (1991) *J. Mol. Biol.* 222:301–310); (Ladner supra.).

In one embodiment, an assay is a cell-based assay in which a cell that expresses a 38692 or 21117 protein or biologically active portion thereof is contacted with a test compound, and the ability of the test compound to modulate 38692 or 21117 activity is determined. Determining the ability of the test compound to modulate 38692 or 21117 activity can be accomplished by monitoring, for example, phosphatase activity. The cell, for example, can be of mammalian origin, e.g., human.

The ability of the test compound to modulate 38692 or 21117 binding to a compound, e.g., a 38692 or 21117 substrate, or to bind to 38692 or 21117 can also be evaluated. This can be accomplished, for example, by coupling the compound, e.g., the substrate with a radioisotope or enzymatic label such that binding of the compound, e.g., the substrate, to 38692 or 21117 can be determined by detecting the labeled compound, e.g., substrate, in a complex. Alternatively, 38692 or 21117 can be coupled with a radioisotope or enzymatic label to monitor the ability of a test compound to modulate 38692 or 21117 binding to a 38692 or 21117 substrate in a complex. For example, compounds (e.g., 38692 or 21117 substrates) can be labeled with $^{125}$I, $^{35}$S, $^{14}$C, or $^{3}$H, either directly or indirectly, and the radioisotope detected by direct counting of radioemission or by scintillation counting. Alternatively, compounds can be enzymatically labeled with, for example, horseradish peroxidase, alkaline phosphatase, or luciferase, and the enzymatic label detected by determination of conversion of an appropriate substrate to product.

The ability of a compound (e.g., a 38692 or 21117 substrate) to interact with 38692 or 21117 with or without the labeling of any of the interactants can be evaluated. For example, a microphysiometer can be used to detect the interaction of a compound with 38692 or 21117 without the labeling of either the compound or 38692 or 21117. McConnell, H. M. et al. (1992) *Science* 257:1906–1912. As used herein, a "microphysiometer" (e.g., Cytosensor) is an analytical instrument that measures the rate at which a cell acidifies its environment using a light-addressable potentiometric sensor (LAPS). Changes in this acidification rate can be used as an indicator of the interaction between a compound and 38692 or 21117.

In yet another embodiment, a cell-free assay is provided in which a 38692 or 21117 protein or biologically active portion thereof is contacted with a test compound and the ability of the test compound to bind to the 38692 or 21117 protein or biologically active portion thereof is evaluated. Preferred biologically active portions of the 38692 or 21117 proteins to be used in assays of the present invention include fragments that participate in interactions with non-38692 or 21117 molecules, e.g., fragments with high surface probability scores.

Soluble and/or membrane-bound forms of isolated proteins (e.g., 38692 or 21117 proteins or biologically active portions thereof) can be used in the cell-free assays of the invention. When membrane-bound forms of the protein are used, it may be desirable to utilize a solubilizing agent. Examples of such solubilizing agents include non-ionic detergents such as n-octylglucoside, n-dodecylglucoside, n-dodecylmaltoside, octanoyl-N-methylglucamide, decanoyl-N-methylglucamide, Triton® X-100, Triton® X-114, Thesit®, Isotridecypoly(ethylene glycol ether)$_n$, 3-[(3-cholamidopropyl)dimethylamminio]-1-propane sulfonate (CHAPS), 3-[(3-cholamidopropyl)dimethylamminio]-2-hydroxy-1-propane sulfonate (CHAPSO), or N-dodecyl=N,N-dimethyl-3-ammonio-1-propane sulfonate.

Cell-free assays involve preparing a reaction mixture of the target gene protein and the test compound under conditions and for a time sufficient to allow the two components to interact and bind, thus forming a complex that can be removed and/or detected.

Assay where ability of agent to block binding of phosphatase activity within a cell is evaluated.

The interaction between two molecules can also be detected, e.g., using fluorescence energy transfer (FET) (see, for example, Lakowicz et al., U.S. Pat. No. 5,631,169; Stavrianopoulos, et al., U.S. Pat. No. 4,868,103). A fluorophore label on the first, 'donor' molecule is selected such that its emitted fluorescent energy will be absorbed by a fluorescent label on a second, 'acceptor' molecule, which in turn is able to fluoresce due to the absorbed energy. Alternately, the 'donor' protein molecule may simply utilize the natural fluorescent energy of tryptophan residues. Labels are chosen that emit different wavelengths of light, such that the 'acceptor' molecule label may be differentiated from that of the 'donor'. Since the efficiency of energy transfer between the labels is related to the distance separating the molecules, the spatial relationship between the molecules can be assessed. In a situation in which binding occurs between the molecules, the fluorescent emission of the 'acceptor' molecule label in the assay should be maximal. An FET binding event can be conveniently measured through standard fluorometric detection means well known in the art (e.g., using a fluorimeter).

In another embodiment, determining the ability of the 38692 or 21117 protein to bind to a target molecule can be accomplished using real-time Biomolecular Interaction Analysis (BIA) (see, e.g., Sjolander, S. and Urbaniczky, C. (1991) *Anal. Chem.* 63:2338–2345 and Szabo et al. (1995) *Curr. Opin. Struct. Biol.* 5:699–705). "Surface plasmon resonance" or "BIA" detects biospecific interactions in real time, without labeling any of the interactants (e.g., BIAcore). Changes in the mass at the binding surface (indicative of a binding event) result in alterations of the refractive index of light near the surface (the optical phenomenon of surface plasmon resonance (SPR)), resulting in a detectable signal that can be used as an indication of real-time reactions between biological molecules.

In one embodiment, the target gene product or the test substance is anchored onto a solid phase. The target gene product/test compound complexes anchored on the solid phase can be detected at the end of the reaction. Preferably, the target gene product can be anchored onto a solid surface, and the test compound (which is not anchored), can be labeled, either directly or indirectly, with detectable labels discussed herein.

It may be desirable to immobilize either 38692 or 21117, an anti 38692 or 21117 antibody or its target molecule to facilitate separation of complexed from uncomplexed forms of one or both of the proteins, as well as to accommodate automation of the assay. Binding of a test compound to a 38692 or 21117 protein, or interaction of a 38692 or 21117 protein with a target molecule in the presence and absence of a candidate compound, can be accomplished in any vessel suitable for containing the reactants. Examples of such vessels include microtiter plates, test tubes, and microcentrifuge tubes. In one embodiment, a fusion protein can be provided which adds a domain that allows one or both of the proteins to be bound to a matrix. For example, glutathione-S-transferase/38692 or 21117 fusion proteins or glutathione-S-transferase/target fusion proteins can be adsorbed onto glutathione sepharose beads (Sigma Chemical, St. Louis, Mo.) or glutathione derivatized microtiter plates, which are then combined with the test compound or the test compound and either the non-adsorbed target protein or 38692 or 21117 protein, and the mixture incubated under conditions conducive to complex formation (e.g., at physiological conditions for salt and pH). Following incubation, the beads or microtiter plate wells are washed to remove any unbound components, the matrix immobilized in the case of beads, complex determined either directly or indirectly, for example, as described above. Alternatively, the complexes can be dissociated from the matrix, and the level of 38692 or 21117 binding or activity determined using standard techniques.

Other techniques for immobilizing either a 38692 or 21117 protein or a target molecule on matrices include using conjugation of biotin and streptavidin. Biotinylated 38692 or 21117 protein or target molecules can be prepared from biotin-NHS (N-hydroxy-succinimide) using techniques known in the art (e.g., biotinylation kit, Pierce Chemicals, Rockford, Ill.), and immobilized in the wells of streptavidin-coated 96 well plates (Pierce Chemical).

In order to conduct the assay, the non-immobilized component is added to the coated surface containing the anchored component. After the reaction is complete, unreacted components are removed (e.g., by washing) under conditions such that any complexes formed will remain immobilized on the solid surface. The detection of complexes anchored on the solid surface can be accomplished in a number of ways. Where the previously non-immobilized component is pre-labeled, the detection of label immobilized on the surface indicates that complexes were formed. Where the previously non-immobilized component is not pre-labeled, an indirect label can be used to detect complexes anchored on the surface; e.g., using a labeled antibody specific for the immobilized component (the antibody, in turn, can be directly labeled or indirectly labeled with, e.g., a labeled anti-Ig antibody).

In one embodiment, this assay is performed utilizing antibodies reactive with 38692 or 21117 protein or target molecules but which do not interfere with binding of the 38692 or 21117 protein to its target molecule. Such antibodies can be derivatized to the wells of the plate, and unbound target or 38692 or 21117 protein is trapped in the wells by antibody conjugation. Methods for detecting such complexes, in addition to those described above for the GST-immobilized complexes, include immunodetection of complexes using antibodies reactive with the 38692 or 21117 protein or target molecule, as well as enzyme-linked assays which rely on detecting an enzymatic activity associated with the 38692 or 21117 protein or target molecule.

Alternatively, cell free assays can be conducted in a liquid phase. In such an assay, the reaction products are separated from unreacted components by any of a number of standard techniques, including but not limited to: differential centrifugation (see, for example, Rivas, G., and Minton, A. P., (1993) *Trends Biochem Sci* August;18(8):284–7); chromatography (gel filtration chromatography, ion-exchange chromatography); electrophoresis (see, e.g., Ausubel, F. et al., eds. Current Protocols in Molecular Biology 1999, J. Wiley: New York.); and immunoprecipitation (see, for example, Ausubel, F. et al., eds. Current Protocols in Molecular Biology 1999, J. Wiley: New York). Such resins and chromatographic techniques are known to one skilled in the art (see, e.g., Heegaard, N. H., (1998) *J. Mol Recognit* Winter; 11 (1–6): 141–8; Hage, D. S., and Tweed, S. A. (1997) *J. Chromatogr B. Biomed Sci Appl* October 10;699 (1–2):499–525). Further, fluorescence energy transfer may also be conveniently utilized, as described herein, to detect binding without further purification of the complex from solution.

In a preferred embodiment, the assay includes contacting the 38692 or 21117 protein or biologically active portion thereof with a known compound which binds 38692 or 21117 to form an assay mixture, contacting the assay mixture with a test compound, and determining the ability of the test compound to interact with a 38692 or 21117 protein, wherein determining the ability of the test compound to interact with a 38692 or 21117 protein includes determining the ability of the test compound to preferentially bind to 38692 or 21117 or biologically active portion thereof, or to modulate the activity of a target molecule, as compared to the known compound.

The target gene products of the invention can, in vivo, interact with one or more cellular or extracellular macromolecules, such as proteins. For the purposes of this discussion, such cellular and extracellular macromolecules are referred to herein as "binding partners." Compounds that disrupt such interactions can be useful in regulating the activity of the target gene product. Such compounds can include, but are not limited to molecules such as antibodies, peptides, and small molecules. The preferred target genes/products for use in this embodiment are the 38692 or 21117 genes herein identified. In an alternative embodiment, the invention provides methods for determining the ability of the test compound to modulate the activity of a 38692 or 21117 protein through modulation of the activity of a downstream effector of a 38692 or 21117 target molecule. For example, the activity of the effector molecule on an appropriate target can be determined, or the binding of the effector to an appropriate target can be determined, as previously described.

To identify compounds that interfere with the interaction between the target gene product and its cellular or extracellular binding partner(s), e.g., a substrate, a reaction mixture containing the target gene product and the binding partner is prepared, under conditions and for a time sufficient, to allow the two products to form complex. In order to test an inhibitory agent, the reaction mixture is provided in the presence and absence of the test compound. The test compound can be initially included in the reaction mixture, or can be added at a time subsequent to the addition of the target gene and its cellular or extracellular binding partner. Control reaction mixtures are incubated without the test compound or with a placebo. The formation of any complexes between the target gene product and the cellular or extracellular binding partner is then detected. The formation of a complex in the control reaction, but not in the reaction mixture containing the test compound, indicates that the compound interferes with the interaction of the target gene product and the interactive binding partner. Additionally, complex formation within reaction mixtures containing the test compound and normal target gene product can also be compared to complex formation within reaction mixtures containing the test compound and mutant target gene product. This comparison can be important in those cases wherein it is desirable to identify compounds that disrupt interactions of mutant but not normal target gene products.

These assays can be conducted in a heterogeneous or homogeneous format. Heterogeneous assays involve anchoring either the target gene product or the binding partner onto a solid phase, and detecting complexes anchored on the solid phase at the end of the reaction. In homogeneous assays, the entire reaction is carried out in a liquid phase. In either approach, the order of addition of reactants can be varied to obtain different information about the compounds being tested. For example, test compounds that interfere with the interaction between the target gene products and the binding partners, e.g., by competition, can be identified by conducting the reaction in the presence of the test substance. Alternatively, test compounds that disrupt preformed complexes, e.g., compounds with higher binding constants that displace one of the components from the complex, can be tested by adding the test compound to the reaction mixture after complexes have been formed. The various formats are briefly described below.

In a heterogeneous assay system, either the target gene product or the interactive cellular or extracellular binding partners, is anchored onto a solid surface (e.g., a microtiter plate), while the non-anchored species is labeled either directly or indirectly. The anchored species can be immobilized by non-covalent or covalent attachments. Alternatively, an immobilized antibody specific for the species to be anchored can be used to anchor the species to the solid surface.

In order to conduct the assay, the partner of the immobilized species is exposed to the coated surface with or without the test compound. After the reaction is complete, unreacted components are removed (e.g., by washing) and any complexes that have formed remain immobilized on the solid surface. In assays where the non-immobilized species is pre-labeled, the detection of label immobilized on the surface indicates that complexes were formed. In assays where the non-immobilized species is not pre-labeled, an indirect label can be used to detect complexes anchored on the surface; e.g., using a labeled antibody specific for the initially non-immobilized species (the antibody, in turn, can be directly labeled or indirectly labeled with, e.g., a labeled anti-Ig antibody). Depending upon the order of addition of reaction components, test compounds that inhibit complex formation or that disrupt preformed complexes can be detected.

Alternatively, the reaction can be conducted in a liquid phase in the presence or absence of the test compound. Reaction products are separated from unreacted components and complexes detected using, for example, an immobilized antibody specific for one of the binding components to anchor any complexes formed in solution and a labeled antibody specific for the other partner to detect anchored complexes. Again, depending upon the order of addition of reactants to the liquid phase, test compounds that inhibit complex formation or that disrupt preformed complexes can be identified.

In an alternate embodiment of the invention, a homogeneous assay can be used. For example, a preformed complex of the target gene product and the interactive cellular or extracellular binding partner product is prepared in which either the target gene products or their binding partners are labeled, but the signal generated by the label is quenched due to complex formation (see, e.g., U.S. Pat. No. 4,109,496 that utilizes this approach for immunoassays). The addition of a test substance that competes with and displaces one of the species from the preformed complex will result in the generation of a signal above background. In this way, test substances that disrupt target gene product-binding partner interaction can be identified.

In yet another aspect, the 38692 or 21117 proteins can be used as "bait proteins" in a two-hybrid assay or three-hybrid assay (see, e.g., U.S. Pat. No. 5,283,317; Zervos et al. (1993) *Cell* 72:223–232; Madura et al. (1993) *J. Biol. Chem.* 268:12046–12054; Bartel et al. (1993) *Biotechniques* 14:920–924; Iwabuchi et al. (1993) *Oncogene* 8:1693–1696; and Brent WO94/10300), to identify other proteins, which bind to or interact with 38692 or 21117 ("38692 or 21117-binding proteins" or "38692 or 21117-bp") and are involved in 38692 or 21117 activity. Such 38692 or 21117-bps can be activators or inhibitors of signals by the 38692 or 21117 proteins or 38692 or 21117 targets as, for example, downstream elements of a 38692 or 21117-mediated signaling pathway.

The two-hybrid system is based on the modular nature of most transcription factors, which consist of separable DNA-binding and activation domains. Briefly, the assay utilizes two different DNA constructs. In one construct, the gene that codes for a 38692 or 21117 protein is fused to a gene encoding the DNA binding domain of a known transcription factor (e.g., GAL-4). In the other construct, a DNA sequence from a library of DNA sequences that encodes an unidentified protein ("prey" or "sample") is fused to a gene that codes for the activation domain of the known transcription factor. (Alternatively the 38692 or 21117 protein can be fused to the activator domain.) If the "bait" and the "prey" proteins are able to interact in vivo and form a 38692 or 21117-dependent complex, the DNA-binding and activation domains of the transcription factor are brought into close proximity. This proximity allows transcription of a reporter gene (e.g., LacZ) that is operably linked to a transcriptional regulatory site responsive to the transcription factor. Expression of the reporter gene can be detected and cell colonies containing the functional transcription factor can be isolated and used to obtain the cloned gene that encodes the protein that interacts with the 38692 or 21117 protein.

In another embodiment, modulators of 38692 or 21117 expression are identified. For example, a cell or cell free mixture is contacted with a candidate compound and the expression of 38692 or 21117 mRNA or protein evaluated relative to the level of expression of 38692 or 21117 mRNA or protein in the absence of the candidate compound. When expression of 38692 or 21117 mRNA or protein is greater in the presence of the candidate compound than in its absence, the candidate compound is identified as a stimulator of 38692 or 21117 mRNA or protein expression. Alternatively, when expression of 38692 or 21117 mRNA or protein is less (statistically significantly less) in the presence of the candidate compound than in its absence, the candidate compound is identified as an inhibitor of 38692 or 21117 mRNA or protein expression. The level of 38692 or 21117 mRNA or protein expression can be determined by methods described herein for detecting 38692 or 21117 mRNA or protein.

In another aspect, the invention pertains to a combination of two or more of the assays described herein. For example, a modulating agent can be identified using a cell-based or a cell free assay, and the ability of the agent to modulate the activity of a 38692 or 21117 protein can be confirmed in vivo, e.g., in an animal such as an animal model overexpressing a gene encoding a protein serine/threonine kinase.

This invention further pertains to novel agents identified by the above-described screening assays. Accordingly, it is within the scope of this invention to further use an agent identified as described herein (e.g., a 38692 or 21117 modulating agent, an antisense 38692 or 21117 nucleic acid molecule, a 38692 or 21117-specific antibody, or a 38692 or 21117-binding partner) in an appropriate animal model to determine the efficacy, toxicity, side effects, or mechanism of action, of treatment with such an agent. Furthermore, novel agents identified by the above-described screening assays can be used for treatments as described herein.

Detection Assays

Portions or fragments of the nucleic acid sequences identified herein can be used as polynucleotide reagents. For example, these sequences can be used to: (i) map their respective genes on a chromosome e.g., to locate gene regions associated with genetic disease or to associate 38692 or 21117 with a disease; (ii) identify an individual from a minute biological sample (tissue typing); and (iii) aid in forensic identification of a biological sample. These applications are described in the subsections below.

Chromosome Mapping

The 38692 or 21117 nucleotide sequences or portions thereof can be used to map the location of the 38692 or 21117 genes on a chromosome. This process is called chromosome mapping. Chromosome mapping is useful in correlating the 38692 or 21117 sequences with genes associated with disease.

Briefly, 38692 or 21117 genes can be mapped to chromosomes by preparing PCR primers (preferably 15–25 bp in length) from the 38692 or 21117 nucleotide sequences. These primers can then be used for PCR screening of somatic cell hybrids containing individual human chromosomes. Only those hybrids containing the human gene corresponding to the 38692 or 21117 sequences will yield an amplified fragment.

A panel of somatic cell hybrids in which each cell line contains either a single human chromosome or a small number of human chromosomes and a full set of mouse chromosomes, allows easy mapping of individual genes to specific human chromosomes. (D'Eustachio P. et al. (1983) *Science* 220:919–924).

Other mapping strategies e.g., in situ hybridization (described in Fan, Y. et al. (1990) *Proc. Natl. Acad. Sci. USA*, 87:6223–27), pre-screening with labeled flow-sorted chromosomes, and pre-selection by hybridization to chromosome specific cDNA libraries can be used to map 38692 or 21117 to a chromosomal location.

Fluorescence in situ hybridization (FISH) of a DNA sequence to a metaphase chromosomal spread can further be used to provide a precise chromosomal location in one step. The FISH technique can be used with a DNA sequence as short as 500 or 600 bases. However, clones larger than 1,000 bases have a higher likelihood of binding to a unique chromosomal location with sufficient signal intensity for simple detection. Preferably 1,000 bases, and more preferably 2,000 bases will suffice to get good results at a reasonable amount of time. For a review of this technique, see Verma et al., Human Chromosomes: A Manual of Basic Techniques (Pergamon Press, New York 1988).

Reagents for chromosome mapping can be used individually to mark a single chromosome or a single site on that chromosome, or panels of reagents can be used for marking multiple sites and/or multiple chromosomes. Reagents corresponding to noncoding regions of the genes actually are preferred for mapping purposes. Coding sequences are more likely to be conserved within gene families, thus increasing the chance of cross hybridizations during chromosomal mapping.

Once a sequence has been mapped to a precise chromosomal location, the physical position of the sequence on the chromosome can be correlated with genetic map data. (Such data are found, for example, in V. McKusick, Mendelian Inheritance in Man, available on-line through Johns Hopkins University Welch Medical Library). The relationship between a gene and a disease, mapped to the same chromosomal region, can then be identified through linkage analysis (co-inheritance of physically adjacent genes), described in, for example, Egeland, J. et al. (1987) *Nature,* 325:783–787.

Moreover, differences in the DNA sequences between individuals affected and unaffected with a disease associated with the 38692 or 21117 gene, can be determined. If a mutation is observed in some or all of the affected individuals but not in any unaffected individuals, then the mutation is likely to be the causative agent of the particular disease. Comparison of affected and unaffected individuals generally involves first looking for structural alterations in the chromosomes, such as deletions or translocations that are visible from chromosome spreads or detectable using PCR based on that DNA sequence. Ultimately, complete sequencing of genes from several individuals can be performed to confirm the presence of a mutation and to distinguish mutations from polymorphisms.

Tissue Typing 38692 or 21117 sequences can be used to identify individuals from biological samples using, e.g., restriction fragment length polymorphism (RFLP). In this technique, an individual's genomic DNA is digested with one or more restriction enzymes, the fragments separated, e.g., by electrophoresis and Southern blotted, and probed to yield bands for identification. The sequences of the present invention are useful as additional DNA markers for RFLP (described in U.S. Pat. No. 5,272,057).

Furthermore, the sequences of the present invention can also be used to determine the actual base-by-base DNA sequence of selected portions of an individual's genome. Thus, the 38692 or 21117 nucleotide sequences described herein can be used to prepare two PCR primers from the 5' and 3' ends of the sequences. These primers can then be used to amplify an individual's DNA and subsequently sequence it. Panels of corresponding DNA sequences from individuals, prepared in this manner, can provide unique individual identifications, as each individual will have a unique set of such DNA sequences due to allelic differences.

Allelic variation occurs to some degree in the coding regions of these sequences, and to a greater degree in the noncoding regions. Each of the sequences described herein can, to some degree, be used as a standard against which DNA from an individual can be compared for identification purposes. Because greater numbers of polymorphisms occur in the noncoding regions, fewer sequences are necessary to differentiate individuals. The noncoding sequences of SEQ ID NO:1 can provide positive individual identification with a panel of perhaps 10 to 1,000 primers, which each yield a noncoding amplified sequence of 100 bases. If predicted coding sequences, such as those in SEQ ID NO:3 are used, a more appropriate number of primers for positive individual identification would be 500–2,000.

If a panel of reagents from 38692 or 21117 nucleotide sequences described herein is used to generate a unique identification database for an individual, those same reagents can later be used to identify tissue from that individual. Using the unique identification database, positive identification of the individual, living or dead, can be made from extremely small tissue samples.

Use of Partial 38692 or 21117 Sequences in Forensic Biology

DNA-based identification techniques can also be used in forensic biology. To make such an identification, PCR technology can be used to amplify DNA sequences taken from very small biological samples such as tissues, e.g., hair or skin, or body fluids, e.g., blood, saliva, or semen, found at a crime scene. The amplified sequence can then be compared to a standard, thereby allowing identification of the origin of the biological sample.

The sequences of the present invention can be used to provide polynucleotide reagents, e.g., PCR primers, targeted to specific loci in the human genome, which can enhance the reliability of DNA-based forensic identifications by, for example, providing another "identification marker" (i.e., another DNA sequence that is unique to a particular individual). As mentioned above, actual base sequence information can be used for identification as an accurate alternative to patterns formed by restriction enzyme generated fragments. Sequences targeted to noncoding regions of SEQ ID NO:1 (e.g., fragments derived from the noncoding regions of SEQ ID NO:1 and having a length of at least 20 bases, preferably at least 30 bases) are particularly appropriate for this use.

The 38692 or 21117 nucleotide sequences described herein can further be used to provide polynucleotide reagents, e.g., labeled or labelable probes which can be used in, for example, an in situ hybridization technique, to identify a specific tissue, e.g., a tissue containing 38692 or 21117 serine/threonine phosphatase activity. This can be very useful in cases where a forensic pathologist is presented with a tissue of unknown origin. Panels of such 38692 or 21117 probes can be used to identify tissue by species and/or by organ type.

In a similar fashion, these reagents, e.g., 38692 or 21117 primers or probes can be used to screen tissue culture for contamination (i.e., screen for the presence of a mixture of different types of cells in a culture).

Predictive Medicine

The present invention also pertains to the field of predictive medicine in which diagnostic assays, prognostic assays, and monitoring clinical trials are used for prognostic (predictive) purposes to thereby treat an individual.

Generally, the invention provides, a method of determining if a subject is at risk for a disorder related to a lesion in or the misexpression of a gene that encodes 38692 or 21117. Such disorders include, e.g., a disorder associated with the misexpression of 38692 or 21117.

The method includes one or more of the following:

detecting, in a tissue of the subject, the presence or absence of a mutation which affects the expression of the 38692 or 21117 gene, or detecting the presence or absence of a mutation in a region which controls the expression of the gene, e.g., a mutation in the 5' control region;

detecting, in a tissue of the subject, the presence or absence of a mutation which alters the structure of the 38692 or 21117 gene;

detecting, in a tissue of the subject, the misexpression of the 38692 or 21117 gene at the mRNA level, e.g., detecting a non-wild type level of a mRNA;

detecting, in a tissue of the subject, the misexpression of the gene at the protein level, e.g., detecting a non-wild type level of a 38692 or 21117 polypeptide.

In preferred embodiments the method includes: ascertaining the existence of at least one of: a deletion of one or more nucleotides from the 38692 or 21117 gene; an insertion of one or more nucleotides into the gene, a point mutation, e.g., a substitution of one or more nucleotides of the gene, or a gross chromosomal rearrangement of the gene, e.g., a translocation, inversion, or deletion.

For example, detecting the genetic lesion can include: (i) providing a probe/primer including an oligonucleotide containing a region of nucleotide sequence that hybridizes to a sense or antisense sequence from SEQ ID NO:1, 3, 4, or 6, or naturally occurring mutants thereof or 5' or 3' flanking sequences naturally associated with the 38692 or 21117 gene; (ii) exposing the probe/primer to nucleic acid of the tissue; and (iii) detecting, by hybridization, e.g., in situ hybridization, of the probe/primer to the nucleic acid, the presence or absence of the genetic lesion.

In preferred embodiments detecting the misexpression includes ascertaining the existence of at least one of: an alteration in the level of a messenger RNA transcript of the 38692 or 21117 gene; the presence of a non-wild type splicing pattern of a messenger RNA transcript of the gene; or a non-wild type level of 38692 or 21117.

Methods of the invention can be used prenatally or to determine if a subject's offspring will be at risk for a disorder.

In preferred embodiments the method includes determining the structure of a 38692 or 21117 gene, an abnormal structure being indicative of risk for the disorder.

In preferred embodiments the method includes contacting a sample form the subject with an antibody to the 38692 or 21117 protein or a nucleic acid, which hybridizes specifically with the gene. This and other embodiments are discussed below.

Diagnostic and Prognostic Assays

Diagnostic and prognostic assays of the invention include method for assessing the expression level of 38692 or 21117 molecules and for identifying variations and mutations in the sequence of 38692 or 21117 molecules.

Expression Monitoring and Profiling

The presence, level, or absence of 38692 or 21117 protein or nucleic acid in a biological sample can be evaluated by obtaining a biological sample from a test subject and contacting the biological sample with a compound or an agent capable of detecting 38692 or 21117 protein or nucleic acid (e.g., mRNA, genomic DNA) that encodes 38692 or 21117 protein such that the presence of 38692 or 21117 protein or nucleic acid is detected in the biological sample. The term "biological sample" includes tissues, cells and biological fluids isolated from a subject, as well as tissues, cells and fluids present within a subject. A preferred biological sample is serum. The level of expression of the 38692 or 21117 gene can be measured in a number of ways, including, but not limited to: measuring the mRNA encoded by the 38692 or 21117 genes; measuring the amount of protein encoded by the 38692 or 21117 genes; or measuring the activity of the protein encoded by the 38692 or 21117 genes.

The level of mRNA corresponding to the 38692 or 21117 gene in a cell can be determined both by in situ and by in vitro formats.

The isolated mRNA can be used in hybridization or amplification assays that include, but are not limited to, Southern or Northern analyses, polymerase chain reaction analyses and probe arrays. One preferred diagnostic method for the detection of mRNA levels involves contacting the isolated mRNA with a nucleic acid molecule (probe) that can hybridize to the mRNA encoded by the gene being detected. The nucleic acid probe can be, for example, a full-length 38692 or 21117 nucleic acid, such as the nucleic acid of SEQ ID NO:1 or 3, or a portion thereof, such as an oligonucleotide of at least 7, 15, 30, 50, 100, 250 or 500 nucleotides in length and sufficient to specifically hybridize under stringent conditions to 38692 or 21117 mRNA or genomic DNA. The probe can be disposed on an address of an array, e.g., an array described below. Other suitable probes for use in the diagnostic assays are described herein.

In one format, mRNA (or cDNA) is immobilized on a surface and contacted with the probes, for example by running the isolated mRNA on an agarose gel and transferring the mRNA from the gel to a membrane, such as nitrocellulose. In an alternative format, the probes are immobilized on a surface and the mRNA (or cDNA) is contacted with the probes, for example, in a two-dimensional gene chip array described below. A skilled artisan can adapt known mRNA detection methods for use in detecting the level of mRNA encoded by the 38692 or 21117 genes.

The level of mRNA in a sample that is encoded by one of 38692 or 21117 can be evaluated with nucleic acid amplification, e.g., by rtPCR (Mullis (1987) U.S. Pat. No. 4,683,202), ligase chain reaction (Barany (1991) *Proc. Natl. Acad. Sci. USA* 88:189–193), self sustained sequence replication (Guatelli et al., (1990) *Proc. Natl. Acad. Sci. USA* 87:1874–1878), transcriptional amplification system (Kwoh et al., (1989), *Proc. Natl. Acad. Sci. USA* 86:1173–1177), Q-Beta Replicase (Lizardi et al., (1988) *Bio/Technology* 6:1197), rolling circle replication (Lizardi et al., U.S. Pat. No. 5,854,033) or any other nucleic acid amplification method, followed by the detection of the amplified molecules using techniques known in the art. As used herein, amplification primers are defined as being a pair of nucleic acid molecules that can anneal to 5' or 3' regions of a gene (plus and minus strands, respectively, or vice-versa) and contain a short region in between. In general, amplification primers are from about 10 to 30 nucleotides in length and flank a region from about 50 to 200 nucleotides in length. Under appropriate conditions and with appropriate reagents, such primers permit the amplification of a nucleic acid molecule comprising the nucleotide sequence flanked by the primers.

For in situ methods, a cell or tissue sample can be prepared/processed and immobilized on a support, typically a glass slide, and then contacted with a probe that can hybridize to mRNA that encodes the 38692 or 21117 gene being analyzed.

In another embodiment, the methods further contacting a control sample with a compound or agent capable of detecting 38692 or 21117 mRNA, or genomic DNA, and comparing the presence of 38692 or 21117 mRNA or genomic DNA in the control sample with the presence of 38692 or 21117 mRNA or genomic DNA in the test sample. In still another embodiment, serial analysis of gene expression, as described in U.S. Pat. No. 5,695,937, is used to detect 38692 or 21117 transcript levels.

A variety of methods can be used to determine the level of protein encoded by 38692 or 21117. In general, these methods include contacting an agent that selectively binds to the protein, such as an antibody with a sample, to evaluate the level of protein in the sample. In a preferred embodiment, the antibody bears a detectable label. Antibodies can be polyclonal, or more preferably, monoclonal. An intact antibody, or a fragment thereof (e.g., Fab or F(ab')$_2$) can be used. The term "labeled", with regard to the probe or antibody, is intended to encompass direct labeling of the probe or antibody by coupling (i.e., physically linking) a detectable substance to the probe or antibody, as well as indirect labeling of the probe or antibody by reactivity with a detectable substance. Examples of detectable substances are provided herein.

The detection methods can be used to detect 38692 or 21117 protein in a biological sample in vitro as well as in vivo. In vitro techniques for detection of 38692 or 21117 protein include enzyme linked immunosorbent assays (ELISAs), immunoprecipitations, immunofluorescence, enzyme immunoassay (EIA), radioimmunoassay (RIA), and Western blot analysis. In vivo techniques for detection of 38692 or 21117 protein include introducing into a subject a labeled anti-38692 or 21117 antibody. For example, the antibody can be labeled with a radioactive marker whose presence and location in a subject can be detected by standard imaging techniques. In another embodiment, the sample is labeled, e.g., biotinylated and then contacted to the antibody, e.g., an anti-38692 or 21117 antibody positioned on an antibody array (as described below). The sample can be detected, e.g., with avidin coupled to a fluorescent label.

In another embodiment, the methods further include contacting the control sample with a compound or agent capable of detecting 38692 or 21117 protein, and comparing the presence of 38692 or 21117 protein in the control sample with the presence of 38692 or 21117 protein in the test sample.

The invention also includes kits for detecting the presence of 38692 or 21117 in a biological sample. For example, the kit can include a compound or agent capable of detecting 38692 or 21117 protein or mRNA in a biological sample; and a standard. The compound or agent can be packaged in a suitable container. The kit can further comprise instructions for using the kit to detect 38692 or 21117 protein or nucleic acid.

For antibody-based kits, the kit can include: (1) a first antibody (e.g., attached to a solid support) which binds to a polypeptide corresponding to a marker of the invention; and, optionally, (2) a second, different antibody which binds to either the polypeptide or the first antibody and is conjugated to a detectable agent.

For oligonucleotide-based kits, the kit can include: (1) an oligonucleotide, e.g., a detectably labeled oligonucleotide, which hybridizes to a nucleic acid sequence encoding a polypeptide corresponding to a marker of the invention or (2) a pair of primers useful for amplifying a nucleic acid molecule corresponding to a marker of the invention. The kit can also includes a buffering agent, a preservative, or a protein stabilizing agent. The kit can also includes components necessary for detecting the detectable agent (e.g., an enzyme or a substrate). The kit can also contain a control sample or a series of control samples which can be assayed and compared to the test sample contained. Each component of the kit can be enclosed within an individual container and all of the various containers can be within a single package, along with instructions for interpreting the results of the assays performed using the kit.

The diagnostic methods described herein can identify subjects having, or at risk of developing, a disease or disorder associated with misexpressed or aberrant or unwanted 38692 or 21117 expression or activity. As used herein, the term "unwanted" includes an unwanted phenomenon involved in a biological response such as pain or deregulated cell proliferation.

In one embodiment, a disease or disorder associated with aberrant or unwanted 38692 or 21117 expression or activity is identified. A test sample is obtained from a subject and 38692 or 21117 protein or nucleic acid (e.g., mRNA or genomic DNA) is evaluated, wherein the level, e.g., the presence or absence, of 38692 or 21117 protein or nucleic acid is diagnostic for a subject having or at risk of developing a disease or disorder associated with aberrant or unwanted 38692 or 21117 expression or activity. As used herein, a "test sample" refers to a biological sample obtained from a subject of interest, including a biological fluid (e.g., serum), cell sample, or tissue.

The prognostic assays described herein can be used to determine whether a subject can be administered an agent (e.g., an agonist, antagonist, peptidomimetic, protein, peptide, nucleic acid, small molecule, or other drug candidate) to treat a disease or disorder associated with aberrant or unwanted 38692 or 21117 expression or activity. For example, such methods can be used to determine whether a subject can be effectively treated with an agent for a hematopoietic disorder (e.g., an erythroid, myeloid, monocyte, or megakaryocyte cell-associated disorder).

In another aspect, the invention features a computer medium having a plurality of digitally encoded data records. Each data record includes a value representing the level of expression of 38692 or 21117 in a sample, and a descriptor of the sample. The descriptor of the sample can be an identifier of the sample, a subject from which the sample was derived (e.g., a patient), a diagnosis, or a treatment (e.g., a preferred treatment). In a preferred embodiment, the data record further includes values representing the level of expression of genes other than 38692 or 21117 (e.g., other genes associated with a 38692 or 21117-disorder, or other genes on an array). The data record can be structured as a table, e.g., a table that is part of a database such as a relational database (e.g., a SQL database of the Oracle or Sybase database environments).

Also featured is a method of evaluating a sample. The method includes providing a sample, e.g., from the subject, and determining a gene expression profile of the sample, wherein the profile includes a value representing the level of 38692 or 21117 expression. The method can further include comparing the value or the profile (i.e., multiple values) to a reference value or reference profile. The gene expression profile of the sample can be obtained by any of the methods described herein (e.g., by providing a nucleic acid from the sample and contacting the nucleic acid to an array). The method can be used to diagnose a hematopoietic disorder (e.g., an erythroid, myeloid, monocyte, or megakaryocyte cell-associated disorder), in a subject wherein altered 38692 or 21117 expression is an indication that the subject has or is disposed to having a hematopoietic disorder (e.g., an erythroid, myeloid, monocyte, or megakaryocyte cell-associated disorder as described herein). The method can be used to monitor a treatment for a hematopoietic disorder (e.g., an erythroid, myeloid, monocyte, or megakaryocyte cell-associated disorder as described herein). For example, the gene expression profile can be determined for a sample from a subject undergoing treatment. The profile can be compared to a reference profile or to a profile obtained from the subject prior to treatment or prior to onset of the disorder (see, e.g., Golub et al. (1999) *Science* 286:531).

In yet another aspect, the invention features a method of evaluating a test compound (see also, "Screening Assays", above). The method includes providing a cell and a test compound; contacting the test compound to the cell; obtaining a subject expression profile for the contacted cell; and comparing the subject expression profile to one or more reference profiles. The profiles include a value representing the level of 38692 or 21117 expression. In a preferred embodiment, the subject expression profile is compared to a target profile, e.g., a profile for a normal cell or for desired condition of a cell. The test compound is evaluated favorably if the subject expression profile is more similar to the target profile than an expression profile obtained from an uncontacted cell.

In another aspect, the invention features, a method of evaluating a subject. The method includes: a) obtaining a sample from a subject, e.g., from a caregiver, e.g., a caregiver who obtains the sample from the subject; b) determining a subject expression profile for the sample. Optionally, the method further includes either or both of steps: c) comparing the subject expression profile to one or more reference expression profiles; and d) selecting the reference profile most similar to the subject reference profile. The subject expression profile and the reference profiles include a value representing the level of 38692 or 21117 expression. A variety of routine statistical measures can be used to compare two reference profiles. One possible metric is the length of the distance vector that is the difference between the two profiles. Each of the subject and reference profile is represented as a multi-dimensional vector, wherein each dimension is a value in the profile.

The method can further include transmitting a result to a caregiver. The result can be the subject expression profile, a result of a comparison of the subject expression profile with another profile, a most similar reference profile, or a descriptor of any of the aforementioned. The result can be transmitted across a computer network, e.g., the result can be in the form of a computer transmission, e.g., a computer data signal embedded in a carrier wave.

Also featured is a computer medium having executable code for effecting the following steps: receive a subject expression profile; access a database of reference expression profiles; and either i) select a matching reference profile most similar to the subject expression profile or ii) determine at least one comparison score for the similarity of the subject expression profile to at least one reference profile. The subject expression profile, and the reference expression profiles each include a value representing the level of 38692 or 21117 expression.

Arrays and Uses Thereof

In another aspect, the invention features an array that includes a substrate having a plurality of addresses. At least one address of the plurality includes a capture probe that binds specifically to a 38692 or 21117 molecule (e.g., a 38692 or 21117 nucleic acid or a 38692 or 21117 polypeptide). The array can have a density of at least than 10, 50, 100, 200, 500, 1,000, 2,000, or 10,000 or more addresses/cm$^2$, and ranges between. In a preferred embodiment, the plurality of addresses includes at least 10, 100, 500, 1,000, 5,000, 10,000, 50,000 addresses. In a preferred embodiment, the plurality of addresses includes equal to or less than 10, 100, 500, 1,000, 5,000, 10,000, or 50,000 addresses. The substrate can be a two-dimensional substrate such as a glass slide, a wafer (e.g., silica or plastic), a mass spectroscopy plate, or a three-dimensional substrate such as a gel pad. Addresses in addition to address of the plurality can be disposed on the array.

In a preferred embodiment, at least one address of the plurality includes a nucleic acid capture probe that hybridizes specifically to a 38692 or 21117 nucleic acid, e.g., the sense or anti-sense strand. In one preferred embodiment, a subset of addresses of the plurality of addresses has a nucleic acid capture probe for 38692 or 21117. Each address of the subset can include a capture probe that hybridizes to a different region of a 38692 or 21117 nucleic acid. In another preferred embodiment, addresses of the subset include a capture probe for a 38692 or 21117 nucleic acid. Each address of the subset is unique, overlapping, and complementary to a different variant of 38692 or 21117 (e.g., an allelic variant, or all possible hypothetical variants). The array can be used to sequence 38692 or 21117 by hybridization (see, e.g., U.S. Pat. No. 5,695,940).

An array can be generated by various methods, e.g., by photolithographic methods (see, e.g., U.S. Pat. Nos. 5,143, 854; 5,510,270; and 5,527,681), mechanical methods (e.g., directed-flow methods as described in U.S. Pat. No. 5,384, 261), pin-based methods (e.g., as described in U.S. Pat. No. 5,288,514), and bead-based techniques (e.g., as described in PCT US/93/04145).

In another preferred embodiment, at least one address of the plurality includes a polypeptide capture probe that binds specifically to a 38692 or 21117 polypeptide or fragment thereof. The polypeptide can be a naturally-occurring interaction partner of 38692 or 21117 polypeptide. Preferably, the polypeptide is an antibody, e.g., an antibody described herein (see "Anti-38692 or 21117 Antibodies," above), such as a monoclonal antibody or a single-chain antibody.

In another aspect, the invention features a method of analyzing the expression of 38692 or 21117. The method includes providing an array as described above; contacting the array with a sample and detecting binding of a 38692 or 21117-molecule (e.g., nucleic acid or polypeptide) to the array. In a preferred embodiment, the array is a nucleic acid array. Optionally the method further includes amplifying nucleic acid from the sample prior or during contact with the array.

In another embodiment, the array can be used to assay gene expression in a tissue to ascertain tissue specificity of genes in the array, particularly the expression of 38692 or 21117. If a sufficient number of diverse samples is analyzed, clustering (e.g., hierarchical clustering, k-means clustering, Bayesian clustering and the like) can be used to identify other genes which are co-regulated with 38692 or 21117. For example, the array can be used for the quantitation of the expression of multiple genes. Thus, not only tissue specificity, but also the level of expression of a battery of genes in the tissue is ascertained. Quantitative data can be used to group (e.g., cluster) genes on the basis of their tissue expression per se and level of expression in that tissue.

For example, array analysis of gene expression can be used to assess the effect of cell—cell interactions on 38692 or 21117 expression. A first tissue can be perturbed and nucleic acid from a second tissue that interacts with the first tissue can be analyzed. In this context, the effect of one cell type on another cell type in response to a biological stimulus can be determined, e.g., to monitor the effect of cell—cell interaction at the level of gene expression.

In another embodiment, cells are contacted with a therapeutic agent. The expression profile of the cells is determined using the array, and the expression profile is compared to the profile of like cells not contacted with the agent. For example, the assay can be used to determine or analyze the molecular basis of an undesirable effect of the therapeutic agent. If an agent is administered therapeutically to treat one cell type but has an undesirable effect on another cell type, the invention provides an assay to determine the molecular basis of the undesirable effect and thus provides the opportunity to co-administer a counteracting agent or otherwise treat the undesired effect. Similarly, even within a single cell type, undesirable biological effects can be determined at the molecular level. Thus, the effects of an agent on expression of other than the target gene can be ascertained and counteracted.

In another embodiment, the array can be used to monitor expression of one or more genes in the array with respect to time. For example, samples obtained from different time points can be probed with the array. Such analysis can identify and/or characterize the development of a 38692 or 21117-associated disease or disorder; and processes, such as a cellular transformation associated with a 38692 or 21117-associated disease or disorder. The method can also evaluate the treatment and/or progression of a 38692 or 21117-associated disease or disorder The array is also useful for ascertaining differential expression patterns of one or more genes in normal and abnormal cells. This provides a battery of genes (e.g., including 38692 or 21117) that could serve as a molecular target for diagnosis or therapeutic intervention.

In another aspect, the invention features an array having a plurality of addresses. Each address of the plurality includes a unique polypeptide. At least one address of the plurality has disposed thereon a 38692 or 21117 polypeptide or fragment thereof. Methods of producing polypeptide arrays are described in the art, e.g., in De Wildt et al. (2000). *Nature Biotech.* 18, 989–994; Lueking et al. (1999). *Anal Biochem.* 270, 103–111; Ge, H. (2000). *Nucleic Acids Res.* 28, e3, I–VII; MacBeath, G., and Schreiber, S. L. (2000). *Science* 289, 1760–1763; and WO 99/51773A1. In a preferred embodiment, each addresses of the plurality has disposed thereon a polypeptide at least 60, 70, 80, 85, 90, 95 or 99% identical to a 38692 or 21117 polypeptide or fragment thereof. For example, multiple variants of a 38692 or 21117 polypeptide (e.g., encoded by allelic variants, site-directed mutants, random mutants, or combinatorial mutants) can be disposed at individual addresses of the plurality. Addresses in addition to the address of the plurality can be disposed on the array.

The polypeptide array can be used to detect a 38692 or 21117 binding compound, e.g., an antibody in a sample from a subject with specificity for a 38692 or 21117 polypeptide or the presence of a 38692 or 21117-binding protein or ligand.

The array is also useful for ascertaining the effect of the expression of a gene on the expression of other genes in the same cell or in different cells (e.g., ascertaining the effect of 38692 or 21117 expression on the expression of other genes). This provides, for example, for a selection of alternate molecular targets for therapeutic intervention if the ultimate or downstream target cannot be regulated.

In another aspect, the invention features a method of analyzing a plurality of probes. The method is useful, e.g., for analyzing gene expression. The method includes: providing a two dimensional array having a plurality of addresses, each address of the plurality being positionally distinguishable from each other address of the plurality having a unique capture probe, e.g., wherein the capture probes are from a cell or subject which express 38692 or 21117 or from a cell or subject in which a 38692 or 21117 mediated response has been elicited, e.g., by contact of the cell with 38692 or 21117 nucleic acid or protein, or administration to the cell or subject 38692 or 21117 nucleic acid or protein; providing a two dimensional array having a plurality of addresses, each address of the plurality being positionally distinguishable from each other address of the plurality, and each address of the plurality having a unique capture probe, e.g., wherein the capture probes are from a cell or subject which does not express 38692 or 21117 (or does not express as highly as in the case of the 38692 or 21117 positive plurality of capture probes) or from a cell or subject which in which a 38692 or 21117 mediated response has not been elicited (or has been elicited to a lesser extent than in the first sample); contacting the array with one or more inquiry probes (which is preferably other than a 38692 or 21117 nucleic acid, polypeptide, or antibody), and thereby evaluating the plurality of capture probes. Binding, e.g., in the case of a nucleic acid, hybridization with a capture probe at an address of the plurality, is detected, e.g., by signal generated from a label attached to the nucleic acid, polypeptide, or antibody.

In another aspect, the invention features a method of analyzing a plurality of probes or a sample. The method is useful, e.g., for analyzing gene expression. The method includes: providing a two dimensional array having a plurality of addresses, each address of the plurality being positionally distinguishable from each other address of the plurality having a unique capture probe, contacting the array with a first sample from a cell or subject which express or mis-express 38692 or 21117 or from a cell or subject in which a 38692 or 21117-mediated response has been elicited, e.g., by contact of the cell with 38692 or 21117 nucleic acid or protein, or administration to the cell or subject 38692 or 21117 nucleic acid or protein; providing a two dimensional array having a plurality of addresses, each address of the plurality being positionally distinguishable from each other address of the plurality, and each address of the plurality having a unique capture probe, and contacting the array with a second sample from a cell or subject which does not express 38692 or 21117 (or does not express as highly as in the case of the 38692 or 21117 positive plurality of capture probes) or from a cell or subject which in which a 38692 or 21117 mediated response has not been elicited (or has been elicited to a lesser extent than in the first sample); and comparing the binding of the first sample with the binding of the second sample. Binding, e.g., in the case of a nucleic acid, hybridization with a capture probe at an address of the plurality, is detected, e.g., by signal generated from a label attached to the nucleic acid, polypeptide, or antibody. The same array can be used for both samples or different arrays can be used. If different arrays are used the plurality of addresses with capture probes should be present on both arrays.

In another aspect, the invention features a method of analyzing 38692 or 21117, e.g., analyzing structure, function, or relatedness to other nucleic acid or amino acid sequences. The method includes: providing a 38692 or 21117 nucleic acid or amino acid sequence; comparing the 38692 or 21117 sequence with one or more preferably a plurality of sequences from a collection of sequences, e.g., a nucleic acid or protein sequence database; to thereby analyze 38692 or 21117.

Detection of Variations or Mutations

The methods of the invention can also be used to detect genetic alterations in a 38692 or 21117 gene, thereby determining if a subject with the altered gene is at risk for a disorder characterized by misregulation in 38692 or 21117 protein activity or nucleic acid expression, such as a hematopoietic disorder (e.g., an erythroid, myeloid, monocyte, or megakaryocyte cell-associated disorder as described herein). In preferred embodiments, the methods include detecting, in a sample from the subject, the presence or absence of a genetic alteration characterized by at least one of an alteration affecting the integrity of a gene encoding a 38692 or 21117-protein, or the mis-expression of the 38692 or 21117 gene. For example, such genetic alterations can be detected by ascertaining the existence of at least one of 1) a deletion of one or more nucleotides from a 38692 or 21117 gene; 2) an addition of one or more nucleotides to a 38692 or 21117 gene; 3) a substitution of one or more nucleotides of a 38692 or 21117 gene, 4) a chromosomal rearrangement of a 38692 or 21117 gene; 5) an alteration in the level of a messenger RNA transcript of a 38692 or 21117 gene, 6) aberrant modification of a 38692 or 21117 gene, such as of the methylation pattern of the genomic DNA, 7) the presence of a non-wild type splicing pattern of a messenger RNA transcript of a 38692 or 21117 gene, 8) a non-wild type level of a 38692 or 21117-protein, 9) allelic loss of a 38692 or 21117 gene, and 10) inappropriate post-translational modification of a 38692 or 21117-protein.

An alteration can be detected without a probe/primer in a polymerase chain reaction, such as anchor PCR or RACE PCR, or, alternatively, in a ligation chain reaction (LCR), the latter of which can be particularly useful for detecting point mutations in the 38692 or 21117-gene. This method can include the steps of collecting a sample of cells from a subject, isolating nucleic acid (e.g., genomic, mRNA or both) from the sample, contacting the nucleic acid sample with one or more primers which specifically hybridize to a 38692 or 21117 gene under conditions such that hybridization and amplification of the 38692 or 21117-gene (if present) occurs, and detecting the presence or absence of an amplification product, or detecting the size of the amplification product and comparing the length to a control sample. It is anticipated that PCR and/or LCR may be desirable to use as a preliminary amplification step in conjunction with any of the techniques used for detecting mutations described herein. Alternatively, other amplification methods described herein or known in the art can be used.

In another embodiment, mutations in a 38692 or 21117 gene from a sample cell can be identified by detecting alterations in restriction enzyme cleavage patterns. For example, sample and control DNA is isolated, amplified (optionally), digested with one or more restriction endonucleases, and fragment length sizes are determined, e.g., by gel electrophoresis and compared. Differences in fragment length sizes between sample and control DNA indicates mutations in the sample DNA. Moreover, the use of sequence specific ribozymes (see, for example, U.S. Pat. No. 5,498,531) can be used to score for the presence of specific mutations by development or loss of a ribozyme cleavage site.

In other embodiments, genetic mutations in 38692 or 21117 can be identified by hybridizing a sample and control nucleic acids, e.g., DNA or RNA, two-dimensional arrays, e.g., chip based arrays. Such arrays include a plurality of addresses, each of which is positionally distinguishable from the other. A different probe is located at each address of the plurality. A probe can be complementary to a region of a 38692 or 21117 nucleic acid or a putative variant (e.g., allelic variant) thereof. A probe can have one or more mismatches to a region of a 38692 or 21117 nucleic acid (e.g., a destabilizing mismatch). The arrays can have a high density of addresses, e.g., can contain hundreds or thousands of oligonucleotides probes (Cronin, M. T. et al. (1996) *Human Mutation* 7: 244–255; Kozal, M. J. et al. (1996) *Nature Medicine* 2: 753–759). For example, genetic mutations in 38692 or 21117 can be identified in two-dimensional arrays containing light-generated DNA probes as described in Cronin, M. T. et al. supra. Briefly, a first hybridization array of probes can be used to scan through long stretches of DNA in a sample and control to identify base changes between the sequences by making linear arrays of sequential overlapping probes. This step allows the identification of point mutations. This step is followed by a second hybridization array that allows the characterization of specific mutations by using smaller, specialized probe arrays complementary to all variants or mutations detected. Each mutation array is composed of parallel probe sets, one complementary to the wild-type gene and the other complementary to the mutant gene.

In yet another embodiment, any of a variety of sequencing reactions known in the art can be used to directly sequence the 38692 or 21117 gene and detect mutations by comparing the sequence of the sample 38692 or 21117 with the corresponding wild-type (control) sequence. Automated sequencing procedures can be utilized when performing the diagnostic assays ((1995) *Biotechniques* 19:448), including sequencing by mass spectrometry.

Other methods for detecting mutations in the 38692 or 21117 gene include methods in which protection from cleavage agents is used to detect mismatched bases in RNA/RNA or RNA/DNA heteroduplexes (Myers et al. (1985) *Science* 230:1242; Cotton et al. (1988) *Proc. Natl Acad Sci USA* 85:4397; Saleeba et al. (1992) *Methods Enzymol.* 217:286–295).

In still another embodiment, the mismatch cleavage reaction employs one or more proteins that recognize mismatched base pairs in double-stranded DNA (so called "DNA mismatch repair" enzymes) in defined systems for detecting and mapping point mutations in 38692 or 21117 cDNAs obtained from samples of cells. For example, the mutY enzyme of *E. coli* cleaves A at G/A mismatches and the thymidine DNA glycosylase from HeLa cells cleaves T at G/T mismatches (Hsu et al. (1994) *Carcinogenesis* 15:1657–1662; U.S. Pat. No. 5,459,039).

In other embodiments, alterations in electrophoretic mobility will be used to identify mutations in 38692 or 21117 genes. For example, single strand conformation polymorphism (SSCP) may be used to detect differences in electrophoretic mobility between mutant and wild type nucleic acids (Orita et al. (1989) *Proc. Natl. Acad. Sci USA*: 86:2766, see also Cotton (1993) *Mutat. Res.* 285:125–144; and Hayashi (1992) *Genet. Anal. Tech. Appl.* 9:73–79). Single-stranded DNA fragments of sample and control 38692 or 21117 nucleic acids will be denatured and allowed to renature. The secondary structure of single-stranded nucleic acids varies according to sequence, the resulting alteration in electrophoretic mobility enables the detection of even a single base change. The DNA fragments may be labeled or detected with labeled probes. The sensitivity of the assay may be enhanced by using RNA (rather than DNA), in which the secondary structure is more sensitive to a change in sequence. In a preferred embodiment, the subject method utilizes heteroduplex analysis to separate double stranded heteroduplex molecules on the basis of changes in electrophoretic mobility (Keen et al. (1991) *Trends Genet* 7:5).

In yet another embodiment, the movement of mutant or wild-type fragments in polyacrylamide gels containing a gradient of denaturant is assayed using denaturing gradient gel electrophoresis (DGGE) (Myers et al. (1985) *Nature*

313:495). When DGGE is used as the method of analysis, DNA will be modified to insure that it does not completely denature, for example by adding a GC clamp of approximately 40 bp of high-melting GC-rich DNA by PCR. In a further embodiment, a temperature gradient is used in place of a denaturing gradient to identify differences in the mobility of control and sample DNA (Rosenbaum and Reissner (1987) *Biophys Chem* 265:12753).

Examples of other techniques for detecting point mutations include, but are not limited to, selective oligonucleotide hybridization, selective amplification, or selective primer extension (Saiki et al. (1986) *Nature* 324:163); Saiki et al. (1989) *Proc. Natl Acad. Sci USA* 86:6230). A further method of detecting point mutations is the chemical ligation of oligonucleotides as described in Xu et al. ((2001) *Nature Biotechnol.* 19:148). Adjacent oligonucleotides, one of which selectively anneals to the query site, are ligated together if the nucleotide at the query site of the sample nucleic acid is complementary to the query oligonucleotide; ligation can be monitored, e.g., by fluorescent dyes coupled to the oligonucleotides.

Alternatively, allele specific amplification technology that depends on selective PCR amplification may be used in conjunction with the instant invention. Oligonucleotides used as primers for specific amplification may carry the mutation of interest in the center of the molecule (so that amplification depends on differential hybridization) (Gibbs et al. (1989) *Nucleic Acids Res.* 17:2437–2448) or at the extreme 3' end of one primer where, under appropriate conditions, mismatch can prevent, or reduce polymerase extension (Prossner (1993) *Tibtech* 11:238). In addition it may be desirable to introduce a novel restriction site in the region of the mutation to create cleavage-based detection (Gasparini et al. (1992) *Mol. Cell Probes* 6:1). It is anticipated that in certain embodiments amplification may also be performed using Taq ligase for amplification (Barany (1991) *Proc. Natl. Acad. Sci USA* 88:189). In such cases, ligation will occur only if there is a perfect match at the 3' end of the 5' sequence making it possible to detect the presence of a known mutation at a specific site by looking for the presence or absence of amplification.

In another aspect, the invention features a set of oligonucleotides. The set includes a plurality of oligonucleotides, each of which is at least partially complementary (e.g., at least 50%, 60%, 70%, 80%, 90%, 92%, 95%, 97%, 98%, or 99% complementary) to a 38692 or 21117 nucleic acid.

In a preferred embodiment the set includes a first and a second oligonucleotide. The first and second oligonucleotide can hybridize to the same or to different locations of SEQ ID NO:1 or 3, or the complement of SEQ ID NO:1, 3, 4, or 6. Different locations can be different but overlapping or or nonoverlapping on the same strand. The first and second oligonucleotide can hybridize to sites on the same or on different strands.

The set can be useful, e.g., for identifying SNP's, or identifying specific alleles of 38692 or 21117. In a preferred embodiment, each oligonucleotide of the set has a different nucleotide at an interrogation position. In one embodiment, the set includes two oligonucleotides, each complementary to a different allele at a locus, e.g., a biallelic or polymorphic locus.

In another embodiment, the set includes four oligonucleotides, each having a different nucleotide (e.g., adenine, guanine, cytosine, or thymidine) at the interrogation position. The interrogation position can be a SNP or the site of a mutation. In another preferred embodiment, the oligonucleotides of the plurality are identical in sequence to one another (except for differences in length). The oligonucleotides can be provided with differential labels, such that an oligonucleotide that hybridizes to one allele provides a signal that is distinguishable from an oligonucleotide that hybridizes to a second allele. In still another embodiment, at least one of the oligonucleotides of the set has a nucleotide change at a position in addition to a query position, e.g., a destabilizing mutation to decrease the $T_m$ of the oligonucleotide. In another embodiment, at least one oligonucleotide of the set has a non-natural nucleotide, e.g., inosine. In a preferred embodiment, the oligonucleotides are attached to a solid support, e.g., to different addresses of an array or to different beads or nanoparticles.

In a preferred embodiment the set of oligo nucleotides can be used to specifically amplify, e.g., by PCR, or detect, a 38692 or 21117 nucleic acid.

The methods described herein may be performed, for example, by utilizing pre-packaged diagnostic kits comprising at least one probe nucleic acid or antibody reagent described herein, which may be conveniently used, e.g., in clinical settings to diagnose patients exhibiting symptoms or family history of a disease or illness involving a 38692 or 21117 gene.

Use of 38692 or 21117 Molecules as Surrogate Markers

The 38692 or 21117 molecules of the invention are also useful as markers of disorders or disease states, as markers for precursors of disease states, as markers for predisposition of disease states, as markers of drug activity, or as markers of the pharmacogenomic profile of a subject. Using the methods described herein, the presence, absence and/or quantity of the 38692 or 21117 molecules of the invention may be detected, and may be correlated with one or more biological states in vivo. For example, the 38692 or 21117 molecules of the invention may serve as surrogate markers for one or more disorders or disease states or for conditions leading up to disease states. As used herein, a "surrogate marker" is an objective biochemical marker which correlates with the absence or presence of a disease or disorder, or with the progression of a disease or disorder (e.g., with the presence or absence of a tumor). The presence or quantity of such markers is independent of the disease. Therefore, these markers may serve to indicate whether a particular course of treatment is effective in lessening a disease state or disorder. Surrogate markers are of particular use when the presence or extent of a disease state or disorder is difficult to assess through standard methodologies (e.g., early stage tumors), or when an assessment of disease progression is desired before a potentially dangerous clinical endpoint is reached (e.g., an assessment of cardiovascular disease may be made using cholesterol levels as a surrogate marker, and an analysis of HIV infection may be made using HIV RNA levels as a surrogate marker, well in advance of the undesirable clinical outcomes of myocardial infarction or fully-developed AIDS). Examples of the use of surrogate markers in the art include: Koomen et al. (2000) *J. Mass. Spectrom.* 35: 258–264; and James (1994) *AIDS Treatment News Archive* 209.

The 38692 or 21117 molecules of the invention are also useful as pharmacodynamic markers. As used herein, a "pharmacodynamic marker" is an objective biochemical marker which correlates specifically with drug effects. The presence or quantity of a pharmacodynamic marker is not related to the disease state or disorder for which the drug is being administered; therefore, the presence or quantity of the marker is indicative of the presence or activity of the drug in a subject. For example, a pharmacodynamic marker may be indicative of the concentration of the drug in a biological tissue, in that the marker is either expressed or transcribed or not expressed or transcribed in that tissue in relationship to the level of the drug. In this fashion, the distribution or uptake of the drug may be monitored by the pharmacodynamic marker. Similarly, the presence or quantity of the pharmacodynamic marker may be related to the presence or quantity of the metabolic product of a drug, such that the presence or quantity of the marker is indicative of the relative breakdown rate of the drug in vivo. Pharmacodynamic markers are of particular use in increasing the sensitivity of detection of drug effects, particularly when the drug is administered in low doses. Since even a small amount of a drug may be sufficient to activate multiple rounds of marker (e.g., a 38692 or 21117 marker) transcription or expression, the amplified marker may be in a quantity which is more readily detectable than the drug itself. Also, the marker may be more easily detected due to the nature of the marker itself; for example, using the methods described herein, anti-38692 or 21117 antibodies may be employed in an immune-based detection system for a 38692 or 21117 protein marker, or 38692 or 21117-specific radiolabeled probes may be used to detect a 38692 or 21117 mRNA marker. Furthermore, the use of a pharmacodynamic marker may offer mechanism-based prediction of risk due to drug treatment beyond the range of possible direct observations. Examples of the use of pharmacodynamic markers in the art include: Matsuda et al. U.S. Pat. No. 6,033,862; Hattis et al. (1991) *Env. Health Perspect.* 90: 229–238; Schentag (1999) *Am. J. Health-Syst. Pharm.* 56 Suppl. 3: S21–S24; and Nicolau (1999) *Am, J. Health-Syst. Pharm.* 56 Suppl. 3: S16–S20.

The 38692 or 21117 molecules of the invention are also useful as pharmacogenomic markers. As used herein, a "pharmacogenomic marker" is an objective biochemical marker which correlates with a specific clinical drug response or susceptibility in a subject (see, e.g., McLeod et al. (1999) *Eur. J. Cancer* 35:1650–1652). The presence or quantity of the pharmacogenomic marker is related to the predicted response of the subject to a specific drug or class of drugs prior to administration of the drug. By assessing the presence or quantity of one or more pharmacogenomic markers in a subject, a drug therapy which is most appropriate for the subject, or which is predicted to have a greater degree of success, may be selected. For example, based on the presence or quantity of RNA, or protein (e.g., 38692 or 21117 protein or RNA) for specific tumor markers in a subject, a drug or course of treatment may be selected that is optimized for the treatment of the specific tumor likely to be present in the subject. Similarly, the presence or absence of a specific sequence mutation in 38692 or 21117 DNA may correlate 38692 or 21117 drug response. The use of pharmacogenomic markers therefore permits the application of the most appropriate treatment for each subject without having to administer the therapy.

Pharmaceutical Compositions

The nucleic acid and polypeptides, fragments thereof, as well as anti-38692 or 21117 antibodies (also referred to herein as "active compounds") of the invention can be incorporated into pharmaceutical compositions. Such compositions typically include the nucleic acid molecule, protein, or antibody and a pharmaceutically acceptable carrier. As used herein the language "pharmaceutically acceptable carrier" includes solvents, dispersion media, coatings, antibacterial and antifungal agents, isotonic and absorption delaying agents, and the like, compatible with pharmaceutical administration. Supplementary active compounds can also be incorporated into the compositions.

A pharmaceutical composition is formulated to be compatible with its intended route of administration. Examples of routes of administration include parenteral, e.g., intravenous, intradermal, subcutaneous, oral (e.g., inhalation), transdermal (topical), transmucosal, and rectal administration. Solutions or suspensions used for parenteral, intradermal, or subcutaneous application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. pH can be adjusted with acids or bases, such as hydrochloric acid or sodium hydroxide. The parenteral preparation can be enclosed in ampoules, disposable syringes or multiple dose vials made of glass or plastic.

Pharmaceutical compositions suitable for injectable use include sterile aqueous solutions (where water soluble) or dispersions and sterile powders for the extemporaneous preparation of sterile injectable solutions or dispersion. For intravenous administration, suitable carriers include physiological saline, bacteriostatic water, Cremophor EL™ (BASF, Parsippany, N.J.) or phosphate buffered saline (PBS). In all cases, the composition must be sterile and should be fluid to the extent that easy syringability exists. It should be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyetheylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as manitol, sorbitol, sodium chloride in the composition. Prolonged absorption of the injectable compositions can be brought about by including in the composition an agent which delays absorption, for example, aluminum monostearate and gelatin.

Sterile injectable solutions can be prepared by incorporating the active compound in the required amount in an appropriate solvent with one or a combination of ingredients enumerated above, as required, followed by filtered sterilization. Generally, dispersions are prepared by incorporating the active compound into a sterile vehicle that contains a basic dispersion medium and the required other ingredients from those enumerated above. In the case of sterile powders for the preparation of sterile injectable solutions, the preferred methods of preparation are vacuum drying and freeze-drying, which yield a powder of the active ingredient plus any additional desired ingredient from a previously sterile-filtered solution thereof.

Oral compositions generally include an inert diluent or an edible carrier. For the purpose of oral therapeutic administration, the active compound can be incorporated with excipients and used in the form of tablets, troches, or capsules, e.g., gelatin capsules. Oral compositions can also be prepared using a fluid carrier for use as a mouthwash.

Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring.

For administration by inhalation, the compounds are delivered in the form of an aerosol spray from pressured container or dispenser that contains a suitable propellant, e.g., a gas such as carbon dioxide, or a nebulizer.

Systemic administration can also be by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the active compounds are formulated into ointments, salves, gels, or creams as generally known in the art.

The compounds can also be prepared in the form of suppositories (e.g., with conventional suppository bases such as cocoa butter and other glycerides) or retention enemas for rectal delivery.

In one embodiment, the active compounds are prepared with carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially from Alza Corporation and Nova Pharmaceuticals, Inc. Liposomal suspensions (including liposomes targeted to infected cells with monoclonal antibodies to viral antigens) can also be used as pharmaceutically acceptable carriers. These can be prepared according to methods known to those skilled in the art, for example, as described in U.S. Pat. No. 4,522,811.

It is advantageous to formulate oral or parenteral compositions in dosage unit form for ease of administration and uniformity of dosage. Dosage unit form as used herein refers to physically discrete units suited as unitary dosages for the subject to be treated; each unit containing a predetermined quantity of active compound calculated to produce the desired therapeutic effect in association with the required pharmaceutical carrier.

Toxicity and therapeutic efficacy of such compounds can be determined by standard pharmaceutical procedures in cell cultures or experimental animals, e.g., for determining the $LD_{50}$ (the dose lethal to 50% of the population) and the $ED_{50}$ (the dose therapeutically effective in 50% of the population). The dose ratio between toxic and therapeutic effects is the therapeutic index and it can be expressed as the ratio $LD_{50}/ED_{50}$. Compounds that exhibit high therapeutic indices are preferred. While compounds that exhibit toxic side effects may be used, care should be taken to design a delivery system that targets such compounds to the site of affected tissue in order to minimize potential damage to uninfected cells and, thereby, reduce side effects.

The data obtained from the cell culture assays and animal studies can be used in formulating a range of dosage for use in humans. The dosage of such compounds lies preferably within a range of circulating concentrations that include the $ED_{50}$ with little or no toxicity. The dosage may vary within this range depending upon the dosage form employed and the route of administration utilized. For any compound used in the method of the invention, the therapeutically effective dose can be estimated initially from cell culture assays. A dose may be formulated in animal models to achieve a circulating plasma concentration range that includes the $IC_{50}$ (i.e., the concentration of the test compound which achieves a half-maximal inhibition of symptoms) as determined in cell culture. Such information can be used to more accurately determine useful doses in humans. Levels in plasma may be measured, for example, by high performance liquid chromatography.

As defined herein, a therapeutically effective amount of protein or polypeptide (i.e., an effective dosage) ranges from about 0.001 to 30 mg/kg body weight, preferably about 0.01 to 25 mg/kg body weight, more preferably about 0.1 to 20 mg/kg body weight, and even more preferably about 1 to 10 mg/kg, 2 to 9 mg/kg, 3 to 8 mg/kg, 4 to 7 mg/kg, or 5 to 6 mg/kg body weight. The protein or polypeptide can be administered one time per week for between about 1 to 10 weeks, preferably between 2 to 8 weeks, more preferably between about 3 to 7 weeks, and even more preferably for about 4, 5, or 6 weeks. The skilled artisan will appreciate that certain factors may influence the dosage and timing required to effectively treat a subject, including but not limited to the severity of the disease or disorder, previous treatments, the general health and/or age of the subject, and other diseases present. Moreover, treatment of a subject with a therapeutically effective amount of a protein, polypeptide, or antibody can include a single treatment or, preferably, can include a series of treatments.

For antibodies, the preferred dosage is 0.1 mg/kg of body weight (generally 10 mg/kg to 20 mg/kg). If the antibody is to act in the brain, a dosage of 50 mg/kg to 100 mg/kg is usually appropriate. Generally, partially human antibodies and fully human antibodies have a longer half-life within the human body than other antibodies. Accordingly, lower dosages and less frequent administration is often possible. Modifications such as lipidation can be used to stabilize antibodies and to enhance uptake and tissue penetration (e.g., into the brain). A method for lipidation of antibodies is described by Cruikshank et al. ((1997) *J. Acquired Immune Deficiency Syndromes and Human Retrovirology* 14:193).

The present invention encompasses agents that modulate expression or activity. An agent may, for example, be a small molecule. For example, such small molecules include, but are not limited to, peptides, peptidomimetics (e.g., peptoids), amino acids, amino acid analogs, polynucleotides, polynucleotide analogs, nucleotides, nucleotide analogs, organic or inorganic compounds (i.e., including heteroorganic and organometallic compounds) having a molecular weight less than about 10,000 grams per mole, organic or inorganic compounds having a molecular weight less than about 5,000 grams per mole, organic or inorganic compounds having a molecular weight less than about 1,000 grams per mole, organic or inorganic compounds having a molecular weight less than about 500 grams per mole, and salts, esters, and other pharmaceutically acceptable forms of such compounds.

Exemplary doses include milligram or microgram amounts of the small molecule per kilogram of subject or sample weight (e.g., about 1 μg/kg to about 500 mg/kg, about 100 µg/kg to about 5 mg/kg, or about 1 µg/kg to about 50 µg/kg. It is furthermore understood that appropriate doses of a small molecule depend upon the potency of the small molecule with respect to the expression or activity to be modulated. When one or more of these small molecules is to be administered to an animal (e.g., a human) in order to modulate expression or activity of a polypeptide or nucleic acid of the invention, a physician, veterinarian, or researcher may, for example, prescribe a relatively low dose at first, subsequently increasing the dose until an appropriate response is obtained. In addition, it is understood that the specific dose level for any particular animal subject will depend upon a variety of factors including the activity of the specific compound employed, the age, body weight, general health, gender, and diet of the subject, the time of administration, the route of administration, the rate of excretion, any drug combination, and the degree of expression or activity to be modulated.

An antibody (or fragment thereof) may be conjugated to a therapeutic moiety such as a cytotoxin, a therapeutic agent or a radioactive metal ion. A cytotoxin or cytotoxic agent includes any agent that is detrimental to cells. Examples include taxol, cytochalasin B, gramicidin D, ethidium bromide, emetine, mitomycin, etoposide, tenoposide, vincristine, vinblastine, colchicin, doxorubicin, daunorubicin, dihydroxy anthracin dione, mitoxantrone, mithramycin, actinomycin D, 1-dehydrotestosterone, glucocorticoids, procaine, tetracaine, lidocaine, propranolol, and puromycin and analogs or homologs thereof. Therapeutic agents include, but are not limited to, antimetabolites (e.g., methotrexate, 6-mercaptopurine, 6-thioguanine, cytarabine, 5-fluorouracil decarbazine), alkylating agents (e.g., mechlorethamine, thioepa chlorambucil, melphalan, carmustine (BSNU) and lomustine (CCNU), cyclothosphamide, busulfan, dibromomannitol, streptozotocin, mitomycin C, and cis-dichlorodiamine platinum (II) (DDP) cisplatin), anthracyclines (e.g., daunorubicin (formerly daunomycin) and doxorubicin), antibiotics (e.g., dactinomycin (formerly actinomycin), bleomycin, mithramycin, and anthramycin (AMC)), and anti-mitotic agents (e.g., vincristine and vinblastine).

The conjugates of the invention can be used for modifying a given biological response. The drug moiety is not to be construed as limited to classical chemical therapeutic agents. For example, the drug moiety may be a protein or polypeptide possessing a desired biological activity. Such proteins may include, for example, a toxin such as abrin, ricin A, pseudomonas exotoxin, or diphtheria toxin; a protein such as tumor necrosis factor, α-interferon, β-interferon, nerve growth factor, platelet derived growth factor, tissue plasminogen activator; or, biological response modifiers such as, for example, lymphokines, interleukin-1 ("IL-1"), interleukin-2 ("IL-2"), interleukin-6 ("IL-6"), granulocyte macrophase colony stimulating factor ("GM-CSF"), granulocyte colony stimulating factor ("G-CSF"), or other growth factors.

Alternatively, an antibody can be conjugated to a second antibody to form an antibody heteroconjugate as described by Segal in U.S. Pat. No. 4,676,980.

The nucleic acid molecules of the invention can be inserted into vectors and used as gene therapy vectors. Gene therapy vectors can be delivered to a subject by, for example, intravenous injection, local administration (see U.S. Pat. No. 5,328,470) or by stereotactic injection (see e.g., Chen et al. (1994) *Proc. Natl. Acad. Sci. USA* 91:3054–3057). The pharmaceutical preparation of the gene therapy vector can include the gene therapy vector in an acceptable diluent, or can comprise a slow release matrix in which the gene delivery vehicle is imbedded. Alternatively, where the complete gene delivery vector can be produced intact from recombinant cells, e.g., retroviral vectors, the pharmaceutical preparation can include one or more cells which produce the gene delivery system.

The pharmaceutical compositions can be included in a container, pack, or dispenser together with instructions for administration.

Methods of Treatment

The present invention provides for both prophylactic and therapeutic methods of treating a subject at risk of (or susceptible to) a disorder or having a disorder associated with aberrant or unwanted 38692 or 21117 expression or activity. As used herein, the term "treatment" is defined as the application or administration of a therapeutic agent to a patient, or application or administration of a therapeutic agent to an isolated tissue or cell line from a patient, who has a disease, a symptom of disease or a predisposition toward a disease, with the purpose to cure, heal, alleviate, relieve, alter, remedy, ameliorate, improve or affect the disease, the symptoms of disease or the predisposition toward disease. A therapeutic agent includes, but is not limited to, small molecules, peptides, antibodies, ribozymes and antisense oligonucleotides.

It is possible that some 21117 or 38692 disorders can be caused, at least in part, by an abnormal level of gene product, or by the presence of a gene product exhibiting abnormal activity. As such, the reduction in the level and/or activity of such gene products would bring about the amelioration of disorder symptoms. Relevant disorders can include hematopoietic disorders, e.g., erythroid-associated disorders, e.g., anemias, neoplasias of the erythroid lineage or of CD34+ cells, e.g., leukemias, and erythrocytosis, i.e. excessive erythroid differentiation.

As the 21117 molecules are also expressed in breast, colon, lung, adipose tissue, endothelial cells, and osteoblasts, these molecules can be used diagnostically and therapeutically to treat/diagnose breast, colon, lung, adipose tissue, endothelial cells, and bone.

Disorders of the breast include, but are not limited to, disorders of development; inflammations, including but not limited to, acute mastitis, periductal mastitis, periductal mastitis (recurrent subareolar abscess, squamous metaplasia of lactiferous ducts), mammary duct ectasia, fat necrosis, granulomatous mastitis, and pathologies associated with silicone breast implants; fibrocystic changes; proliferative breast disease including, but not limited to, epithelial hyperplasia, sclerosing adenosis, and small duct papillomas; tumors including, but not limited to, stromal tumors such as fibroadenoma, phyllodes tumor, and sarcomas, and epithelial tumors such as large duct papilloma; carcinoma of the breast including in situ (noninvasive) carcinoma that includes ductal carcinoma in situ (including Paget's disease) and lobular carcinoma in situ, and invasive (infiltrating) carcinoma including, but not limited to, invasive ductal carcinoma, no special type, invasive lobular carcinoma, medullary carcinoma, colloid (mucinous) carcinoma, tubular carcinoma, and invasive papillary carcinoma, and miscellaneous malignant neoplasms.

Disorders in the male breast include, but are not limited to, gynecomastia and carcinoma.

Disorders involving the colon include, but are not limited to, congenital anomalies, such as atresia and stenosis, Meckel diverticulum, congenital aganglionic megacolon-Hirschsprung disease; enterocolitis, such as diarrhea and dysentery, infectious enterocolitis, including viral gastroenteritis, bacterial enterocolitis, necrotizing enterocolitis, antibiotic-associated colitis (pseudomembranous colitis), and collagenous and lymphocytic colitis, miscellaneous intestinal inflammatory disorders, including parasites and protozoa, acquired immunodeficiency syndrome, transplantation, drug-induced intestinal injury, radiation enterocolitis, neutropenic colitis (typhlitis), and diversion colitis; idiopathic inflammatory bowel disease, such as Crohn disease and ulcerative colitis; tumors of the colon, such as non-neoplastic polyps, adenomas, familial syndromes, colorectal carcinogenesis, colorectal carcinoma, and carcinoid tumors.

Examples of disorders of the lung include, but are not limited to, congenital anomalies; atelectasis; diseases of vascular origin, such as pulmonary congestion and edema, including hemodynamic pulmonary edema and edema caused by microvascular injury, adult respiratory distress syndrome (diffuse alveolar damage), pulmonary embolism, hemorrhage, and infarction, and pulmonary hypertension and vascular sclerosis; chronic obstructive pulmonary disease, such as emphysema, chronic bronchitis, bronchial asthma, and bronchiectasis; diffuse interstitial (infiltrative, restrictive) diseases, such as pneumoconioses, sarcoidosis, idiopathic pulmonary fibrosis, desquamative interstitial pneumonitis, hypersensitivity pneumonitis, pulmonary eosinophilia (pulmonary infiltration with eosinophilia), Bronchiolitis obliterans-organizing pneumonia, diffuse pulmonary hemorrhage syndromes, including Goodpasture syndrome, idiopathic pulmonary hemosiderosis and other hemorrhagic syndromes, pulmonary involvement in collagen vascular disorders, and pulmonary alveolar proteinosis; complications of therapies, such as drug-induced lung disease, radiation-induced lung disease, and lung transplantation; tumors, such as bronchogenic carcinoma, including paraneoplastic syndromes, bronchioloalveolar carcinoma, neuroendocrine tumors, such as bronchial carcinoid, miscellaneous tumors, and metastatic tumors; pathologies of the pleura, including inflammatory pleural effusions, noninflammatory pleural effusions, pneumothorax, and pleural tumors, including solitary fibrous tumors (pleural fibroma) and malignant mesothelioma.

Disorders involving adipose tissue include aberrant or inappropriate weight gain, metabolic rate, or fat deposition, e.g, anorexia, bulimia, obesity, diabetes, or hyperlipidemia, as well as lipid or fat metabolism disorders.

As 21117 mRNA is also expressed in undifferentiated osteoblasts, 21117 may mediate disorders associated with bone metabolism. "Bone metabolism" refers to direct or indirect effects in the formation or degeneration of bone structures, e.g., bone formation, bone resorption, etc., which may ultimately affect the concentrations in serum of calcium and phosphate. This term also includes activities mediated by 21117 molecules effects in bone cells, e.g., osteoclasts and osteoblasts, that may in turn result in bone formation and degeneration. For example, 21117 molecules may support different activities of bone resorbing osteoclasts, such as the stimulation of differentiation of monocytes and mononuclear phagocytes into osteoclasts. Accordingly, 21117 molecules that modulate the production of bone cells can influence bone formation and degeneration, and thus may be used to treat bone disorders. Examples of such disorders include, but are not limited to, osteoporosis, osteodystrophy, osteomalacia, rickets, osteitis fibrosa cystica, renal osteodystrophy, osteosclerosis, anti-convulsant treatment, osteopenia, fibrogenesis-imperfecta ossium, secondary hyperparathyrodism, hypoparathyroidism, hyperparathyroidism, cirrhosis, obstructive jaundice, drug induced metabolism, medullary carcinoma, chronic renal disease, rickets, sarcoidosis, glucocorticoid antagonism, malabsorption syndrome, steatorrhea, tropical sprue, idiopathic hypercalcemia and milk fever.

Endothelial cell disorderds include, but are not limited to, includes disorders characterized by aberrant, unregulated, or unwanted endothelial cell activity, e.g., proliferation, migration, angiogenesis, or vascularization; or aberrant expression of cell surface adhesion molecules or genes associated with angiogenesis, e.g., TIE-2, FLT and FLK. Endothelial cell disorders include tumorigenesis, tumor metastasis, psoriasis, diabetic retinopathy, endometriosis, Grave's disease, ischemic disease (e.g., atherosclerosis), and chronic inflammatory diseases (e.g., rheumatoid arthritis).

With regards to both prophylactic and therapeutic methods of treatment, such treatments may be specifically tailored or modified, based on knowledge obtained from the field of pharmacogenomics as described below.

In one aspect, the invention provides a method for preventing in a subject, a disease or condition associated with an aberrant or unwanted 38692 or 21117 expression or activity, by administering to the subject 38692 or 21117 or an agent that modulates 38692 or 21117 expression or at least one 38692 or 21117 activity. Subjects at risk for a disease that is caused or contributed to by aberrant or unwanted 38692 or 21117 expression or activity can be identified by, for example, any or a combination of diagnostic or prognostic assays as described herein. Administration of a prophylactic agent can occur prior to the manifestation of symptoms characteristic of the 38692 or 21117 aberrance, such that a disease or disorder is prevented or, alternatively, delayed in its progression. Depending on the type of 38692 or 21117 aberrance, for example, a 38692 or 21117 agonist or 38692 or 21117 antagonist agent can be used for treating the subject. The appropriate agent can be determined based on screening assays described herein.

It is possible that some 38692 or 21117 disorders can be caused, at least in part, by an abnormal level of gene product, or by the presence of a gene product exhibiting abnormal activity. As such, the reduction in the level and/or activity of such gene products would bring about the amelioration of disorder symptoms.

As discussed above, successful treatment of 38692 or 21117 disorders can be brought about by techniques that serve to inhibit the expression or activity of target gene products. For example, compounds, e.g., an agent identified using assays described above, that exhibits negative modulatory activities, can be used in accordance with the invention to prevent and/or ameliorate symptoms of 38692 or 21117 disorders. Such molecules can include, but are not limited to peptides, phosphopeptides, small organic or inorganic molecules, or antibodies (including, for example, polyclonal, monoclonal, humanized, anti-idiotypic, chimeric or single chain antibodies, and Fab, F(ab')$_2$ and FAb expression library fragments, scFV molecules, and epitope-binding fragments thereof).

Further, antisense and ribozyme molecules that inhibit expression of the target gene can also be used in accordance with the invention to reduce the level of target gene expression, thus effectively reducing the level of target gene activity. Still further, triple helix molecules can be utilized in reducing the level of target gene activity. Antisense, ribozyme and triple helix molecules are discussed above.

It is possible that the use of antisense, ribozyme, and/or triple helix molecules to reduce or inhibit mutant gene expression can also reduce or inhibit the transcription (triple helix) and/or translation (antisense, ribozyme) of mRNA produced by normal target gene alleles, such that the concentration of normal target gene product present can be lower than is necessary for a normal phenotype. In such cases, nucleic acid molecules that encode and express target gene polypeptides exhibiting normal target gene activity can be introduced into cells via gene therapy method. Alternatively, in instances in which the target gene encodes an extracellular protein, it can be preferable to co-administer normal target gene protein into the cell or tissue in order to maintain the requisite level of cellular or tissue target gene activity.

Another method by which nucleic acid molecules may be utilized in treating or preventing a disease characterized by 38692 or 21117 expression is through the use of aptamer molecules specific for 38692 or 21117 protein. Aptamers are nucleic acid molecules having a tertiary structure that permits them to specifically bind to protein ligands (see, e.g., Osborne, et al. 1997 Curr. Opin. Chem Biol. 1(1): 5–9; and Patel, D. J. 1997 Curr Opin Chem Biol June;1(1):32–46). Since nucleic acid molecules may in many cases, be more conveniently introduced into target cells than therapeutic protein molecules, aptamers offer a method by which 38692 or 21117 protein activity may be specifically decreased without the introduction of drugs or other molecules which may have pluripotent effects.

Antibodies can be generated that are both specific for target gene products and that reduce target gene product activity. Such antibodies may, therefore, by administered in instances whereby negative modulatory techniques are appropriate for the treatment of 38692 or 21117 disorders. For a description of antibodies, see the Antibody section above.

In circumstances wherein injection of an animal or a human subject with a 38692 or 21117 protein or epitope for stimulating antibody production is harmful to the subject, it is possible to generate an immune response against 38692 or 21117 through the use of anti-idiotypic antibodies (see, for example, Herlyn, D. 1999 Ann Med 31(1):66–78; and Bhattacharya-Chatterjee, M., and Foon, K. A. 1998 Cancer Treat Res 94:51–68). If an anti-idiotypic antibody is introduced into a mammal or human subject, it should stimulate the production of anti-anti-idiotypic antibodies, which should be specific to the 38692 or 21117 protein. Vaccines directed to a disease characterized by 38692 or 21117 expression may also be generated in this fashion.

In instances where the target antigen is intracellular and whole antibodies are used, internalizing antibodies may be preferred. Lipofectin or liposomes can be used to deliver the antibody or a fragment of the Fab region that binds to the target antigen into cells. Where fragments of the antibody are used, the smallest inhibitory fragment that binds to the target antigen is preferred. For example, peptides having an amino acid sequence corresponding to the Fv region of the antibody can be used. Alternatively, single chain neutralizing antibodies that bind to intracellular target antigens can also be administered. Such single chain antibodies can be administered, for example, by expressing nucleotide sequences encoding single-chain antibodies within the target cell population (see e.g., Marasco et al (1993) Proc. Natl. Acad. Sci. USA 90:7889–7893).

The identified compounds that inhibit target gene expression, synthesis and/or activity can be administered to a patient at therapeutically effective doses to prevent, treat or ameliorate 38692 or 21117 disorders. A therapeutically effective dose refers to that amount of the compound sufficient to result in amelioration of symptoms of the disorders. Toxicity and therapeutic efficacy of such compounds can be determined by standard pharmaceutical procedures in cell cultures or experimental animals, e.g., for determining the $LD_{50}$ and the $ED_{50}$ as described above in the Pharmaceutical Composition section.

Another example of determination of effective dose for an individual is the ability to directly assay levels of "free" and "bound" compound in the serum of the test subject. Such assays may utilize antibody mimics and/or "biosensors" that have been created through molecular imprinting techniques. A compound that is able to modulate 38692 or 21117 activity is used as a template or "imprinting molecule," to spatially organize polymerizable monomers prior to their polymerization with catalytic reagents. The subsequent removal of the imprinted molecule leaves a polymer matrix that contains a repeated "negative image" of the compound and is able to selectively rebind the molecule under biological assay conditions. A detailed review of this technique can be seen in Ansell, R. J. et al (1996) Current Opinion in Biotechnology 7:89–94 and in Shea, K. J. (1994) Trends in Polymer Science 2:166–173. Such "imprinted" affinity matrixes are amenable to ligand-binding assays, whereby the immobilized monoclonal antibody component is replaced by an appropriately imprinted matrix. An example of the use of such matrixes in this way can be seen in Vlatakis, G. et al (1993) Nature 361:645–647. Through the use of isotope-labeling, the "free" concentration of compound which modulates the expression or activity of 38692 or 21117 can be readily monitored and used in calculations of $IC_{50}$.

Such "imprinted" affinity matrixes can also be designed to include fluorescent groups whose photon-emitting properties measurably change upon local and selective binding of target compound. These changes can be readily assayed in real time using appropriate fiberoptic devices, in turn allowing the dose in a test subject to be quickly optimized based on its individual $IC_{50}$. A rudimentary example of such a "biosensor" is discussed in Kriz, D. et al (1995) Analytical Chemistry 67:2142–2144.

Another aspect of the invention pertains to methods of modulating 38692 or 21117 expression or activity for therapeutic purposes. Accordingly, in an exemplary embodiment, the modulatory method of the invention involves contacting a cell with 38692 or 21117 or agent that modulates one or more of the activities of 38692 or 21117 protein activity associated with the cell. An agent that modulates 38692 or 21117 protein activity can be an agent as described herein, such as a nucleic acid or a protein, a naturally-occurring target molecule of a 38692 or 21117 protein (e.g., a 38692 or 21117 substrate or receptor), a 38692 or 21117 antibody, a 38692 or 21117 agonist or antagonist, a peptidomimetic of a 38692 or 21117 agonist or antagonist, or other small molecule.

In one embodiment, the agent stimulates one or more 38692 or 21117 activities. Examples of such stimulatory agents include active 38692 or 21117 protein and a nucleic acid molecule encoding 38692 or 21117. In another embodiment, the agent inhibits one or more 38692 or 21117 activities. Examples of such inhibitory agents include anti-sense 38692 or 21117 nucleic acid molecules, anti-38692 or 21117 antibodies, and 38692 or 21117 inhibitors. These modulatory methods can be performed in vitro (e.g., by culturing the cell with the agent) or, alternatively, in vivo (e.g., by administering the agent to a subject). As such, the present invention provides methods of treating an individual afflicted with a disease or disorder characterized by aberrant or unwanted expression or activity of a 38692 or 21117 protein or nucleic acid molecule. In one embodiment, the method involves administering an agent (e.g., an agent identified by a screening assay described herein), or combination of agents that modulates (e.g., up-regulates or down-regulates) 38692 or 21117 expression or activity. In another embodiment, the method involves administering a 38692 or 21117 protein or nucleic acid molecule as therapy to compensate for reduced, aberrant, or unwanted 38692 or 21117 expression or activity.

Stimulation of 38692 or 21117 activity is desirable in situations in which 38692 or 21117 is abnormally down-regulated and/or in which increased 38692 or 21117 activity is likely to have a beneficial effect. For example, stimulation of 38692 or 21117 activity is desirable in situations in which a 38692 or 21117 is down-regulated and/or in which increased 38692 or 21117 activity is likely to have a beneficial effect. Likewise, inhibition of 38692 or 21117 activity is desirable in situations in which 38692 or 21117 is abnormally up-regulated and/or in which decreased 38692 or 21117 activity is likely to have a beneficial effect.

Pharmacogenomics

The 38692 or 21117 molecules of the present invention, as well as agents, or modulators which have a stimulatory or inhibitory effect on 38692 or 21117 activity (e.g., 38692 or 21117 gene expression) as identified by a screening assay described herein can be administered to individuals to treat (prophylactically or therapeutically) 38692 or 21117-associated disorders associated with aberrant or unwanted 38692 or 21117 activity (e.g., hyperproliferative disorders, e.g., cancer). In conjunction with such treatment, pharmacogenomics may be considered. "Pharmacogenomics," as used herein, refers to the application of genomics technologies such as gene sequencing, statistical genetics, and gene expression analysis to drugs in clinical development and on the market. More specifically, the term refers the study of how a patient's genes determine his or her response to a drug (e.g., a patient's "drug response phenotype," or "drug response genotype.") Thus, another aspect of the invention provides methods for tailoring an individual's prophylactic or therapeutic treatment with either the 38692 or 21117 molecules of the present invention or 38692 or 21117 modulators according to that individual's drug response genotype.

Pharmacogenomics deals with clinically significant hereditary variations in the response to drugs due to altered drug disposition and abnormal action in affected persons. See, for example, Eichelbaum, M. et al. (1996) *Clin. Exp. Pharmacol. Physiol.* 23(10–11): 983–985 and Linder, M. W. et al. (1997) *Clin. Chem.* 43(2):254–266. In general, two types of pharmacogenetic conditions can be differentiated. Genetic conditions transmitted as a single factor altering the way drugs act on the body (altered drug action) or genetic conditions transmitted as single factors altering the way the body acts on drugs (altered drug metabolism). These pharmacogenetic conditions can occur either as rare genetic defects or as naturally occurring polymorphisms.

Differences in metabolism of therapeutics can lead to severe toxicity or therapeutic failure by altering the relation between dose and blood concentration of the pharmacologically active drug. Thus, a physician or clinician may consider applying knowledge obtained in relevant pharmacogenomics studies in determining whether to administer a 44576 molecule or 44576 modulator as well as tailoring the dosage and/or therapeutic regimen of treatment with a 44576 molecule or 44576 modulator.

One pharmacogenomics approach to identifying genes that predict drug response, known as "a genome-wide association," relies primarily on a high-resolution map of the human genome consisting of already known gene-related markers (e.g., a "bi-allelic" gene marker map which consists of 60,000–100,000 polymorphic or variable sites on the human genome, each of which has two variants.) Such a high-resolution genetic map can be compared to a map of the genome of each of a statistically significant number of patients taking part in a Phase II/III drug trial to identify markers associated with a particular observed drug response or side effect. Alternatively, such a high-resolution map can be generated from a combination of some ten-million known single nucleotide polymorphisms (SNPs) in the human genome. As used herein, a "SNP" is a common alteration that occurs in a single nucleotide base in a stretch of DNA. For example, a SNP may occur once per every 1000 bases of DNA. A SNP may be involved in a disease process, however, the vast majority may not be disease-associated. Given a genetic map based on the occurrence of such SNPs, individuals can be grouped into genetic categories depending on a particular pattern of SNPs in their individual genome. In such a manner, treatment regimens can be tailored to groups of genetically similar individuals, taking into account traits that may be common among such genetically similar individuals.

Alternatively, a method termed the "candidate gene approach," can be utilized to identify genes that predict drug response. According to this method, if a gene that encodes a drug's target is known (e.g., a 38692 or 21117 protein of the present invention), all common variants of that gene can be fairly easily identified in the population and it can be determined if having one version of the gene versus another is associated with a particular drug response.

Alternatively, a method termed "gene expression profiling," can be utilized to identify genes that predict drug response. For example, the gene expression of an animal dosed with a drug (e.g., a 38692 or 21117 molecule or 38692 or 21117 modulator of the present invention) can give an indication whether gene pathways related to toxicity have been turned on.

Information generated from more than one of the above pharmacogenomics approaches can be used to determine appropriate dosage and treatment regimens for prophylactic or therapeutic treatment of an individual. This knowledge, when applied to dosing or drug selection, can avoid adverse reactions or therapeutic failure and thus enhance therapeutic or prophylactic efficiency when treating a subject with a 38692 or 21117 molecule or 38692 or 21117 modulator, such as a modulator identified by one of the exemplary screening assays described herein.

The present invention further provides methods for identifying new agents, or combinations, that are based on identifying agents that modulate the activity of one or more of the gene products encoded by one or more of the 38692 or 21117 genes of the present invention, wherein these products may be associated with resistance of the cells to a therapeutic agent. Specifically, the activity of the proteins encoded by the 38692 or 21117 genes of the present invention can be used as a basis for identifying agents for overcoming agent resistance. By blocking the activity of one or more of the resistance proteins, target cells, e.g., cancer cells, will become sensitive to treatment with an agent that the unmodified target cells were resistant to.

Monitoring the influence of agents (e.g., drugs) on the expression or activity of a 38692 or 21117 protein can be applied in clinical trials. For example, the effectiveness of an agent determined by a screening assay as described herein to increase 38692 or 21117 gene expression, protein levels, or up-regulate 38692 or 21117 activity, can be monitored in clinical trials of subjects exhibiting decreased 38692 or 21117 gene expression, protein levels, or down-regulated 38692 or 21117 activity. Alternatively, the effectiveness of an agent determined by a screening assay to decrease 38692 or 21117 gene expression, protein levels, or down-regulate 38692 or 21117 activity, can be monitored in clinical trials of subjects exhibiting increased 38692 or 21117 gene expression, protein levels, or upregulated 38692 or 21117 activity. In such clinical trials, the expression or activity of a 38692 or 21117 gene, and preferably, other genes that have been implicated in, for example, a 38692 or 21117- associated disorder can be used as a "read out" or markers of the phenotype of a particular cell.

38692 or 21117 Informatics

The sequence of a 38692 or 21117 molecule is provided in a variety of media to facilitate use thereof. A sequence can be provided as a manufacture, other than an isolated nucleic acid or amino acid molecule, which contains a 38692 or 21117. Such a manufacture can provide a nucleotide or amino acid sequence, e.g., an open reading frame, in a form which allows examination of the manufacture using means not directly applicable to examining the nucleotide or amino acid sequences, or a subset thereof, as they exists in nature or in purified form. The sequence information can include, but is not limited to, 38692 or 21117 full-length nucleotide and/or amino acid sequences, partial nucleotide and/or amino acid sequences, polymorphic sequences including single nucleotide polymorphisms (SNPs), epitope sequence, and the like. In a preferred embodiment, the manufacture is a machine-readable medium, e.g., a magnetic, optical, chemical or mechanical information storage device.

As used herein, "machine-readable media" refers to any medium that can be read and accessed directly by a machine, e.g., a digital computer or analogue computer. Non-limiting examples of a computer include a desktop PC, laptop, mainframe, server (e.g., a web server, network server, or server farm), handheld digital assistant, pager, mobile telephone, and the like. The computer can be stand-alone or connected to a communications network, e.g., a local area network (such as a VPN or intranet), a wide area network (e.g., an Extranet or the Internet), or a telephone network (e.g., a wireless, DSL, or ISDN network). Machine-readable media include, but are not limited to: magnetic storage media, such as floppy discs, hard disc storage medium, and magnetic tape; optical storage media such as CD-ROM; electrical storage media such as RAM, ROM, EPROM, EEPROM, flash memory, and the like; and hybrids of these categories such as magnetic/optical storage media.

A variety of data storage structures are available to a skilled artisan for creating a machine-readable medium having recorded thereon a nucleotide or amino acid sequence of the present invention. The choice of the data storage structure will generally be based on the means chosen to access the stored information. In addition, a variety of data processor programs and formats can be used to store the nucleotide sequence information of the present invention on computer readable medium. The sequence information can be represented in a word processing text file, formatted in commercially-available software such as WordPerfect and Microsoft Word, or represented in the form of an ASCII file, stored in a database application, such as DB2, Sybase, Oracle, or the like. The skilled artisan can readily adapt any number of data processor structuring formats (e.g., text file or database) in order to obtain computer readable medium having recorded thereon the nucleotide sequence information of the present invention.

In a preferred embodiment, the sequence information is stored in a relational database (such as Sybase or Oracle). The database can have a first table for storing sequence (nucleic acid and/or amino acid sequence) information. The sequence information can be stored in one field (e.g., a first column) of a table row and an identifier for the sequence can be store in another field (e.g., a second column) of the table row. The database can have a second table, e.g., storing annotations. The second table can have a field for the sequence identifier, a field for a descriptor or annotation text (e.g., the descriptor can refer to a functionality of the sequence, a field for the initial position in the sequence to which the annotation refers, and a field for the ultimate position in the sequence to which the annotation refers. Non-limiting examples for annotation to nucleic acid sequences include polymorphisms (e.g., SNP's) translational regulatory sites and splice junctions. Non-limiting examples for annotations to amino acid sequence include polypeptide domains, e.g., a domain described herein; active sites and other functional amino acids; and modification sites.

By providing the nucleotide or amino acid sequences of the invention in computer readable form, the skilled artisan can routinely access the sequence information for a variety of purposes. For example, one skilled in the art can use the nucleotide or amino acid sequences of the invention in computer readable form to compare a target sequence or target structural motif with the sequence information stored within the data storage means. A search is used to identify fragments or regions of the sequences of the invention which match a particular target sequence or target motif. The search can be a BLAST search or other routine sequence comparison, e.g., a search described herein.

Thus, in one aspect, the invention features a method of analyzing 38692 or 21117, e.g., analyzing structure, function, or relatedness to one or more other nucleic acid or amino acid sequences. The method includes: providing a 38692 or 21117 nucleic acid or amino acid sequence; comparing the 38692 or 21117 sequence with a second sequence, e.g., one or more preferably a plurality of sequences from a collection of sequences, e.g., a nucleic acid or protein sequence database to thereby analyze 38692 or 21117. The method can be performed in a machine, e.g., a computer, or manually by a skilled artisan.

The method can include evaluating the sequence identity between a 38692 or 21117 sequence and a database sequence. The method can be performed by accessing the database at a second site, e.g., over the Internet.

As used herein, a "target sequence" can be any DNA or amino acid sequence of six or more nucleotides or two or more amino acids. A skilled artisan can readily recognize that the longer a target sequence is, the less likely a target sequence will be present as a random occurrence in the database. Typical sequence lengths of a target sequence are from about 10 to 100 amino acids or from about 30 to 300 nucleotide residues. However, it is well recognized that commercially important fragments, such as sequence fragments involved in gene expression and protein processing, may be of shorter length.

Computer software is publicly available which allows a skilled artisan to access sequence information provided in a computer readable medium for analysis and comparison to other sequences. A variety of known algorithms are disclosed publicly and a variety of commercially available software for conducting search means are and can be used in the computer-based systems of the present invention. Examples of such software include, but are not limited to, MacPattern (EMBL), BLASTN and BLASTX (NCBI).

Thus, the invention features a method of making a computer readable record of a sequence of a 38692 or 21117 sequence which includes recording the sequence on a computer readable matrix. In a preferred embodiment the record includes one or more of the following: identification of an ORF; identification of a domain, region, or site; identification of the start of transcription; identification of the transcription terminator; the full length amino acid sequence of the protein, or a mature form thereof; the 5' end of the translated region.

In another aspect, the invention features, a method of analyzing a sequence. The method includes: providing a 38692 or 21117 sequence, or record, in machine-readable form; comparing a second sequence to the 38692 or 21117 sequence; thereby analyzing a sequence. Comparison can include comparing to sequences for sequence identity or determining if one sequence is included within the other, e.g., determining if the 38692 or 21117 sequence includes a sequence being compared. In a preferred embodiment the 38692 or 21117 or second sequence is stored on a first computer, e.g., at a first site and the comparison is performed, read, or recorded on a second computer, e.g., at a second site. E.g., the 38692 or 21117 or second sequence can be stored in a public or proprietary database in one computer, and the results of the comparison performed, read, or recorded on a second computer. In a preferred embodiment the record includes one or more of the following: identification of an ORF; identification of a domain, region, or site; identification of the start of transcription; identification of the transcription terminator; the full length amino acid sequence of the protein, or a mature form thereof; the 5' end of the translated region.

In another aspect, the invention provides a machine-readable medium for holding instructions for performing a method for determining whether a subject has a 38692 or 21117-associated disease or disorder or a pre-disposition to a 38692 or 21117-associated disease or disorder, wherein the method comprises the steps of determining 38692 or 21117 sequence information associated with the subject and based on the 38692 or 21117 sequence information, determining whether the subject has a 38692 or 21117-associated disease or disorder or a pre-disposition to a 38692 or 21117-associated disease or disorder and/or recommending a particular treatment for the disease, disorder or pre-disease condition.

The invention further provides in an electronic system and/or in a network, a method for determining whether a subject has a 38692 or 21117-associated disease or disorder or a pre-disposition to a disease associated with a 38692 or 21117 wherein the method comprises the steps of determining 38692 or 21117 sequence information associated with the subject, and based on the 38692 or 21117 sequence information, determining whether the subject has a 38692 or 21117-associated disease or disorder or a pre-disposition to a 38692 or 21117-associated disease or disorder, and/or recommending a particular treatment for the disease, disorder or pre-disease condition. In a preferred embodiment, the method further includes the step of receiving information, e.g., phenotypic or genotypic information, associated with the subject and/or acquiring from a network phenotypic information associated with the subject. The information can be stored in a database, e.g., a relational database. In another embodiment, the method further includes accessing the database, e.g., for records relating to other subjects, comparing the 38692 or 21117 sequence of the subject to the 38692 or 21117 sequences in the database to thereby determine whether the subject as a 38692 or 21117-associated disease or disorder, or a pre-disposition for such.

The present invention also provides in a network, a method for determining whether a subject has a 38692 or 21117 associated disease or disorder or a pre-disposition to a 38692 or 21117-associated disease or disorder associated with 38692 or 21117, said method comprising the steps of receiving 38692 or 21117 sequence information from the subject and/or information related thereto, receiving phenotypic information associated with the subject, acquiring information from the network corresponding to 38692 or 21117 and/or corresponding to a 38692 or 21117-associated disease or disorder (e.g., a hematopoietic disorder (e.g., an erythroid, myeloid, monocyte, or megakaryocyte cell-associated disorder as described herein); or a cellular proliferation and/or differentiation disorder), and based on one or more of the phenotypic information, the 38692 or 21117 information (e.g., sequence information and/or information related thereto), and the acquired information, determining whether the subject has a 38692 or 21117-associated disease or disorder or a pre-disposition to a 38692 or 21117-associated disease or disorder. The method may further comprise the step of recommending a particular treatment for the disease, disorder or pre-disease condition.

The present invention also provides a method for determining whether a subject has a 38692 or 21117-associated disease or disorder or a pre-disposition to a 38692 or 21117-associated disease or disorder, said method comprising the steps of receiving information related to 38692 or 21117 (e.g., sequence information and/or information related thereto), receiving phenotypic information associated with the subject, acquiring information from the network related to 38692 or 21117 and/or related to a 38692 or 21117-associated disease or disorder, and based on one or more of the phenotypic information, the 38692 or 21117 information, and the acquired information, determining whether the subject has a 38692 or 21117-associated disease or disorder or a pre-disposition to a 38692 or 21117-associated disease or disorder. The method may further comprise the step of recommending a particular treatment for the disease, disorder or pre-disease condition.

This invention is further illustrated by the following examples that should not be construed as limiting. The contents of all references, patents and published patent applications cited throughout this application are incorporated herein by reference.

EXAMPLES

Example 1

Identification and Characterization of Human 38692 and 21117 cDNA

The human 21117 sequence (FIG. 1; SEQ ID NO:1), which is approximately 3544 nucleotides long including untranslated regions, contains a predicted methionine-initiated coding sequence of about 1998 nucleotides (nucleotides 589 to 2586 of SEQ ID NO:1; SEQ ID NO:3). The coding sequence encodes a 666 amino acid protein (SEQ ID NO:2).

The human 38692 sequence (FIG. 6; SEQ ID NO:4), which is approximately 1114 nucleotides long including untranslated regions, contains a predicted methionine-initiated coding sequence of about 672 nucleotides (nucleotides 89 to 760 of SEQ ID NO:4; SEQ ID NO:6). The coding sequence encodes a 224 amino acid protein (SEQ ID NO:5).

Example 2

Tissue Distribution of 38692 or 21117 mRNA

Endogenous human 21117 and 38692 gene expression was determined using the Perkin-Elmer/ABI 7700 Sequence Detection System which employs TaqMan technology. Briefly, TaqMan technology relies on standard RT-PCR with the addition of a third gene-specific oligonucleotide (referred to as a probe) which has a fluorescent dye coupled to its 5' end (typically 6-FAM) and a quenching dye at the 3' end (typically TAMRA). When the fluorescently tagged oligonucleotide is intact, the fluorescent signal from the 5' dye is quenched. As PCR proceeds, the 5' to 3' nucleolytic activity of Taq polymerase digests the labeled primer, producing a free nucleotide labeled with 6-FAM, which is now detected as a fluorescent signal. The PCR cycle where fluorescence is first released and detected is directly proportional to the starting amount of the gene of interest in the test sample, thus providing a way of quantitating the initial template concentration. Samples can be internally controlled by the addition of a second set of primers/probe specific for a housekeeping gene such as GAPDH which has been labeled with a different fluorophore on the 5' end (typically VIC).

To determine the level of 21117 mRNA in various human tissues a primer/probe set was designed using Primer Express (Perkin-Elmer) software and primary cDNA sequence information. Total RNA was prepared from a series of tissues using an RNeasy kit from Qiagen. First strand cDNA was prepared from 1 µg total RNA using an oligo-dT primer and Superscript II reverse transcriptase (Gibco/BRL). cDNA obtained from approximately 50 ng total RNA was used per TaqMan reaction.

Figure 10:
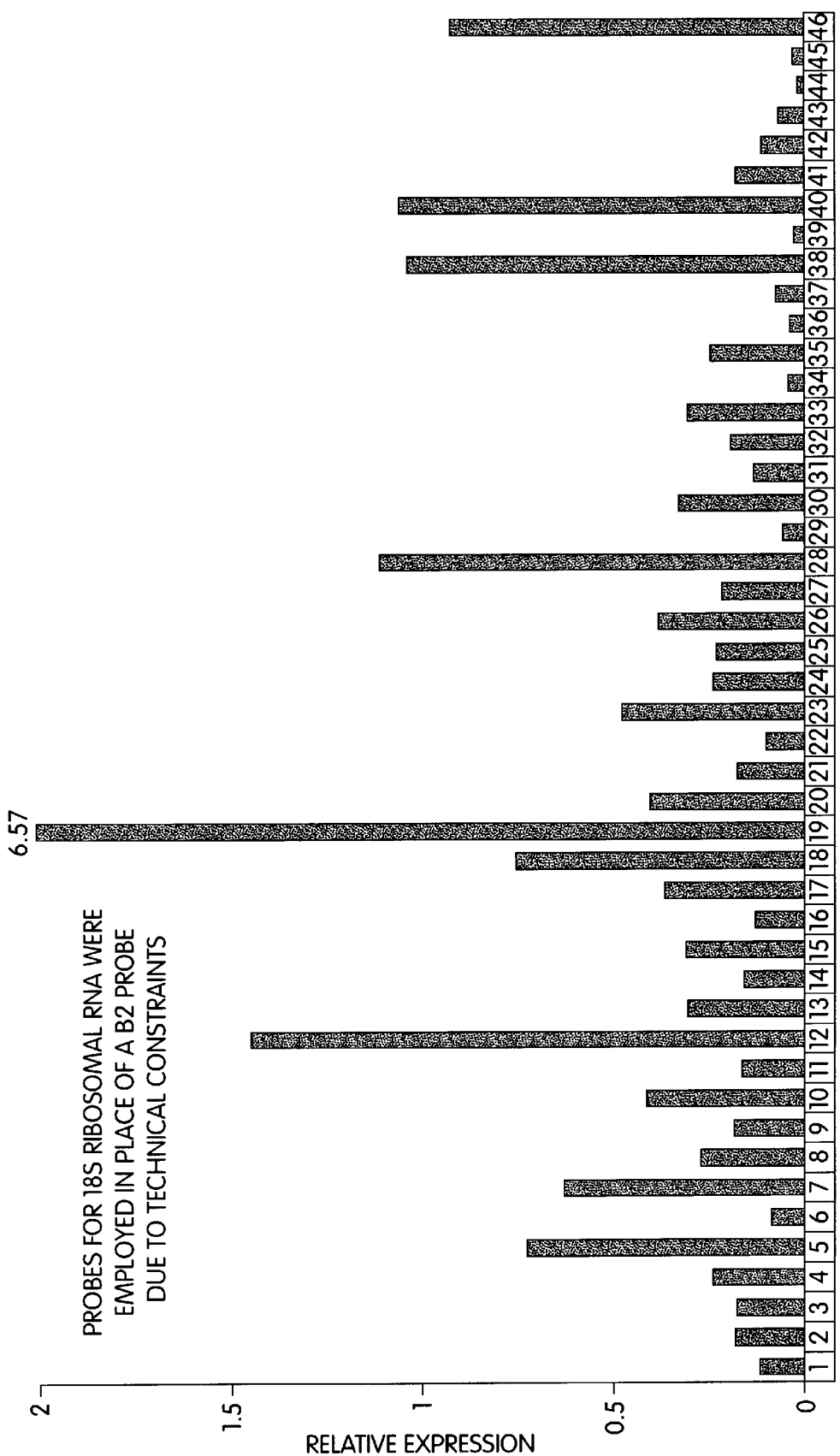
FIG. 10 shows a bar graph depicting relative 21117 mRNA expression as determined by TaqMan assays on mRNA derived from the following tissue samples. Columns are numbered at five-column intervals at the bottom of the Figure (i.e., columns 1–42), and correspond to the following: (1) Aorta/normal; (2) Fetal heart/normal; (3) Heart normal; (4) Heart/Coronary heart failure (CHF); (5) Vein/Normal; (6) SMC (Aortic); (7) Spinal cord/Normal; (8) Brain cortex/Normal; (9) Brain hypothalamus/Normal; (10) Glial cells (Astrocytes); (11) Brain/Glioblastoma; (12) Breast/Normal; (13) Breast tumor/IDC; (14) ovary/Normal; (15) ovary/Tumor; (16) Pancreas; (17) Prostate/Normal; (18) Prostate/Tumr; (19) Colon/normal; (20) Colon/tumor; (21) Colon/IBD (inflammatory bowel disease); (22) Kidney/normal; (23) Liver/normal; (24) Liver fibrosis; (25) Fetal Liver/normal; (26) Lung/normal; (27) Lung/tumor; (28) Lung/chronic obstructive pulmonary disease (COPD); (29) Spleen/normal; (30) Tonsil/normal; (31) Lymph node/normal; (32) Thymus/normal; (33) Epithelial Cells (prostate); (34) Endothelial Cells (aortic); (35) Skeletal Muscle/Normal; (36) Fibroblasts (Dermal); (37) Skin/normal; (38) Adipose/Normal; (39) Osteoblasts (primary); (40) Osteoblasts (undifferentiated); (41) Osteoblasts (differentiated); (42) Osteoclasts; (43) Aortic Smooth Muscle Cells (SMC) Early; (44) Aortic SMC Late; (45) Osteoclasts (undiff); (46) shear human umbilical vein endothelial cells (HUVEC). High relative levels of expression were detected in normal colon, normal breast, chronic obstructive pulmonary disease lung tissue, normal adipose tissue, and undifferentiated osteoblasts.

21117 mRNA levels were analyzed in a variety of tissue samples, both normal and diseased, including heart tissues, CNS tissues, breast, ovary, pancreas, prostate, colon, kidney, liver, lung, spleen, tonsil, skeletal muscle, smooth muscle, skin, adipose, osteoblasts, and osteoclasts. High relative levels of expression were detected in normal colon, normal breast, chronic obstructive pulmonary disease lung tissue, normal adipose tissue, and undifferentiated osteoblasts (FIG. 10).

Figure 12:
FIG. 12 shows a bar graph depicting relative 38692 mRNA expression as determined by TaqMan assays on mRNA derived from the following hematological cell lines. Columns are numbered at five-column intervals at the bottom of the Figure (i.e., columns 1–50), and correspond to cells from the following tissue or cell types: (1) Lung; (2) Colon; (3) Heart; (4) Spleen; (5) Kidney; (6) Liver NDR 200; (7) Fetal Liver; (8) Skeletal Muscle; (9) m BM (bone marrow) mononuclear cells (MNC); (10) mBM MNC LP7; (11) mBM CD34+LP92; (12) mobilized peripheral blood (mPB) CD34+LF41; (13) mPB CD34+LF48; (14) adult bone marrow (ABM) CD34+LP91; (15) ABM CD34+LP29; (16) Cord Blood CD34+LF109; (17) Fetal Liver CD34+LP93; (18) Fetal Liver CD34+LP45; (19) Bone Marrow Glycophorin A positive (BM GPA+) LP85; (20) BM GPA+ LP34-1; (21) BM GPA low CD71+LF38; (22) BM GPA low CD71+LP85-2; (23) mobilized peripheral blood (mPB) CD41+/CD14-LP94; (24) BM CD41+/CD14-LP78; (25) mBM CD15+LP15; (26) mBM CD15+/CD11b-LP7-4; (27)

38692 expression was determined by TaqMan assays on mRNA derived from various tissues and cell lines, including lung, colon, heart, kidney, spleen, liver cell lines, and various hematopoietic cell lines, including, inter alia, bone marrow cells, mononuclear cells, peripheral blood, CD34+ cells, erythrocytes, magakaryocytes, and neutrophils (FIGS. 11–12). In some samples, mRNA expression was detected at the indicated times in culture (e.g., 24 hrs., 48 hrs., days in culture).

High relative levels of 38692 expression were found in hepatic tissues (e.g., fetal liver cells, HepG2.2.15-A liver cells, fetal liver CD34+ cells), and in hematopoietic celsl ssuch as K562 cells, Bone Marrow Glycophorin A (BM GPA) low CD71+LF38; and BM GPA low CD71+LP85-2 (FIGS. 11–12).

Example 3

Recombinant Expression of 38692 or 21117 in Bacterial Cells

In this example, 38692 or 21117 is expressed as a recombinant glutathione-S-transferase (GST) fusion polypeptide in *E. coli* and the fusion polypeptide is isolated and characterized. Specifically, 38692 or 21117 is fused to GST and this fusion polypeptide is expressed in *E. coli*, e.g., strain PEB199. Expression of the GST-38692 or 21117 fusion protein in PEB199 is induced with IPTG. The recombinant fusion polypeptide is purified from crude bacterial lysates of the induced PEB199 strain by affinity chromatography on glutathione beads. Using polyacrylamide gel electrophoretic analysis of the polypeptide purified from the bacterial lysates, the molecular weight of the resultant fusion polypeptide is determined.

Example 4

Expression of Recombinant 38692 or 21117 Protein in COS Cells

To express the 38692 or 21117 gene in COS cells, the pcDNA/Amp vector by Invitrogen Corporation (San Diego, Calif.) is used. This vector contains an SV40 origin of replication, an ampicillin resistance gene, an *E. coli* replication origin, a CMV promoter followed by a polylinker region, and an SV40 intron and polyadenylation site. A DNA fragment encoding the entire 38692 or 21117 protein and an HA tag (Wilson et al. (1984) *Cell* 37:767) or a FLAG tag fused in-frame to its 3' end of the fragment is cloned into the polylinker region of the vector, thereby placing the expression of the recombinant protein under the control of the CMV promoter.

To construct the plasmid, the 38692 or 21117 DNA sequence is amplified by PCR using two primers. The 5' primer contains the restriction site of interest followed by approximately twenty nucleotides of the 38692 or 21117 coding sequence starting from the initiation codon; the 3' end sequence contains complementary sequences to the other restriction site of interest, a translation stop codon, the HA tag or FLAG tag and the last 20 nucleotides of the 38692 or 21117 coding sequence. The PCR amplified fragment and the pCDNA/Amp vector are digested with the appropriate restriction enzymes and the vector is dephosphorylated using the CIAP enzyme (New England Biolabs, Beverly, Mass). Preferably the two restriction sites chosen are different so that the 38692 or 21117 gene is inserted in the correct orientation. The ligation mixture is transformed into *E. coli* cells (strains HB101, DH5α, SURE, available from Stratagene Cloning Systems, La Jolla, Calif., can be used), the transformed culture is plated on ampicillin media plates, and resistant colonies are selected. Plasmid DNA is isolated from transformants and examined by restriction analysis for the presence of the correct fragment.

COS cells are subsequently transfected with the 38692 or 21117-pcDNA/Amp plasmid DNA using the calcium phosphate or calcium chloride co-precipitation methods, DEAE-dextran-mediated transfection, lipofection, or electroporation. Other suitable methods for transfecting host cells can be found in Sambrook, J., Fritsh, E. F., and Maniatis, T. *Molecular Cloning: A Laboratory Manual. 2nd, ed., Cold Spring Harbor Laboratory*, Cold Spring Harbor Laboratory Press, Cold Spring Harbor, N.Y., 1989. The expression of the 38692 or 21117 polypeptide is detected by radiolabeling ($^{35}$S-methionine or $^{35}$S-cysteine available from NEN, Boston, Mass., can be used) and immunoprecipitation (Harlow, E. and Lane, D. *Antibodies: A Laboratory Manual*, Cold Spring Harbor Laboratory Press, Cold Spring Harbor, N.Y., 1988) using an HA specific monoclonal antibody. Briefly, the cells are labeled for 8 hours with $^{35}$S-methionine (or $^{35}$S-cysteine). The culture media are then collected and the cells are lysed using detergents (RIPA buffer, 150 mM NaCl, 1% NP-40, 0.1% SDS, 0.5% DOC, 50 mM Tris, pH 7.5). Both the cell lysate and the culture media are precipitated with an HA specific monoclonal antibody. Precipitated polypeptides are then analyzed by SDS-PAGE.

Alternatively, DNA containing the 38692 or 21117 coding sequence is cloned directly into the polylinker of the pCDNA/Amp vector using the appropriate restriction sites. The resulting plasmid is transfected into COS cells in the manner described above, and the expression of the 38692 or 21117 polypeptide is detected by radiolabelling and immunoprecipitation using a 38692 or 21117 specific monoclonal antibody.

Equivalents

Those skilled in the art will recognize, or be able to ascertain using no more than routine experimentation, many equivalents to the specific embodiments of the invention described herein. Such equivalents are intended to be encompassed by the following claims.

SEQUENCE LISTING

<160> NUMBER OF SEQ ID NOS: 10

<210> SEQ ID NO 1
<211> LENGTH: 3544
<212> TYPE: DNA
<213> ORGANISM: Homo sapiens
<220> FEATURE:
<221> NAME/KEY: CDS
<222> LOCATION: (589)...(2583)

<400> SEQUENCE: 1

```
tcctataggg agtcgcccg cgtccgaaaa gattataagt aaatactctg ctctttcaag      60
tgaaccaaac ctatcaaacc tgtttagaaa ataaaccagg cagaataaaa tgatgcgaaa    120
tgttcatttt aaaaaacttc aggatgggca caaacacaca gaagtgggaa atgaataaaa    180
gagtattgat aaattttga aaattgttga agctgagtaa tgggctttca gtccagtgta     240
aagctgttgg agcgcgggag caaaggtaaa gaatgatgta atgcgctggc tgctccaaag    300
catcttttgt tgtggaatgg ttattccagt catctcttta tgaatcaaat gtgaggggct    360
gctttgtgga cggagtcctt tgcaagagca catcaacggg aaagagaaag agacattcac    420
ttggagggct cttgctgaaa atgggtttaa ctctcctttt gccagtcacc accagcctga    480
cctcatacac ttttagtaca atggagtggc tgagcctttg agcacaccac cattacatca    540
tcgtggcaaa ttaaagaagg aggtgggaaa agaggactta ttgttgtc atg gcc cat    597
                                                    Met Ala His
                                                     1 gag atg att gga act caa att gtt act gag agg ttg gtg gct ctg ctg    645
Glu Met Ile Gly Thr Gln Ile Val Thr Glu Arg Leu Val Ala Leu Leu
         5                  10                  15 gaa agt gga acg gaa aaa gtg ctg cta att gat agc cgg cca ttt gtg    693
Glu Ser Gly Thr Glu Lys Val Leu Leu Ile Asp Ser Arg Pro Phe Val
 20                  25                  30                  35 gaa tac aat aca tcc cac att ttg gaa gcc att aat atc aac tgc tcc    741
Glu Tyr Asn Thr Ser His Ile Leu Glu Ala Ile Asn Ile Asn Cys Ser
             40                  45                  50 aag ctt atg aag cga agg ttg caa cag gac aaa gtg tta att aca gag    789
Lys Leu Met Lys Arg Arg Leu Gln Gln Asp Lys Val Leu Ile Thr Glu
         55                  60                  65 ctc atc cag cat tca gcg aaa cat aag gtt gac att gat tgc agt cag    837
Leu Ile Gln His Ser Ala Lys His Lys Val Asp Ile Asp Cys Ser Gln
     70                  75                  80 aag gtt gta gtt tac gat caa agc tcc caa gat gtt gcc tct ctc tct    885
Lys Val Val Val Tyr Asp Gln Ser Ser Gln Asp Val Ala Ser Leu Ser
 85                  90                  95 tca gac tgt ttt ctc act gta ctt ctg ggt aaa ctg gag aag agc ttc    933
Ser Asp Cys Phe Leu Thr Val Leu Leu Gly Lys Leu Glu Lys Ser Phe
100                 105                 110                 115 aac tct gtt cac ctg ctt gca ggt ggg ttt gct gag ttc tct cgt tgt    981
Asn Ser Val His Leu Leu Ala Gly Gly Phe Ala Glu Phe Ser Arg Cys
             120                 125                 130 ttc cct ggc ctc tgt gaa gga aaa tcc act cta gtc cct acc tgc att   1029
```

-continued

| | | |
|---|---|---|
| Phe Pro Gly Leu Cys Glu Gly Lys Ser Thr Leu Val Pro Thr Cys Ile<br>                    135                  140                145 | | |
| tct cag cct tgc tta cct gtt gcc aac att ggg cca acc cga att ctt<br>Ser Gln Pro Cys Leu Pro Val Ala Asn Ile Gly Pro Thr Arg Ile Leu<br>         150                  155                  160 | 1077 |
| ccc aat ctt tat ctt ggc tgc cag cga gat gtc ctc aac aag gag ctg<br>Pro Asn Leu Tyr Leu Gly Cys Gln Arg Asp Val Leu Asn Lys Glu Leu<br>        165                  170                  175 | 1125 |
| atg cag cag aat ggg att ggt tat gtg tta aat gcc agc aat acc tgt<br>Met Gln Gln Asn Gly Ile Gly Tyr Val Leu Asn Ala Ser Asn Thr Cys<br>180                  185                  190                  195 | 1173 |
| cca aag cct gac ttt atc ccc gag tct cat ttc ctg cgt gtg cct gtg<br>Pro Lys Pro Asp Phe Ile Pro Glu Ser His Phe Leu Arg Val Pro Val<br>                    200                  205                  210 | 1221 |
| aat gac agc ttt tgt gag aaa att ttg ccg tgg ttg gac aaa tca gta<br>Asn Asp Ser Phe Cys Glu Lys Ile Leu Pro Trp Leu Asp Lys Ser Val<br>                215                  220                  225 | 1269 |
| gat ttc att gag aaa gca aaa gcc tcc aat gga tgt gtt cta gtg cac<br>Asp Phe Ile Glu Lys Ala Lys Ala Ser Asn Gly Cys Val Leu Val His<br>            230                  235                  240 | 1317 |
| tgt tta gct ggg atc tcc cgc tcc gcc acc atc gct atc gcc tac atc<br>Cys Leu Ala Gly Ile Ser Arg Ser Ala Thr Ile Ala Ile Ala Tyr Ile<br>        245                  250                  255 | 1365 |
| atg aag agg atg gac atg tct tta gat gaa gct tac aga ttt gtg aaa<br>Met Lys Arg Met Asp Met Ser Leu Asp Glu Ala Tyr Arg Phe Val Lys<br>260                  265                  270                  275 | 1413 |
| gaa aaa aga cct act ata tct cca aac ttc aat ttt ctg ggc caa ctc<br>Glu Lys Arg Pro Thr Ile Ser Pro Asn Phe Asn Phe Leu Gly Gln Leu<br>                    280                  285                  290 | 1461 |
| ctg gac tat gag aag aag att aag aac cag act gga gca tca ggg cca<br>Leu Asp Tyr Glu Lys Lys Ile Lys Asn Gln Thr Gly Ala Ser Gly Pro<br>                295                  300                  305 | 1509 |
| aag agc aaa ctc aag ctg ctg cac ctg gag aag cca aat gaa cct gtc<br>Lys Ser Lys Leu Lys Leu Leu His Leu Glu Lys Pro Asn Glu Pro Val<br>            310                  315                  320 | 1557 |
| cct gct gtc tca gag ggt gga cag aaa agc gag acg ccc ctc agt cca<br>Pro Ala Val Ser Glu Gly Gly Gln Lys Ser Glu Thr Pro Leu Ser Pro<br>        325                  330                  335 | 1605 |
| ccc tgt gcc gac tct gct acc tca gag gca gca gga caa agg ccc gtg<br>Pro Cys Ala Asp Ser Ala Thr Ser Glu Ala Ala Gly Gln Arg Pro Val<br>340                  345                  350                  355 | 1653 |
| cat ccc gcc agc gtg ccc agc gtg ccc agc gtg cag ccg tcg ctg tta<br>His Pro Ala Ser Val Pro Ser Val Pro Ser Val Gln Pro Ser Leu Leu<br>                    360                  365                  370 | 1701 |
| gag gac agc ccg ctg gta cag gcg ctc agt ggg ctg cac ctg tcc gca<br>Glu Asp Ser Pro Leu Val Gln Ala Leu Ser Gly Leu His Leu Ser Ala<br>              375                  380                  385 | 1749 |
| gac agg ctg gaa gac agc aat aag ctc aag cgt tcc ttc tct ctg gat<br>Asp Arg Leu Glu Asp Ser Asn Lys Leu Lys Arg Ser Phe Ser Leu Asp<br>            390                  395                  400 | 1797 |
| atc aaa tca gtt tca tat tca gcc agc atg gca gca tcc tta cat ggc<br>Ile Lys Ser Val Ser Tyr Ser Ala Ser Met Ala Ala Ser Leu His Gly<br>        405                  410                  415 | 1845 |
| ttc tcc tca tca gaa gat gct ttg gaa tac tac aaa cct tcc act act<br>Phe Ser Ser Ser Glu Asp Ala Leu Glu Tyr Tyr Lys Pro Ser Thr Thr<br>420                  425                  430                  435 | 1893 |
| ctg gat ggg acc aac aag cta tgc cag ttc tcc cct gtt cag gaa cta<br>Leu Asp Gly Thr Asn Lys Leu Cys Gln Phe Ser Pro Val Gln Glu Leu<br>                    440                  445                  450 | 1941 |

-continued

| | |
|---|---|
| tcg gag cag act ccc gaa acc agt cct gat aag gag gaa gcc agc atc<br>Ser Glu Gln Thr Pro Glu Thr Ser Pro Asp Lys Glu Glu Ala Ser Ile<br>455                    460                    465 | 1989 |
| ccc aag aag ctg cag acc gcc agg cct tca gac agc cag agc aag cga<br>Pro Lys Lys Leu Gln Thr Ala Arg Pro Ser Asp Ser Gln Ser Lys Arg<br>          470                    475                    480 | 2037 |
| ttg cat tcg gtc aga acc agc agc agt ggc acc gcc cag agg tcc ctt<br>Leu His Ser Val Arg Thr Ser Ser Ser Gly Thr Ala Gln Arg Ser Leu<br>485                    490                    495 | 2085 |
| tta tct cca ctg cat cga agt ggg agc gtg gag gac aat tac cac acc<br>Leu Ser Pro Leu His Arg Ser Gly Ser Val Glu Asp Asn Tyr His Thr<br>500                    505                    510                  515 | 2133 |
| agc ttc ctt ttc ggc ctt tcc acc agc cag cag cac ctc acg aag tct<br>Ser Phe Leu Phe Gly Leu Ser Thr Ser Gln Gln His Leu Thr Lys Ser<br>                    520                    525                    530 | 2181 |
| gct ggc ctg ggc ctt aag ggc tgg cac tcg gat atc ttg gcc ccc cag<br>Ala Gly Leu Gly Leu Lys Gly Trp His Ser Asp Ile Leu Ala Pro Gln<br>535                    540                    545 | 2229 |
| acc tct acc cct tcc ctg acc agc agc tgg tat ttt gcc aca gag tcc<br>Thr Ser Thr Pro Ser Leu Thr Ser Ser Trp Tyr Phe Ala Thr Glu Ser<br>          550                    555                    560 | 2277 |
| tca cac ttc tac tct gcc tca gcc atc tac gga ggc agt gcc agt tac<br>Ser His Phe Tyr Ser Ala Ser Ala Ile Tyr Gly Gly Ser Ala Ser Tyr<br>565                    570                    575 | 2325 |
| tct gcc tac agc tgc agc cag ctg ccc act tgc gga gac caa gtc tat<br>Ser Ala Tyr Ser Cys Ser Gln Leu Pro Thr Cys Gly Asp Gln Val Tyr<br>580                    585                    590                  595 | 2373 |
| tct gtg cgc agg cgg cag aag cca agt gac aga gct gac tcg cgg cgg<br>Ser Val Arg Arg Arg Gln Lys Pro Ser Asp Arg Ala Asp Ser Arg Arg<br>                    600                    605                    610 | 2421 |
| agc tgg cat gaa gag agc ccc ttt gaa aag cag ttt aaa cgc aga agc<br>Ser Trp His Glu Glu Ser Pro Phe Glu Lys Gln Phe Lys Arg Arg Ser<br>615                    620                    625 | 2469 |
| tgc caa atg gaa ttt gga gag agc atc atg tca gag aac agg tca cgg<br>Cys Gln Met Glu Phe Gly Glu Ser Ile Met Ser Glu Asn Arg Ser Arg<br>          630                    635                    640 | 2517 |
| gaa gag ctg ggg aaa gtg ggc agt cag tct agc ttt tcg ggc agc atg<br>Glu Glu Leu Gly Lys Val Gly Ser Gln Ser Ser Phe Ser Gly Ser Met<br>645                    650                    655 | 2565 |
| gaa atc att gag gtc tcc tgagaagaaa gacacttgtg acttctatag<br>Glu Ile Ile Glu Val Ser<br>660                    665 | 2613 |
| acaatttttt tttcttgttc acaaaaaaat tccctgtaaa tctgaaatat atatatgtac | 2673 |
| atacatatat atttttggaa aatggagcta tggtgtaaaa gcaacaggtg gatcaaccca | 2733 |
| gttgttactc tcttaacatc tgcatttgag agatcagcta atacttctct caacaaaaat | 2793 |
| ggaagggcag atgctagaat ccccctaga cggaggaaaa ccattttatt cagtgaatta | 2853 |
| cacatcctct tgttcttaaa aaagcaagtg tctttggtgt tggaggacaa aatcccctac | 2913 |
| cattttcacg ttgtgctact aagagatctc aaatattagt ctttgtccgg acccttccat | 2973 |
| agtacacctt agcgctgaga ctgagccagc ttggggggtca ggtaggtaga ccctgttagg | 3033 |
| gacagagcct agtggtaaat ccaagagaaa tgatcctatc caaagctgat tcacaaaccc | 3093 |
| acgctcacct gacagccgag ggacacgagc atcactctgc tggacggacc attaggggcc | 3153 |
| ttgccaaggt ctaccttaga gcaaacccag tacctcagac aggaaagtcg gggctttgac | 3213 |
| cactaccata tctggtagcc cattttctag gcattgtgaa taggtaggta gctagtcaca | 3273 |
| cttttcagac caattcaaac tgtctatgca caaaattccc gtgggcctag atggagataa | 3333 |

```
ttttttttttc ttctcagctt tatgaagaga agggaaactg tctaggattc agctgaacca      3393
ccaggaacct ggcaacatca cgatttaagc taaggttggg aggctaacga gtctacctcc      3453
ctctttgtaa atcaaagaat tgtttaaaat gggattgtca atcctttaaa taaagatgaa      3513
cttggtttca aaaaaaaaaa aaaaaaaaag                                       3544
```

<210> SEQ ID NO 2
<211> LENGTH: 665
<212> TYPE: PRT
<213> ORGANISM: Homo sapiens

<400> SEQUENCE: 2

```
Met Ala His Glu Met Ile Gly Thr Gln Ile Val Thr Glu Arg Leu Val
  1               5                  10                  15

Ala Leu Glu Ser Gly Thr Glu Lys Val Leu Leu Ile Asp Ser Arg
             20                  25                  30

Pro Phe Val Glu Tyr Asn Thr Ser His Ile Leu Glu Ala Ile Asn Ile
             35                  40                  45

Asn Cys Ser Lys Leu Met Lys Arg Arg Leu Gln Gln Asp Lys Val Leu
 50                  55                  60

Ile Thr Glu Leu Ile Gln His Ser Ala Lys His Lys Val Asp Ile Asp
 65                  70                  75                  80

Cys Ser Gln Lys Val Val Tyr Asp Gln Ser Ser Gln Asp Val Ala
             85                  90                  95

Ser Leu Ser Ser Asp Cys Phe Leu Thr Val Leu Leu Gly Lys Leu Glu
            100                 105                 110

Lys Ser Phe Asn Ser Val His Leu Leu Ala Gly Gly Phe Ala Glu Phe
            115                 120                 125

Ser Arg Cys Phe Pro Gly Leu Cys Glu Gly Lys Ser Thr Leu Val Pro
            130                 135                 140

Thr Cys Ile Ser Gln Pro Cys Leu Pro Val Ala Asn Ile Gly Pro Thr
145                 150                 155                 160

Arg Ile Leu Pro Asn Leu Tyr Leu Gly Cys Gln Arg Asp Val Leu Asn
                165                 170                 175

Lys Glu Leu Met Gln Gln Asn Gly Ile Gly Tyr Val Leu Asn Ala Ser
                180                 185                 190

Asn Thr Cys Pro Lys Pro Asp Phe Ile Pro Glu Ser His Phe Leu Arg
            195                 200                 205

Val Pro Val Asn Asp Ser Phe Cys Glu Lys Ile Leu Pro Trp Leu Asp
            210                 215                 220

Lys Ser Val Asp Phe Ile Glu Lys Ala Lys Ala Ser Asn Gly Cys Val
225                 230                 235                 240

Leu Val His Cys Leu Ala Gly Ile Ser Arg Ser Ala Thr Ile Ala Ile
                245                 250                 255

Ala Tyr Ile Met Lys Arg Met Asp Met Ser Leu Asp Glu Ala Tyr Arg
                260                 265                 270

Phe Val Lys Glu Lys Arg Pro Thr Ile Ser Pro Asn Phe Asn Phe Leu
            275                 280                 285

Gly Gln Leu Leu Asp Tyr Glu Lys Lys Ile Lys Asn Gln Thr Gly Ala
            290                 295                 300

Ser Gly Pro Lys Ser Lys Leu Lys Leu Leu His Leu Glu Lys Pro Asn
305                 310                 315                 320

Glu Pro Val Pro Ala Val Ser Glu Gly Gly Gln Lys Ser Glu Thr Pro
                325                 330                 335
```

```
Leu Ser Pro Pro Cys Ala Asp Ser Ala Thr Ser Glu Ala Ala Gly Gln
            340                 345                 350
Arg Pro Val His Pro Ala Ser Val Pro Ser Val Pro Ser Val Gln Pro
            355                 360                 365
Ser Leu Leu Glu Asp Ser Pro Leu Val Gln Ala Leu Ser Gly Leu His
    370                 375                 380
Leu Ser Ala Asp Arg Leu Glu Asp Ser Asn Lys Leu Lys Arg Ser Phe
385                 390                 395                 400
Ser Leu Asp Ile Lys Ser Val Ser Tyr Ser Ala Ser Met Ala Ala Ser
                405                 410                 415
Leu His Gly Phe Ser Ser Glu Asp Ala Leu Glu Tyr Tyr Lys Pro
            420                 425                 430
Ser Thr Thr Leu Asp Gly Thr Asn Lys Leu Cys Gln Phe Ser Pro Val
            435                 440                 445
Gln Glu Leu Ser Glu Gln Thr Pro Glu Thr Ser Pro Asp Lys Glu Glu
    450                 455                 460
Ala Ser Ile Pro Lys Lys Leu Gln Thr Ala Arg Pro Ser Asp Ser Gln
465                 470                 475                 480
Ser Lys Arg Leu His Ser Val Arg Thr Ser Ser Gly Thr Ala Gln
                485                 490                 495
Arg Ser Leu Leu Ser Pro Leu His Arg Ser Gly Ser Val Glu Asp Asn
            500                 505                 510
Tyr His Thr Ser Phe Leu Phe Gly Leu Ser Thr Ser Gln Gln His Leu
            515                 520                 525
Thr Lys Ser Ala Gly Leu Gly Leu Lys Gly Trp His Ser Asp Ile Leu
            530                 535                 540
Ala Pro Gln Thr Ser Thr Pro Ser Leu Thr Ser Ser Trp Tyr Phe Ala
545                 550                 555                 560
Thr Glu Ser Ser His Phe Tyr Ser Ala Ser Ala Ile Tyr Gly Gly Ser
                565                 570                 575
Ala Ser Tyr Ser Ala Tyr Ser Cys Ser Gln Leu Pro Thr Cys Gly Asp
            580                 585                 590
Gln Val Tyr Ser Val Arg Arg Arg Gln Lys Pro Ser Asp Arg Ala Asp
            595                 600                 605
Ser Arg Arg Ser Trp His Glu Glu Ser Pro Phe Glu Lys Gln Phe Lys
    610                 615                 620
Arg Arg Ser Cys Gln Met Glu Phe Gly Glu Ser Ile Met Ser Glu Asn
625                 630                 635                 640
Arg Ser Arg Glu Glu Leu Gly Lys Val Gly Ser Gln Ser Ser Phe Ser
                645                 650                 655
Gly Ser Met Glu Ile Ile Glu Val Ser
            660                 665

<210> SEQ ID NO 3
<211> LENGTH: 1998
<212> TYPE: DNA
<213> ORGANISM: Homo sapiens

<400> SEQUENCE: 3
atggcccatg agatgattgg aactcaaatt gttactgaga ggttggtggc tctgctggaa      60
agtggaacgg aaaaagtgct gctaattgat agccggccat ttgtggaata caatacatcc     120
cacattttgg aagccattaa tatcaactgc tccaagctta tgaagcgaag gttgcaacag     180
gacaaagtgt taattacaga gctcatccag cattcagcga acataaggt tgacattgat     240
```

-continued

```
tgcagtcaga aggttgtagt ttacgatcaa agctcccaag atgttgcctc tctctcttca      300
gactgttttc tcactgtact tctgggtaaa ctggagaaga gcttcaactc tgttcacctg      360
cttgcaggtg ggtttgctga gttctctcgt tgtttccctg gcctctgtga aggaaaatcc      420
actctagtcc ctacctgcat ttctcagcct tgcttacctg ttgccaacat tgggccaacc      480
cgaattcttc ccaatcttta tcttggctgc agcgagatg tcctcaacaa ggagctgatg       540
cagcagaatg ggattggtta tgtgttaaat gccagcaata cctgtccaaa gcctgacttt      600
atccccgagt ctcatttcct gcgtgtgcct gtgaatgaca gcttttgtga gaaaattttg      660
ccgtggttgg acaaatcagt agatttcatt gagaaagcaa agcctccaa tggatgtgtt       720 ctagtgcact gtttagctgg gatctcccgc tccgccacca cgctatcgc ctacatcatg       780 aagaggatgg acatgtcttt agatgaagct tacagatttg tgaaagaaaa agacctact      840 atatctccaa acttcaattt tctgggccaa ctcctggact atgagaagaa gattaagaac      900
cagactggag catcagggcc aaagagcaaa ctcaagctgc tgcacctgga gagccaaat      960 gaacctgtcc ctgctgtctc agagggtgga cagaaaagcg acgcccct cagtccaccc       1020 tgtgccgact ctgctacctc agaggcagca ggacaaaggc ccgtgcatcc cgccagcgtg     1080
cccagcgtgc ccagcgtgca gccgtcgctg ttagaggaca gcccgctggt acaggcgctc      1140
agtgggctgc acctgtccgc agacaggctg gaagacagca ataagctcaa gcgttccttc     1200
tctctggata tcaaatcagt ttcatattca gccagcatgg cagcatcctt acatggcttc     1260
tcctcatcag aagatgcttt ggaatactac aaaccttcca ctactctgga tgggaccaac     1320
aagctatgcc agttctcccc tgttcaggaa ctatcggagc agactcccga accagtcct     1380 gataaggagg aagccagcat ccccaagaag ctgcagaccg ccaggccttc agacagccag     1440
agcaagcgat tgcattcgt cagaaccagc agcagtggca ccgcccagag gtccctttta     1500
tctccactgc atcgaagtgg gagcgtggag gacaattacc acaccagctt cctttcggc      1560 ctttccacca gccagcagca cctcacgaag tctgctggcc tgggccttaa gggctggcac     1620
tcggatatct ggccccccca gacctctacc ccttccctga ccagcagctg gtattttgcc     1680
acagagtcct cacacttcta ctctgcctca gccatctacg gaggcagtgc cagttactct     1740
gcctacagct gcagccagct gcccacttgc ggagaccaag tctattctgt gcgcaggcgg     1800
cagaagccaa gtgacagagc tgactcgcgg cggagctggc atgaagagag cccctttgaa     1860
aagcagttta acgcagaag ctgccaaatg gaatttggag agagcatcat gtcagagaac      1920
aggtcacggg aagagctggg gaaagtgggc agtcagtcta gcttttcggg cagcatggaa     1980
atcattgagg tctcctga                                                    1998
```

<210> SEQ ID NO 4
<211> LENGTH: 1114
<212> TYPE: DNA
<213> ORGANISM: Homo sapiens
<220> FEATURE:
<221> NAME/KEY: CDS
<222> LOCATION: (89)...(757)

<400> SEQUENCE: 4

```
ctatagggag tcgcccacgc gtccggggcg gtggcgcgct gacacctggc ggcggcggag      60
ggcgggcaga agcccgcggg ccagcacc atg gag gac gtg aag ctg gag ttc       112
                               Met Glu Asp Val Lys Leu Glu Phe
                                 1               5 cct tcc ctt cca cag tgc aag gaa gac gcc gag gag tgg acc tac cct      160
```

```
                Pro Ser Leu Pro Gln Cys Lys Glu Asp Ala Glu Glu Trp Thr Tyr Pro
                    10                  15                  20 atg aga cga gag atg cag gaa att tta cct gga ttg ttc tta ggc cca         208
Met Arg Arg Glu Met Gln Glu Ile Leu Pro Gly Leu Phe Leu Gly Pro
 25                  30                  35                  40 tat tca tct gct atg aaa agc aag cta cct gta cta cag aaa cat gga         256
Tyr Ser Ser Ala Met Lys Ser Lys Leu Pro Val Leu Gln Lys His Gly
                 45                  50                  55 ata acc cat ata ata tgc ata cga caa aat att gaa gca aac ttt att         304
Ile Thr His Ile Ile Cys Ile Arg Gln Asn Ile Glu Ala Asn Phe Ile
             60                  65                  70 aaa cca aac ttt cag cag tta ttt aga tat tta gtc ctg gat att gca         352
Lys Pro Asn Phe Gln Gln Leu Phe Arg Tyr Leu Val Leu Asp Ile Ala
         75                  80                  85 gat aat cca gtt gaa aat ata ata cgt ttt ttc cct atg act aag gaa         400
Asp Asn Pro Val Glu Asn Ile Ile Arg Phe Phe Pro Met Thr Lys Glu
     90                  95                 100 ttt att gat ggg agc tta caa atg gga gga aaa gtt ctt gtg cat gga         448
Phe Ile Asp Gly Ser Leu Gln Met Gly Gly Lys Val Leu Val His Gly
105                 110                 115                 120 aat gca ggg atc tcc aga agt gca gcc ttt gtt att gca tac att atg         496
Asn Ala Gly Ile Ser Arg Ser Ala Ala Phe Val Ile Ala Tyr Ile Met
                125                 130                 135 gaa aca ttt gga atg aag tac aga gat gct ttt gct tat gtt caa gaa         544
Glu Thr Phe Gly Met Lys Tyr Arg Asp Ala Phe Ala Tyr Val Gln Glu
            140                 145                 150 aga aga ttt tgt att aat cct aat gct gga ttt gtc cat caa ctt cag         592
Arg Arg Phe Cys Ile Asn Pro Asn Ala Gly Phe Val His Gln Leu Gln
        155                 160                 165 gaa tat gaa gcc atc tac cta gca aaa tta aca ata cag atg atg tca         640
Glu Tyr Glu Ala Ile Tyr Leu Ala Lys Leu Thr Ile Gln Met Met Ser
    170                 175                 180 cca ctc cag ata gaa agg tca tta tct gtt cat tct ggt acc aca ggc         688
Pro Leu Gln Ile Glu Arg Ser Leu Ser Val His Ser Gly Thr Thr Gly
185                 190                 195                 200 agt ttg aag aga aca cat gaa gaa gag gat gat ttt gga acc atg caa         736
Ser Leu Lys Arg Thr His Glu Glu Glu Asp Asp Phe Gly Thr Met Gln
                205                 210                 215 gtg gcg act gca cag aat ggc tgacttgaag agcaacatca tagagtgtga           787
Val Ala Thr Ala Gln Asn Gly
                220 atttctattt gggaaggaga aaatacaaga gaaaattata atgtaaaatg gtaaaaacat       847 aagtagtttt tttttcaatt acatgttgct tccagacata cttctctgca acttgttgag       907 caacatttta agatgttgga cttctgcaat agatgacact gatggtttta ctccttttt       967 taaaaacaca tgcgcgcgca cacacacatg ctttacaagt tttattataa accaagaatt      1027 ttggacttgc aaagaggtat tattgcaata atgcactttt catacttgaa atttatttgt      1087 atgatataaa gttattactt taaacaa                                          1114

<210> SEQ ID NO 5
<211> LENGTH: 223
<212> TYPE: PRT
<213> ORGANISM: Homo sapiens

<400> SEQUENCE: 5

Met Glu Asp Val Lys Leu Glu Phe Pro Ser Leu Pro Gln Cys Lys Glu
 1               5                  10                  15

Asp Ala Glu Glu Trp Thr Tyr Pro Met Arg Arg Glu Met Gln Glu Ile
```

```
                     20                  25                  30
Leu Pro Gly Leu Phe Leu Gly Pro Tyr Ser Ser Ala Met Lys Ser Lys
                 35                  40                  45
Leu Pro Val Leu Gln Lys His Gly Ile Thr His Ile Cys Ile Arg
 50                  55                  60
Gln Asn Ile Glu Ala Asn Phe Ile Lys Pro Asn Phe Gln Gln Leu Phe
 65                  70                  75                  80
Arg Tyr Leu Val Leu Asp Ile Ala Asp Asn Pro Val Glu Asn Ile Ile
                 85                  90                  95
Arg Phe Phe Pro Met Thr Lys Glu Phe Ile Asp Gly Ser Leu Gln Met
                100                 105                 110
Gly Gly Lys Val Leu Val His Gly Asn Ala Gly Ile Ser Arg Ser Ala
                115                 120                 125
Ala Phe Val Ile Ala Tyr Ile Met Glu Thr Phe Gly Met Lys Tyr Arg
                130                 135                 140
Asp Ala Phe Ala Tyr Val Gln Glu Arg Arg Phe Cys Ile Asn Pro Asn
145                 150                 155                 160
Ala Gly Phe Val His Gln Leu Gln Glu Tyr Glu Ala Ile Tyr Leu Ala
                165                 170                 175
Lys Leu Thr Ile Gln Met Met Ser Pro Leu Gln Ile Glu Arg Ser Leu
                180                 185                 190
Ser Val His Ser Gly Thr Thr Gly Ser Leu Lys Arg Thr His Glu Glu
                195                 200                 205
Glu Asp Asp Phe Gly Thr Met Gln Val Ala Thr Ala Gln Asn Gly
                210                 215                 220

<210> SEQ ID NO 6
<211> LENGTH: 672
<212> TYPE: DNA
<213> ORGANISM: Homo sapiens

<400> SEQUENCE: 6
atggaggacg tgaagctgga gttcccttcc cttccacagt gcaaggaaga cgccgaggag    60
tggacctacc ctatgagacg agagatgcag gaaattttac ctggattgtt cttaggccca   120
tattcatctg ctatgaaaag caagctacct gtactacaga acatggaat aacccatata   180 atatgcatac gacaaaatat tgaagcaaac tttattaaac caaactttca gcagttattt   240
agatatttag tcctggatat tgcagataat ccagttgaaa atataatacg ttttttccct   300
atgactaagg aatttattga tgggagctta caaatgggag aaaagttct tgtgcatgga   360 aatgcaggga tctccagaag tgcagccttt gttattgcat acattatgga aactttgga   420 atgaagtaca gagatgcttt tgcttatgtt caagaaagaa gattttgtat taatcctaat   480
gctggatttg tccatcaact tcaggaatat gaagccatct acctagcaaa attaacaata   540
cagatgatgt caccactcca gatagaaagg tcattatctg ttcattctgg taccacaggc   600
agtttgaaga gaacacatga agaagaggat gattttggaa ccatgcaagt ggcgactgca   660
cagaatggct ga                                                       672

<210> SEQ ID NO 7
<211> LENGTH: 173
<212> TYPE: PRT
<213> ORGANISM: Artificial Sequence
<220> FEATURE:
<223> OTHER INFORMATION: consensus sequence

<400> SEQUENCE: 7
```

```
Gly Pro Ser Glu Ile Leu Pro His Leu Tyr Leu Gly Ser Tyr Ser Thr
 1               5                  10                  15

Ala Ser Glu Ala Asn Leu Ala Leu Leu Lys Lys Leu Gly Ile Thr His
             20                  25                  30

Val Ile Asn Val Thr Glu Glu Val Pro Asn Pro Phe Glu Leu Asp Lys
             35                  40                  45

Lys Asn Asp Arg His Tyr Thr Asn Ala Tyr Ile Ser Lys Asn Ser Gly
         50                  55                  60

Phe Thr Tyr Leu Gln Ile Pro Asn Val Asp Asp His Ile Tyr Tyr His
 65                  70                  75                  80

Ile Ala Trp Asn His Glu Thr Lys Ile Ser Lys Tyr Phe Asp Glu Ala
                 85                  90                  95

Val Asp Phe Ile Asp Asp Ala Arg Gln Lys Gly Gly Lys Val Leu Val
                100                 105                 110

His Cys Gln Ala Gly Ile Ser Arg Ser Ala Thr Leu Ile Ile Ala Tyr
                115                 120                 125

Leu Met Lys Thr Arg Asn Leu Ser Leu Asn Glu Ala Tyr Asp Phe Val
        130                 135                 140

Tyr Val Tyr His Ile Lys Glu Arg Arg Cys Pro Ile Ile Ser Pro Asn
145                 150                 155                 160

Phe Gly Phe Leu Arg Gln Leu Ile Glu Tyr Glu Arg Lys
                165                 170

<210> SEQ ID NO 8
<211> LENGTH: 172
<212> TYPE: PRT
<213> ORGANISM: Artificial Sequence
<220> FEATURE:
<223> OTHER INFORMATION: consensus sequence

<400> SEQUENCE: 8

Gly Pro Ser Glu Ile Leu Pro His Leu Tyr Leu Gly Ser Tyr Ser Asp
 1               5                  10                  15

Ala Ser Glu Ala Asn Leu Ala Leu Leu Lys Lys Leu Gly Ile Thr His
             20                  25                  30

Val Ile Asn Val Thr Glu Glu Val Pro Asn Asn Phe Glu Leu Lys Lys
             35                  40                  45

Lys Asn Asp Arg Tyr Tyr Thr Asn Glu Tyr Ile Ser Lys Gly Ser Gly
         50                  55                  60

Phe Thr Tyr Leu Gln Ile Pro Asn Val Asp Asp Ile Tyr Tyr His Ile
 65                  70                  75                  80

Ala Trp Asn Thr Glu Thr Lys Ile Ser Lys Tyr Leu Glu Glu Ala Val
                 85                  90                  95

Glu Phe Ile Glu Asp Ala Glu Lys Lys Gly Gly Lys Val Leu Val His
                100                 105                 110

Cys Gln Ala Gly Val Ser Arg Ser Ala Thr Leu Val Ile Ala Tyr Leu
                115                 120                 125

Met Lys Thr Arg Asn Leu Ser Leu Arg Asp Ala Tyr Asp Phe Val Tyr
        130                 135                 140

Val Tyr His Ile Lys Glu Arg Arg Cys Pro Ile Ile Ser Pro Asn Phe
145                 150                 155                 160

Gly Phe Leu Arg Gln Leu Ile Glu Tyr Glu Arg Lys
                165                 170

<210> SEQ ID NO 9
```

```
<211> LENGTH: 131
<212> TYPE: PRT
<213> ORGANISM: Artificial Sequence
<220> FEATURE:
<223> OTHER INFORMATION: consensus sequence

<400> SEQUENCE: 9

Thr Ala Gly Glu Leu Lys Ala Leu Leu Glu Ser Ala Pro Lys Leu Ile
 1               5                  10                  15

Leu Ile Asp Val Arg Ser Pro Glu Phe Gly Glu Glu Tyr Glu Tyr Glu
            20                  25                  30

Gly Gly His Ile Pro Gly Ala Val Asn Val Pro Glu Glu Ile Glu
            35                  40                  45

Ala Leu Leu Asp Arg Ser Gly Ile Leu Pro Asp Ile Glu Lys Leu His
 50                      55                  60

Leu Leu Lys Asp Pro Glu Glu Leu Ala Lys Leu Phe Gly Glu Leu Gly
 65                  70                  75                  80

Ser Ser Lys Asp Lys Arg Val Ile Val Tyr Cys Arg Ser Gly Arg Gly
                 85                  90                  95

Leu Leu Arg Asn Arg Arg Ser Ala Leu Ala Ala Leu Leu Lys Lys
                100                 105                 110

Leu Gly Tyr Pro Glu Val Tyr Ile Leu Lys Gly Gly Tyr Lys Glu Trp
            115                 120                 125

Leu Ala Lys
    130

<210> SEQ ID NO 10
<211> LENGTH: 94
<212> TYPE: PRT
<213> ORGANISM: Artificial Sequence
<220> FEATURE:
<223> OTHER INFORMATION: consensus sequence

<400> SEQUENCE: 10

Val Leu Glu Glu Leu Lys Leu Leu Asn Glu Asp Val Val Leu Leu
 1               5                  10                  15

Asp Val Arg Ser Pro Glu Glu Tyr Glu Gly Gly His Ile Pro Gly Ala
            20                  25                  30

Val Asn Ile Pro Leu Ser Glu Leu Leu Asp Arg Leu Gly Leu Asp Lys
            35                  40                  45

Asp Lys Pro Val Ile Val Tyr Cys Arg Ser Gly Val Arg Ser Ala Ala
 50                      55                  60

Lys Ala Ala Trp Leu Leu Arg Glu Leu Gly Phe Lys Asn Val Tyr Leu
 65                  70                  75                  80

Leu Asp Gly Gly Tyr Lys Glu Trp Ser Ala Ala Gly Pro Pro
                 85                  90
```

What is claimed is:

1. An isolated nucleic acid molecule selected from the group consisting of:
   a) a nucleic acid molecule comprising a nucleotide sequence of SEQ ID NO:1, or SEQ ID NO:3; and
   b) a nucleic acid molecule which encodes a polypeptide comprising the amino acid sequence of the SEQ ID NO:2.

2. The nucleic acid molecule of claim 1 further comprising vector nucleic acid sequences.

3. The nucleic acid molecule of claim 1 further comprising nucleic acid sequences encoding a heterologous polypeptide.

4. An isolated non-mammalian host cell which contains the nucleic acid molecule of claim 1.

5. An isolated non-human mammalian host cell containing the nucleic acid molecule of claim 1.

6. A method for producing a polypeptide encoded by the nucleic acid of claim 1, comprising culturing a host cell containing said nucleic acid under conditions in which the nucleic acid is expressed.

* * * * *